United States Patent [19]

Beavo et al.

[11] Patent Number: 5,800,987
[45] Date of Patent: Sep. 1, 1998

[54] ASSAY METHODS USING DNA ENCODING MAMMALIAN PHOSPHODIESTERASES

[75] Inventors: Joseph A. Beavo; J. Kelley Bentley, both of Seattle, Wash.; Harry Charbonneau, W. Lafayette, Ind.; William K. Sonnenburg, Mountlake Terrace, Wash.

[73] Assignee: The Board of Regents of The University of Washington, Seattle, Wash.

[21] Appl. No.: 455,525

[22] Filed: May 31, 1995

Related U.S. Application Data

[62] Division of Ser. No. 297,494, Aug. 29, 1994, Pat. No. 5,580,771, which is a division of Ser. No. 872,644, Apr. 20, 1992, Pat. No. 5,389,527, which is a continuation-in-part of Ser. No. 688,356, Apr. 19, 1991, abandoned.

[51] Int. Cl.$^6$ .................................................. C12Q 1/68
[52] U.S. Cl. .............................. 435/6; 435/29; 435/196; 435/254.21; 435/252.3
[58] Field of Search ........................ 435/29, 196, 254.21, 435/252.3, 6

[56] References Cited

U.S. PATENT DOCUMENTS

4,980,281 12/1990 Housey ..................... 435/29

OTHER PUBLICATIONS

Ausubel, et al., eds., Current Protocols in Molecular Biology, 1: 1.7.1–1.7.2 and 9.2.1–9.2.3, John Wiley & Sons, New York (1989).
Beavo, J.A., "Multiple Isozymes of Cyclic Nucleotide Phosphodiesterase," Advances in Second Messenger and Phosphoprotein Research, 22: 1–38 (1988).
Beavo, J.A., "Multiple Phosphodiesterase Isoenzymes Background, Nomenclature and Implications", pp. 3–15; Cyclic Nucleotide Phosphodiesterases; Structure, Regulation and Drug Action, J. Beavo and Houslay, M.D., Eds.; John Wiley & Sond, Ltd., New York (1990).
Brinstiel, M.L., et al., "Transcription Termination and 3' Processing: The End Is in Sight!", Cell, 41: 349–359 (1985).
Bourne, H.R., et al., "Somatic Genetic Analysis of Cyclic AMP Action: Characterization of Unresponsive Mutants," J. Cell. Physiol., 85: 611–620 (1985).
Bradford, M.M., "A Rapid and Sensitive Method for the Quantitation of Microgram Quantities of Protein Utilizing the Principle of Protein–Dye Binding," Analytical Biochem., 72: 248–254 (1976).
Chen, C–N., et al., "Molecular Analysis of cDNA Clones and the Corresponding Genomic Coding Sequences of the Drosophila dunce$^+$Gene, the Structural Gene for cAMP Phosphodiesterase," Proc. Nat'l. Acad. Sci. (USA), 83: 9313–9317 (1986).
Chomczynski, P., et al., "Single–Step Method of RNA Isolation by Acid Guanidinium Thiocyanate–Phenol–Chloroform Extraction," Analytical Biochem,, 162: 156–159 (1987).

Colicelli, J., et al., "Isolation and Characterization of a Mammalian Gene Encoding a High–Affinity cAMP Phosphodiesterase," Proc. Nat'l. Acad. Sci. (USA), 86: 3599–3603 (1989).
Davis, R.L., "Molecular Genetics of the Cyclic Nucleotide Phosphodiesterases", pp. 227–241 in Cyclic Nucleotide Phosphodiesterases: Structure, Regulation and Drug Action, J. Beavo and Houslay, M.D., Eds.; John Wiley & Sons, Ltd., New York (1990).
Davis, R.L., et al., "Cloning and Characterization of Mammalian Homologs of the Drosophila dunce$^+$Gene," Proc. Nat'l Acad. Sci. (USA), 86: 3604–3608 (1989).
Devereux, J., et al., "A Comprehensive Set of Sequence Analysis Programs for the VAX," Nucleic Acids Res., 12: 387–395 (1984).
Erneux, C., et al., "A Mechanism in the Control of Intracellular cAMP Levels: The Activation of a Calmodulin–Sensistive Phosphodiesterase by a Rise of Intracellular Free Calcium," Mol. Cell. Endocrinol., 43:123–134 (1985).
Faure, M., et al., "Disruption of Dictyostelium discoideum Morphogenesis by Overproduction of cAMP Phosphodiesterase," Proc. Nat'l. Acad. Sci. (USA), 85: 8076–8080 (1988).
Feinberg, A.P., et al., "A Technique for Radiolabeling DNA Restriction Endonuclease Fragments to High Specific Activity," Analytical Biochem., 137: 266–267 (1984).
Greenberg, L.H., et al., "Enzymatic Regulation of the Concentration of Cyclic GMP in Mouse Brain," Neuropharmacology, 17: 737–745 (1978).
Hansen, R.S., et al., "Differential Recognition of Calmodulin–Enzyme Complexes by a Conformation–Specific Anti–Calmodulin Monoclonal Antibody," J. Biol. Chem., 261: 14636–14645 (1986).
Hansen, R.S., et al., "Purification of Calmodulin–Stimulated Cyclic Nucleotide Phosphodiesterase by Monoclonal Antibody Affinity Chromatography," Meth. Enzymol., 159: 543–557 (1988).
Hansen, R.S., et al., "Purification of Two Calcium/Calmodulin–Dependent Forms of Cyclic Nucleotide Phosphodiesterase by Using Comformation–Specific Monoclonal antibody Chromatography," Proc. Nat'l. Acad. Sci. (USA), 79: 2788–2792 (1982).

(List continued on next page.)

Primary Examiner—Dian C. Jacobson
Assistant Examiner—Enrique D. Longton
Attorney, Agent, or Firm—Marshall, O'Toole, Gerstein, Murray & Borun

[57] ABSTRACT

The present invention relates to novel purified and isolated nucleotide sequences encoding mammalian $Ca^{2+}$/calmodulin stimulated phosphodiesterases (CaM-PDEs) and cyclic-GMP-stimulated phosphodiesterases (cGS-PDEs). Also provided are the corresponding recombinant expression products of said nucleotide sequences, immunological reagents specifically reactive therewith, and procedures for identifying compounds which modulate the enzymatic activity of such expression products.

4 Claims, 3 Drawing Sheets

OTHER PUBLICATIONS

Hashimoto, Y., et al., "Regulation of $Ca^{2+}$/Calmodulin–Dependent Cyclic Nucleotide Phosphodiesterase by the Autophosphorylated Form of $Ca^{2+}$/Calmodulin–Dependent Protein Kinase II," *J. Biol. Chem.*, 264: 10884–10887 (1989).

Henikoff, S., "Unidirectional Digestion with Exonuclease III Creates Targeted Breakpoints for DNA Sequencing," *Gene*, 28: 351–359 (1984).

Kincaid, R.L., et al., "Differential Localization of Calmodulin–Dependint Enzymes in Rat Brain: Evidence for Selective Expression of Cyclic Nucleotide Phosphodiesterase in Specific Neurons," *Proc. Nat'l. Acad. Sci. (USA,* 84: 1118–1122 (1987).

Kozak, M., "The Scanning Model for Translation: An Update," *J. Cell Biol,*, 108: 229–241 (1989).

Krinks, M.H., et al., "Reversible and Irreversible Activation of Cyclic Nucleotide Phosphodiesterase: Separation of the Regulatory and Catalytic Domains by Limited Proteolysis," *Advances in Cyclic Nucleotide and Protein Phosphorylation Research*, 16: 31–47 (1984).

LaPorte, D.C., et al., "Cross–Linking of Iodine–125–Labeled, Calcium–Dependent Regulatory Protein to the $Ca^{2+}$–Sensitive Phosphodiesterase Purified from Bovine Heart," *Biochemistry*, 18: 2820–2825 (1979).

LeTrong, H., et al., "Amino Acid Sequence of the Cyclic GMP Stimulated Cyclic Nucleotide Phosphodiesterase from Bovine Heart," *Biochemistry*, 29: 10280–10288 (1990).

Livi, G.P., et al., "Cloning and Expression of cDNA for a Human Low–$K_m$ Rolipram–Sensitive Cyclic AMP Phosphodiesterase," *Mol. Cell. Biol.*, 10: 2678–2686 (1990).

Manganiello, V.C., et al., "Cyclic GMP–Stimulated Cyclic Nucleotide Phosphodiesterases", pp. 62–85 in *Cyclic Nucleotide Phosphodiesterases: Structure, Regulation and Drug Action*, Beavo, J. and Houslay, M.D., Eds.; John Wiley & Sons, Ltd., New York (1990).

Maniatis, et al., *Molecular Cloning: A Laboratory Manual*, pp. 326–328, Cold Spring Harbor Laboratory, Cold Spring Harbor, New York (1982).

Martins, T.J., et al., "Purification and Characterization of a Cyclic GMP–Stimulated Cyclic Nucleotide Phosphodiesterase from Bovine Tissues," *J. Biol. Chem.*, 257: 1973–1979 (1982).

Nikawa, J–I., et al., "Cloning and Characterization of the Low–Affinity Cyclic AMP Phosphodiesterase Gene of *Saccaromyces cerevisiae*," *Mol. Cell. Biol.*, 7: 3629–3636 (1987).

Nomenclature Committee of the International Union of Biochemistry (NCIUB), "Nomenclature for Incompletely Specified Bases in Nucleic Acid Sequences," *J. Biol. Chem.*, 261:13–17 (1986).

Novack, J.P., et al., "Sequence Comparison of the 63–, 61–, and 59–kDa Calmodulin–Dependent Cyclic Nucleotide Phosphodiesterases," *Biochemistry*, 30: 7940–7947 (1991).

Ovchinnikov, Y.A., et al., "Cyclic GMP Phosphodiesterase from Bovine Retina," *FEBS*, 223: 169–173 (1987).

Sanger, F., et al., "DNA Sequencing with Chain–Terminating Inhibitors," *Proc. Nat'l. Acad. Sci. (USA),* 74: 5463–5467 (1977).

Sass, P., et al., "Cloning and Characterization of the High–Affinity cAMP Phosphodiesterase of *Saccromyces cerevisiae*," *Proc. Nat'l. Acad. Sci. (USA),* 83: 9303–9307 (1986).

Seed, B., "An LFA–3 cDNA encodes a Phospholipid–Linked Membrane Proein Homologous to Its Receptor CD2," *Nature*, 329: 840–843 (1987).

Sharma, R.K., et al., "Demonstration of Bovine Brain Calmodulin–Dependent Cyclic Nucleotide Phosphodiesterase Isozymes by Monoclonal Antibodies," *J. Biol. Chem.*, 259: 9248–9254 (1984).

Sharma, R.K., et al., "Differential Regulation of Bovine Brain Calmodulin–Dependent Cyclic Nucleotide Phosphodiesterase Isozymes by Cyclic AMP–Dependent Protein Kinase and Calmodulin–Dependent Phosphatase," *Proc. Nat'l. Acad. Sci. (USA)*, 82: 2603–2607 (1985).

Sharma, R.K., et al., "Purification and Characterization of Bovine Lung Calmodulin–Dependent Cyclic Nucleotide Phosphodiesterase," *J. Biol. Chem.*, 261: 14160–14166 (1986).

Short, M., et al., "ZAP: A Bacteriophage λ Expression Vector with in vivo Excision Properties," *Nucleic Acids Res.*, 16: 7583–7600 (1988).

Sonnenburg, W.K., et al., "Molecular Cloning of a Cyclic GMP–Stimulated Cyclic Nucleotide Phosphodiesterase cDNA," *J. Biol. Chem.*, 266(26): 17655–17661 (1991).

Stroop, S.D., et al., "Direct Photolabeling of the cGMP––Stimulated Cyclic Nucleotide Phosphodiesterase," *J. Biol. Chem.*, 264: 13718–13725 (1989).

Swinnen, J.V., et al., "Molecular Cloning of Rat Homologues of the *Drosophila melanogaster* dunce cAMP Phosphodiesterase: Evidence for a Family of Genes," *Proc. Nat'l. Acad. Sci. (USA),* 86: 5325–5329 (1989).

Tanner, L.I., et al., "Identification of the Phosphodiesterase Regulated by Muscarinic Chlinergic Receptors of the 1321N1 Human Astrocytoma Cells," *Mol. Pharmacol.*, 29: 455–460 (1986).

Thompson, W.J., et al., "Identification of Type II (Cyclic GMP–Stimulatable) Cyclic Nucleotide Phosphodiesterase (CNPDE) mRNA in Rat Pheochromocytoma Cells (PC12)," *FASEB J.*, 5(6): A1592 (Abstract No. 7092) (Mar. 1991).

Wang, J.H., et al., "Calmodulin–Stimulated Cyclic Nucleotide Phosphodiesterases", pp. 19–59; in *Cyclic Nucleotide Phosphodiesterases: Structure, Regulation and Drug Action*, Beavo, J. and Houslay, M.D., Eds.; John Wiley & Sons, Ltd., New York (1990).

Watson, et al., "An Alternative Procedure for the Synthesis of Double–Stranded cDNA for Cloning in Phage and Plasmid Vectors," pp. 79–88; in *DNA Cloning: A Practical Approach*, 1 (1985).

Wilson, R.B., et al., "SRA5 Encodes the Low–$K_m$ Cyclic AMP Phosphodiesterase of *Saccharomyces cerevisiae*," *Mol. Cell. Biol.*, 8: 505–510 (1988).

Charbonneau, H., et al., "Identification of a conserved domain among cyclic nucleotide phosphodiesterases from diverse species," *Proc. Nat'l. Acad. Sci. (USA*: 83: 9308–9312 (1986).

Trong, H. L., et al., "Amino Acid Sequence of the Cyclic GMP Stimulated Cyclic Nucleotide Phosphodiesterase from Bovine Heart," *Biochemistry 1990*, 29: 10280–10288.

```
                190       200       210       220       230       240
                 |         |         |         |         |         |
59kDa:                           ELFTRYDLINRFKIPVsCLIAFAEAALEVGyskYKNPYHNLIHAADVTQTVHYIMLHTGIM
61kDA:                           ELFTRYDLINRFKIPVSCLIAFAEAALEVGYSKYKNPYHNLIHAADVTQTVHYIMLHTGIM
63kDA:          KIPTVFLMTELDALETGYGK 250       260       270       280       290       300
                 |         |         |         |         |         |
59kDa:          HWLTELEILAMVFAAAIHDYEHTGTTNNFHIQtrsSDVAILYNQRSVLENHHVSAAYR---
61kDA:          HWLTELEILAMVFAAAIHDYEHTGTTNNFHIQTRSDVAILYNQRSVLENHHVSAAYRLMQ
63kDA:                                         kDETAILYNdRTYLEN 310       320       330       340       350       360
                 |         |         |         |         |         |
59kDa:          ---MNVLINLSKDDWRDLRNLVIEM-LST------KNIRNSLOOPEGLDK-KTMSLI
61kDA:          EEEMNVLINLSKDDWRDLRNLVIEMVLSTDMSGHFQQIKNIRNSLOOPEGLDKAKTMSLI
63kDA:                                             kTALQQLERIDK kALSLL
```

```
                   370       380       390       400       410       420
                    |         |         |         |         |         |
59kDa:             LHAADISHPAKSWKLHHRWTWALMEEFFLQGDKEAELGLPFSPLCDRKSTMVAQSQIGFI
61kDa:             LHAADISHPAKSWKLHHRWTWALMEEFFLQGDKEAELGLPFSPLCDRKSTMVAQSQIGFI
63kDa:             LHAADISHPTKQWSVHSRWTKALMEEFFRQGDK 430       440       450       460       470       480
                    |         |         |         |         |         |
59kDa:             DFIVEPTFSLLTDSTEKIIIPLIEEDSKIKTPSYGASRRSNMKGTTNDGTYSPDYSLASV
61kDa:             DFIVEPTFSLLTDSTEKIIIPLIEEDSKIKTPSYGASRRSNMKGTTNDGTYSPDYSLASV
63kDa:

490       500       510       520       529
                    |         |         |         |         |
59kDa:             DLKSFKNSLVDIIQQNKERWKELAAQGEPDPHKNSDLVNAEEKHAETHS
61kDa:             DLKSFKNSLVDIIQQNKERWKELAAQGEPDPHKNSDLVNAEEKHAETHS
63kDa:
```

ASSAY METHODS USING DNA ENCODING MAMMALIAN PHOSPHODIESTERASES

This is a Rule 60 Divisional of U.S. patent application Ser. No. 08/297,494, U.S. Pat. No. 5,580,771 filed Aug. 29, 1994, which in turn is a Rule 60 Divisional of U.S. patent application Ser. No. 07/872,644, U.S. Pat. No. 5,389,527 filed Apr. 20, 1992, which is a continuation-in-part of our U.S. patent application No. 07/688,356, filed Apr. 19, 1991, now abandoned.

BACKGROUND OF THE INVENTION

The present invention relates to novel purified and isolated nucleotide sequences encoding mammalian $Ca^{2+}$/calmodulin stimulated phosphodiesterases (CaM-PDEs) and cyclic-GMP-stimulated phosphodiesterases (cGS-PDEs). Also provided are the corresponding recombinant expression products of said nucleotide sequences, immunological reagents specifically reactive therewith, and procedures for identifying compounds which modulate the enzymatic activity of such expression products.

Cyclic nucleotides are known to mediate a wide variety of cellular responses to biological stimuli. The cyclic nucleotide phosphodiesterases (PDEs) catalyze the hydrolysis of 3', 5' cyclic nucleotides, such as cyclic adenosine monophosphate (cAMP) and cyclic guanosine monophosphate (cGMP), to their corresponding 5'-nucleotide monophosphates and are consequently important in the control of cellular concentration of cyclic nucleotides. The PDEs in turn are regulated by transmembrane signals or second messenger ligands such as calcium ion ($Ca^{2+}$) or cGMP. The PDEs thus have a central role in regulating the flow of information from extracellular hormones, neurotransmitters, or other signals that use the cyclic nucleotides as messengers.

PDEs are a large and complex group of enzymes. They are widely distributed throughout the cells and tissues of most eukaryotic organisms, but are usually present only in trace amounts. At least five different families of PDEs have been described based on characteristics such as substrate specificity, kinetic properties, cellular regulatory control, size, and in some instances, modulation by selective inhibitors. [Beavo, Adv. in Second Mess. and Prot. Phosph. Res. 22:1–38 (1988)]. The five families include:

I $Ca^{2+}$/calmodulin-stimulated

II cGMP-stimulated

III cGMP-inhibited

IV cAMP-specific

V cGMP-specific

Within each family there are multiple forms of closely related PDEs. See Beavo, "Multiple Phosphodiesterase Isozymes Background, Nomenclature and Implications", pp. 3–15; Wang et al., "Calmodulin-Stimulated Cyclic Nucleotide Phosphodiesterases", pp. 19–59; and Manganiello et al., "Cyclic GMP-Stimulated Cyclic Nucleotide Phosphodiesterases" pp. 62–85; all in *Cyclic Nucleotide Phosphodiesterases: Structure. Regulation and Drug Action*, Beavo, J. and Houslay, M. D., Eds.; John Wiley & Sons, New York (1990).

The $Ca^{2+}$/calmodulin dependent PDEs (CaM-PDEs) are characterized by their responsiveness to intracellular calcium, which leads to a decreased intracellular concentration of cAMP and/or cGMP. A distinctive feature of cGMP-stimulated phosphodiesterases (cGS-PDEs) is their capacity to be stimulated by cGMP in effecting cAMP hydrolysis.

In vitro studies have shown increased PDE activity in response to $Ca^{2+}$/calmodulin in nearly every mammalian tissue studied, as well as in Drosophila, Dictyostelium, and trypanosomes. The level of CaM-PDE in tissues and cellular and subcellular compartments varies widely. Most cells contain at least a small amount of CaM-PDE activity, with the highest tissue levels being found in the brain, particularly in the synaptic areas. Greenberg et al. *Neuropharmacol.*, 17:737–745 (1978) and Kincaid et al., *PNAS (USA)*, 84:1118–1122 (1987). A decrease in cAMP in astrocytoma cells in response to muscarinic stimulation may be due to calcium dependent increases in CaM-PDE activity. Tanner et al., *Mol. Pharmacol.*, 29:455–460 (19B6). Also, CaM-PDE may be an important regulator of cAMP in thyroid tissue. Erneux et al., *Mol. Cell. Endocrinol.*, 43:123–134(1985).

Early studies suggested that there are distinct tissue-specific isozymes of CaM-PDEs. Several members of the CaM-PDE family have now been described, including a 59 kDa isozyme isolated from bovine heart, and 61 and 63 kDa isozymes isolated from bovine brain. LaPorte et al., *Biochemistry*, 18:2820–2825 (1979); Hansen et al., *Proc. Natl. Acad. Sci. USA*, 79:2788–2792 (1982); and Sharma et al., *J. Biol. Chem.*, 261:3.4160–14166 (1986). Possible counterparts to the bovine 59 and 61 kDa isozymes have also been isolated from rat tissues, Hansen et al., *J. Biol. Chem.*, 261:14636–14645 (1986), suggesting that these two isozymes may be expressed in other mammalian species.

In addition to molecular weight criteria, other evidence supports both similarities and differences among the CaM-PDE family of isozymes. For example, the 59 kDa heart isozyme and the 61 kDa brain isozyme CaM-PDEs differ in mobility on SDS-PAGE and elution position on DEAE chromatography, and the 59 kDa isozyme has at least a 10–20 fold higher affinity for calmodulin. Oncomodulin, a fetal/onco calcium binding protein present in very high concentrations in the placenta and transformed cells, also binds to the 59 kDa enzyme with a higher affinity than to the 61 kDa enzyme. However, both the 61 kDa brain and the 59 kDa heart isozymes are recognized by a single monoclonal antibody. This antibody binds to the $Ca^{2+}$/CaM-PDE complex with 100-fold higher affinity than to PD. alone. Hansen et al., 1986, supra. The 59 and 61 kDA isozymes have nearly identical substrate specificities and kinetic constants. Krinks et al., *Adv. Cyc. Nucleotide Prot. Phosphorylation Res.*, 16:31–47 (1984) have suggested, based on peptide mapping experiments, that the heart 59 kDa protein could be a proteolytic form of the brain 61 kDa isozyme.

The 63 kDa bovine brain isozyme differs substantially from the 59 and 61 kDa isozymes. The 63 kDa enzyme is not recognized by the monoclonal antibody which binds to the 59 and 61 kDa enzymes. Hansen et al., 1986, supra. The 63 kDa protein is not phosphorylated in vitro by cAMP-dependent protein kinase, whereas the 61 kDa protein is phosphorylated. Further, only the 63 kDa protein is phosphorylated in vitro by CaM-kinase II. Sharma et al., *Proc. Natl. Acad. Sci. (USA)*, 82:2603–2607 (1985); and Hashimoto et al., *J. Biol. Chem.*, 264:10884–10887 (1989). The 61 and 63 kDa CaM-PDE isozymes from bovine brain do appear, however, to have similar CaM-binding affinities. Peptide maps generated by limited proteolysis with Staphylococcal V8 protease, Sharma et al., *J. Biol.Chem.*, 259:9248 (1984), have suggested that the 61 and 63 kDa proteins; have different amino acid sequences.

The cGMP-stimulated PDEs (cGS-PDEs) are proposed to have a noncatalytic, cGMP-specific site that may account for the stimulation of cAMP hydrolysis by cGMP. Stoop et al., *J.Biol.Chem.*, 264:13718 (1989). At physiological cyclic nucletotide concentrations, this enzyme responds to elevated cGMP concentrations with an enhanced hydrolysis of cAMP. Thus, cGS-PDE allows for increases in cGMP concentration to moderate or inhibit cAMP-mediated responses. The primary sequence presented recently in LeTrong et al., Biochemistry, 29:10280 (1990), co-authored by the inventors herein, provides the molecular framework for understanding the regulatory properties and domain substructure of this enzyme and for comparing it with other PDE isozymes that respond to different signals. This publication also notes the cloning of a 2.2 kb bovine adrenal cortex cDNA fragment encoding cGS-PDE. See also, Thompson et al., FASEB J., 5(6):A1592 (Abstract No. 7092) reporting on the cloning of a "Type II PDE" from rat pheochromocytoma cells.

With the discovery of the large number of different PDEs and their critical role in intracellular signalling, efforts have focused on finding agents that selectively activate or inhibit specific PDE isozymes. Agents which affect cellular PDE activity, and thus alter cellular cAMP, can potentially be used to control a broad range of diseases and physiological conditions. Some drugs which raise cAMP levels by inhibiting PDEs are in use, but generally act as broad nonspecific inhibitors and have deleterious side effects on cAMP activity in nontargeted tissues and cell types. Accordingly, agents are needed which are specific for selected PDE isozymes. Selective inhibitors of specific PDE isozymes may be useful as cardiotonic agents, anti-depressants, anti-hypertensives, anti-thrombotics, and as other agents. Screening studies for agonists/antagonists have been complicated, however, because of difficulties in identifying the particular PDE isozyme present in a particular assay preparation. Moreover, all PDEs catalyze the same basic reaction; all have overlapping substrate specificities; and all occur only in trace amounts.

Differentiating among PDEs has been attempted by several different mean. The classical enzymological approach of isolating and studying each new isozyme is hampered by current limits of purification techniques and by the inability to accurately assess whether complete resolution of an isozyme has been achieved. A second approach has been to identify isozyme-specific assay conditions which might favor the contribution of one isozyme and minimize that of others. Another approach has been the immunological identification and separation into family groups and/or individual isozymes. There are obvious problems with each of these approaches; for the unambiguous identification and study of a particular isozyme, a large number of distinguishing criteria need to be established, which is often time consuming and in some cases technically quite difficult. As a result, most studies have been done with only partially pure PDE preparations that probably contained more than one isozyme. Moreover, many of the PDEs in most tissues are very susceptible to limited proteolysis and easily form active proteolytic products that may have different kinetic, regulatory, and physiological properties from their parent form.

The development of new and specific PDE-modulatory agents would be, greatly facilitated by the ability to isolate large quantities of tissue-specific PDEs by recombinant means. Relatively few PDE genes have been cloned to date and of those cloned, most belong to the cAMP-specific family of phosphodiesterases (cAMP-PDEs). See Davis, "Molecular Genetics of the Cyclic Nucleotide Phosphodiesterases", pp. 227–241 in Cyclic Nucleotide Phosphodiesterases: Structure, Regulation, and Drug Action, Beavo, J and Houslay, M. D., Eds.; John Wiley & Sons, New York; 1990. See also, e.g., Faure et al., PNAS (USA), 85:8076 (1988)—D. discoideum; Sass et al., PNAS (USA), 83:9303 (1986)—S. cerevisiae, PDE class IV, designated PDE2; Nikawa et al., Mol. Cell. Biol., 7:3629 (1987)—S. cerevisiae, designated PDE1; Wilson et al., Mol. Cell. Biol., 8:505 (1988)—S. cerevisiae, designated SRA5; Chen et al., PNAS (USA), 83:9313 (1986)—D. melanogaster, designated dnc$^+$; Ovchinnikow et al., FEBS, 223:169 (1987) bovine retina, designated GMP PDE; Davis et al., PNAS (USA), 86:3604 (1989)—rat liver, designated rat dnc-1; Colicelli et al., PNAS (USA), 86:3599 (1989)—rat brain, designated DPD; Swinnen et al., PNAS (USA), 86:5325 (1989)—rat testis, rat PDE1, PDE2, PDE3 and PDE4; and Livi et al., Mol. Cell. Biol., 10:2678 (1990)—human monocyte, designated hPDE1. See also, LeTrong et al., supra and Thompson et al., supra.

Complementation screening has been used to detect and isolate mammalian cDNA clones encoding certain types of PDEs. Colicelli et al., PNAS (USA), 86:3599 (1989), reported the construction of a rat brain cDNA library in an S. cerevisiae expression vector and the isolation therefrom of genes having the capacity to function in yeast to suppress the phenotypic effects of RAS2$^{va119}$, a mutant form of the RAS2 gene analogous to an oncogenic mutant of the human HRAS gene. A cDNA so cloned and designated DPD (rat dunce-like phosphodiesterase) has the capacity to complement or "rescue" the loss of growth control associated with an activated RAS2$^{va119}$ gene harbored in yeast strain TK161-R2V (A.T.C.C. 74050), as well as the analogous defective growth control phenotype of the yeast mutant 10DAB (A.T.C.C. 74049) which is defective at both yeast PDE gene loci (pde$^{-1}$, pde$^{-2}$). The gene encodes a high-affinity cAMP specific phosphodiesterase, the amino acid sequence of which is highly homologous to the cAMP-specific phosphodiesterase encoded by the dunce locus of Drosophila melanogaster.

Through the date of filing of parent application Ser. No. 07/688,356, there have been no reports of the cloning and expression of DNA sequences encoding any of the mammalian Ca$^{2+}$/calmodulin stimulated or cGMP-stimulated PDEs (PDE families I and II) and, accordingly, there continues to exist a need in the art for complete nucleotide sequence information for these PDEs.

BRIEF SUMMARY OF THE INVENTION

The present invention provides novel purified and isolated polynucleotide sequences (e.g. DNA and RNA including sense and antisense strands) which code for expression of mammalian species (e.g., human and bovine) Ca$^{2+}$/calmodulin stimulated cyclic nucleotide phosphodiesterase and cGMP stimulated cyclic nucleotide phosphodiesterase polypeptides. Genomic and cDNA sequences provided by the invention may be associated with homologous or heterologous species expression control DNA sequences such as promoters, operators, regulators, terminators and the like to allow for in vivo and in vitro transcription to messenger RNA and, in turn, translation of mRNAs to provide functional phosphodiesterases and related polypeptides in large quantities.

Specifically provided by the invention are mammalian DNA sequences encoding phosphodiesterases and fragments thereof which are present as mammalian DNA inserts in bacterial plasmids and viral vectors which are the subject of deposits made with the American Type Culture Collection, 12301 Parklawn Drive, Rockville, Md. 20852 on Apr. 11 and 15, 1991 and on Apr. 14, 1992 in accordance with U.S. Patent and Trademark Office and Budapest Treaty requirements. DNAs deposited in connection with the present invention include:

1. Plasmid pCAM-40 in *E. coli* (A.T.C.C. accession No. 68576) containing a bovine brain cDNA insert encoding a 61 kDa CaM-PDE isozyme;

2. Plasmid p12.3A in *E. coli* (A.T.C.C. 68577) containing a bovine brain cDNA insert encoding a 63 kDa CaM-PDE isozyme;

3. Bacteriophage λ CaM H6a (A.T.C.C. accession No. 75000) containing a human hippocampus cDNA insert fractionally encoding a 61 kDa CaM-PDE isozyme;

4. Plasmid pHcam61-6N-7 in *E. coli* (A.T.C.C. accession No. 68963) containing a composite human cDNA insert encoding a 61 kDa CaM-PDE isozyme;

5. Plasmid pcamH3EF in *E. coli* (A.T.C.C. accession No. 68964) containing a human hippocampus cDNA insert encoding a novel PDE homologous to a 61 kDa CaM-PDE;

6. Plasmid pcamHella in *E. coli* (A.T.C.C. accession No. 68965) containing a human heart cDNA insert encoding a novel PDE homologous to a 61 kDa CaM-PDE;

7. Plasmid p3CGS-5 in *E. coli* (A.T.C.C. accession No. 68579) containing a bovine adrenal cDNA insert encoding a cGS-PDE isozyme;

8. Plasmid pBBCGSPDE-5 in *E. coli* (A.T.C.C. accession No. 68578) containing a bovine brain cDNA insert encoding a cGS-PDE isozyme fragment;

9. Plasmid pBBCGSPDE-7 in *E. coli* (A.T.C.C. accession No. 68580) containing a bovine brain cDNA encoding a cGS-PDE isozyme;

10. Plasmid pGSPDE6.1 in *E. coli* (A.T.C.C. accession No. 68583) containing a human heart cDNA encoding a cGS-PDE isozyme fragment;

11. Plasmid pGSPDE7.1 in *E. coli* (A.T.C.C. accession No. 68585) containing a human hippocampus cDNA insert encoding a cGS-PDE isozyme fragment; and 12. Plasmid pGSPDE9.2 (A.T.C.C. accession No. 68584) containing a human hippocampus cDNA insert encoding a cGS-PDE isozyme fragment. 13. Plasmid pHcgs6n in *E. coli* (A.T.C.C. accession No. 68962) containing a human cDNA insert encoding a cGS-PDE.

Also specifically provided by the present invention is a bovine cDNA sequence containing nucleotides encoding bovine 59 kDa CaM-PDE and characterized by the DNA and amino acid sequences of SEQ ID NO: 16 and SEQ ID NO: 17.

In related embodiments, the invention concerns DNA constructs which comprise a transcriptional promoter, a DNA sequence which encodes the PDE or a fragment thereof, and a transcriptional terminator, each operably linked for expression of the enzyme or enzyme fragment. The constructs are preferably used to transform or transfect host cells, preferably eukaryotic cells, and more preferably mammalian or yeast cells. For large scale production, the expressed PDE can be isolated from the cells by, for example, immunoaffinity purification.

Incorporation of DNA sequences into procaryotic and eucaryotic host cells by standard transformation and transfection processes, potentially involving suitable DNA and RNA viral vectors and circular DNA plasmid vectors, is also within the contemplation of the invention and is expected to provide useful proteins in quantities heretofore unavailable from natural sources. Systems provided by the invention include transformed *E. coli* cells, including those referred to above, as well as other transformed eukaryotic cells, including yeast and mammalian cells. Use of mammalian host cells is expected to provide for such post-translational modifications (e.g., truncation, lipidation, and tyrosine, serine or threonine phosphorylation) as may be needed to confer optimal biological activity on recombinant expression products of the invention.

Novel protein products of the invention include expression products of the aforementioned nucleic acid sequences and polypeptides having the primary structural conformation (i.e., amino acid sequence) of CaM-PDE and cGS-PDE proteins, as well as peptide fragments thereof and synthetic peptides assembled to be duplicative of amino acid sequences thereof. Proteins, protein fragments, and synthetic peptides of the invention are projected to have numerous uses including therapeutic, diagnostic, and prognostic uses and will provide the basis for preparation of monoclonal and polyclonal antibodies specifically immunoreactive with the proteins of the invention.

Also provided by the present invention are antibody substances (including polyclonal and monoclonal antibodies, chimeric antibodies, single chain antibodies and the like) characterized by their ability to bind with high immunospecificity to the proteins of the invention and to their fragments and peptides, recognizing unique epitopes which are not common to other proteins. The monoclonal antibodies of the invention can be used for affinity purification of CaM-PDEs and cGS-PDEs, e.g., Hansen et al., *Meth. Enzymol.*, 159:543 (1988).

Also provided by the present invention are novel procedures for the detection and/or quantification of normal, abnormal, or mutated forms of CaM-PDEs and cGS-PDEs, as well as nucleic acids (e.g., DNA and mRNA) associated therewith. Illustratively, antibodies of the invention may be employed in known immunological procedures for quantitative detection of these proteins in fluid and tissue sample, and of DNA sequences of the invention that may be suitably labelled and employed for quantitative detection of mRNA encoding these proteins.

Among the multiple aspects of the present invention, therefore, is the provision of (a) novel CaM-PDE and cGS-PDE encoding polynucleotide sequences, (b) polynucleotide sequences encoding polypeptides having the activity of a mammalian CaM-PDE or of a mammalian cGS-PDE which hybridize to the novel CaM-PDE and cGS-PDE encoding sequences under hybridization conditions of the stringency equal to or greater than the conditions described herein and employed in the initial isolation of cDNAs of the invention, and (c) polynucleotide sequences encoding the same (or allelic variant or analog polypeptides) through use of, at least in part, degenerate codons. Correspondingly provided are viral DNA and RNA vectors or circular plasmid DNA vectors incorporating polynucleotide sequences and procaryotic and eucaryotic host cells transformed or transfected with such polynucleotide sequences and vectors, as well as novel methods for the recombinant production of these proteins through cultured growth of such hosts and isolation of the expressed proteins from the hosts or their culture media.

In yet other embodiments, the invention provides compositions and methods for identifying compounds which can modulate PDE activity. Such methods comprise incubating a compound to be evaluated for PDE modulating activity with eukaryotic cells which express a recombinant PDE polypeptide and determining therefrom the effect of the compound on the phosphodiesterase activity provided by gene expression. The method is effective with either whole cells or cell lysate preparations. In a preferred embodiment, the eukaryotic cell is a yeast cell or mammalian cell which lacks endogenous phosphodiesterase activity. The effect of the compound on phosphodiesterase activity can be determined by means of biochemical assays which monitor the hydrolysis of cAMP and/or cGMP, or by following the effect of the compound on the alteration of a phenotypic trait of the eukaryotic cell associated with the presence or absence of the recombinant PDE polypeptide.

Other aspects and advantages of the present invention will be apparent upon consideration of the following detailed description thereof which includes numerous illustrative examples of the practice of the invention, reference being made to the drawing wherein:

FIG. 1 provides the results of amino acid sequence determinations for isolated 59 kDa (bovine heart) and 63 kDa (bovine brain) CaM-PDE proteins in alignment with the complete sequence of the 61 kDa (bovine brain) isozyme. Identities of the 59 and 63 kDa proteins to the 61 kDa isozyme are underlined. Tentative identifications are in lower cases and hyphens denote unidentified residues. The N-terminus of the 59 kDa isozyme, as determined by the subtraction of a methionyl peptide (mDDHVTIRRK) from the composition of an amino-terminal blocked lysyl peptide, is in parenthesis. Solid boxes are placed above residues within the CaM-binding sites identified in the 61 and 59 kDa isozymes.

DETAILED DESCRIPTION OF THE INVENTION

Figure 1A:
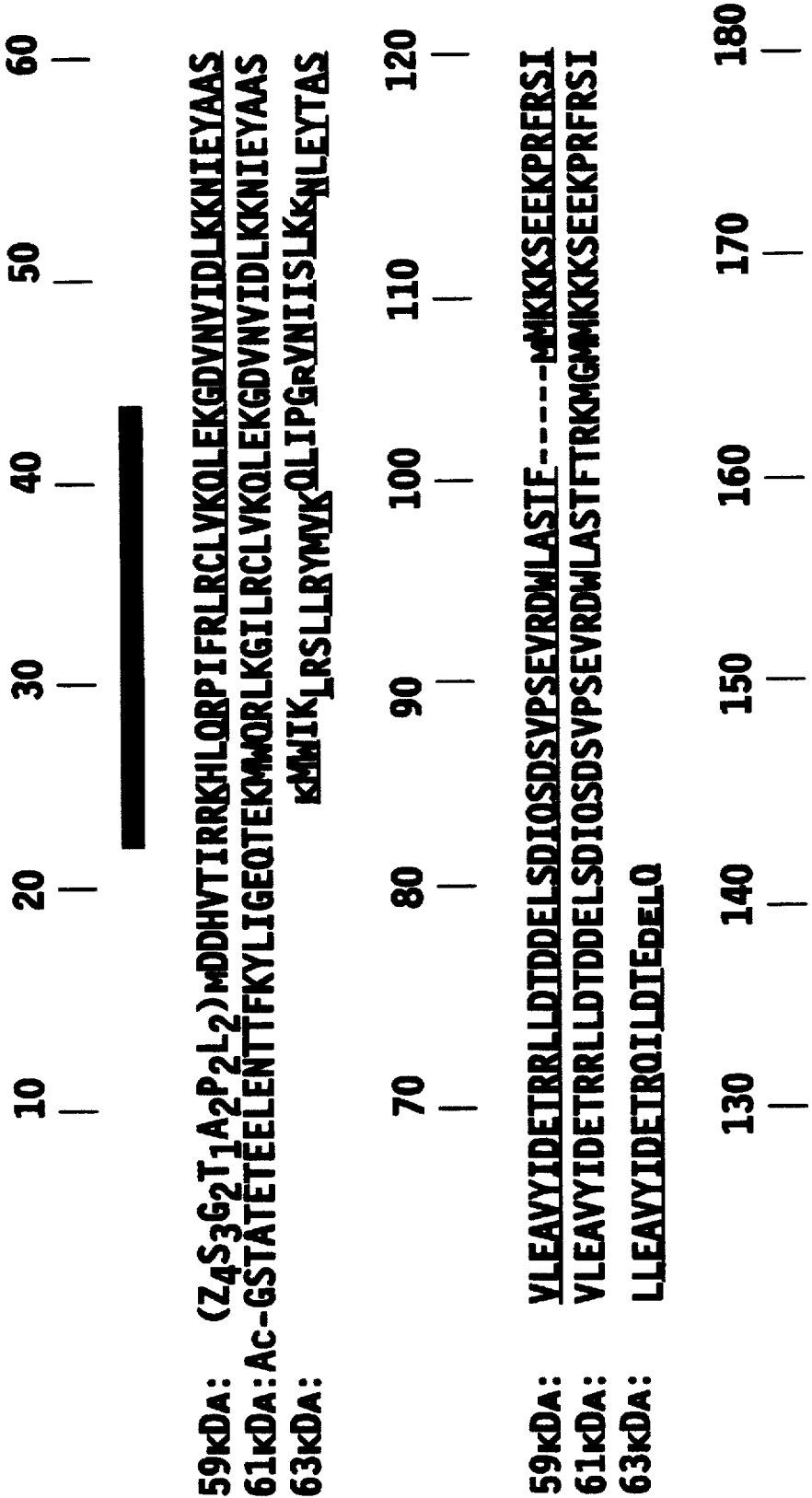

The following examples illustrate practice of the invention. Example I relates to the isolation, purification, and sequence determination of 61 kDa CaM-PDE cDNA from bovine brain and to the expression thereof in a mammalian host cell. Example II relates to the isolation, purification, and sequence determination of a 59 kDa CaM-PDE from bovine lung and to the expression thereof in a mammalian host cell. Example III relates to the isolation, purification, and sequence determination of 63 kDa CaM-PDE cDNA from bovine brain and to the expression thereof in a mammalian host cell. Example IV relates to the isolation, purification, and sequence determination of CGS-PDE cDNA from bovine adrenal cortex, as well as the expression of the DNA in mammalian host cells. Example V relates to the isolation, purification, and sequence determination of cGS-PDE cDNA from bovine brain and to the expression thereof in a mammalian host cell. Example VI relates to the use of CGS-PDE bovine adrenal cDNA to obtain human cGS-PDE cDNAs and to the development of a human cDNA encoding a cGS-PDE. Example VII relates to the use of CaM-PDE 61 kDa bovine brain cDNA to obtain a human CaM-PDE 61 kDa cDNA and a novel structurally related cDNA. Example VIII relates to the expression of bovine and human PDE cDNAs for complementation of yeast phenotypic defects and verification of phosphodiesterase activity for the expression product. Example IX relates to tissue expression studies involving Northern analysis and RNase protection studies employing polynucleotides (specifically cDNAs and antisense RNAs) of the invention.

In those portions of the text addressing the formation of redundant oliqonucleotides, the following Table I single letter code recommendations for ambiguous nucleotide sequence, as reported in *J.Biol.Chem.*, 261:13–17 (1986), are employed:

TABLE I

| Symbol | Meaning | Origin of designation |
|---|---|---|
| G | G | Guanine |
| A | A | Adenine |
| T | T | Thymine |
| C | C | Cytosine |
| R | G or A | puRine |
| Y | T or C | pYrimidine |
| M | A or C | aMino |
| K | G or T | Keto |
| S | G or C | Strong interaction (3 H bonds) |
| W | A or T | Weak interaction (2 H bonds) |
| H | A, C, or T | not G, as H follows G in the alphabet |
| B | G, C, or T | not A |
| V | A, C, or G | not T, (not U) as V follows U |
| D | A, G, or T | not C |
| N | A, C, G, or T | any Nucleotide base |

EXAMPLE I

Isolation, Purification, and Sequence Determination of 61 kDa CaM-PDE cDNA From Bovine Brain In this Example, a cDNA sequence representing that portion of a gene for 61 kDa bovine brain CaM-PDE which encodes the amino terminus of the protein was isolated by PCR from a collection of first strand cDNAs developed from bovine brain mRNA. The PCR-generated fragment was then employed to isolate a full length bovine brain CaM-PDE sequence.

Total RNA was prepared from bovine heart using the method of Chomczynski et al., *Anal.Biochem.*, 162:156–159 (1987) and mRNA was selected using a Poly(A) QuikTm mRNA purification kit according to the manufacturer's protocol. First strand cDNA was synthesized by adding 80 units of AMV reverse transcriptase to a reaction mixture (40 µl, final volume) containing 50 mM Tris HCl (pH8.3@ 42°), 10 mM MgCl$_2$, 10 mM dithiothreitol, 0.5 mM (each) deoxynucleotide triphosphates, 50 mM KCl, 2.5 mM sodium pyrophosphate, 5 µg deoxythymidylic acid oligomers (12–18 bases) and 5 µg bovine heart mRNA denatured for 15 min at 65°. Incorporation of 1 µl [$^{32}$P]-labeled dCTP (3000 Ci/mmol) was used to quantitate first strand cDNA synthesis. The reaction was incubated at 42° for 60 min. The reaction was phenol/CHCl$_3$ extracted and EtOH precipitated. The nucleic acid pellet was resuspended in 50 µl of 10 mM Tris-HCl (pH 7.5)/0.1 mM EDTA to a final concentration of 15 ng per µl.

Redundant sense and antisense oligomers corresponding to 61 kDa peptide sequences as in FIG. 1 were designed to be minimally redundant, yet long enough to specifically hybridize to the target template.

A first 23 base oligomer, designated CaM PCR-2S, was synthesized on an Applied Biosystems, Inc. DNA synthesizer. The oligomer had the following sequence,

SEQ ID NO: 1

5'-AARATGGGNATGAARAARAA-3' which specifies the following amino acid sequence,

SEQ ID NO: 2

KMGMMKKK.

A second 23 base oligomer, designated CaM PCR-3AS, was synthesized with the following sequence,

SEQ ID NO: 3

5'-ACRTTCATYTCYTCYTCYTGCAT-3' representing the following amino acid sequence,

SEQ ID NO: 4

MQEEEMNV.

A 612 bp CaM PDE cDNA fragment was synthesized using the PCR amplification technique by adding 15 ng of first strand cDNA to a reaction mixture containing 50 mM KCl, 10 mM Tris-HCl (pH 9.0), 1.5 mM $MgCl_2$, 0.01% gelatin, 0.1% Triton X-100, 0.2 mM (each) deoxynucleotide triphosphates, 1 µM (each) CaM PCR 2S and CaM PCR-3AS oligomers, and 2.5 units of *Thermus aquaticus* DNA polymerase. The reaction was incubated for 30 cycles as follows: 94° for 1 min; 50° for 2 min; and 72° for 2 min. The reaction products were purified on a 1% agarose gel using 0.04M Tris-acetate/0.001M EDTA buffer containing 0.5 µg/ml ethidium bromide. The DNA products were visualized with UV light, cleanly excised from the gel with a razor blade, purified using Geneclean II reagent kit and ligated into Eco RV-cut pBluescript vector DNA.

To determine if the PCR amplification products were CaM PDE cDNAs, the subcloned PCR DNA products were sequenced from the ends using T3 and T7 promoter primers and either Sequenase or Taq Polymerase sequencing kits. Approximately 250 bases from each end of this piece of DNA were sequenced and the deduced amino acid sequence from the cDNA corresponded with the FIGS. 1A–1C amino acid sequences of the 59 and 61 kDa CaM-PDEs, confirming that the PCR DNA product was a partial CaM PDE cDNA.

A bovine brain cDNA library constructed with the lambda ZAP vector (kindly provided by Ronald E. Diehl, Merck, Sharp & Dohme) was screened with the radiolabeled 615 bp CaM-PDE cDNA obtained by PCR amplification. The probe was prepared using the method of Feinberg et al., *Anal.Biochem.*, 137:266–267 (1984), and the [$^{32}$P]-labeled DNA was purified using Elutip-D® columns. Plaques (700,000 plaques on 12–150 mm plates) bound to filter circles were hybridized at 42° C. overnight in a solution containing 50% formamide, 20 mM Tris-HCl (pH 7.5), 1X Denhardt's solution, 10% dextran sulfate, 0.1% SDS and $10^6$ cpm/ml [$^{32}$P]-labeled probe ($10^9$ cpm/µg). The filters were washed three times for 15 min with 2X SSC/0.1% SDS at room temperature, followed by two 15-min washes with 0.1X SSC/0.1% SDS at 45° C. The filters were exposed to x-ray film overnight.

Of the fifty-six plaques that hybridized with the [$^{32}$P]-labeled probes eight randomly selected clones were purified by several rounds of re-plating and screening [Maniatis et al., *Molecular Cloning: A Laboratory Manual* 545 pp. Cold Spring Harbor Laboratory, Cold Spring Harbor, N.Y., (1982)] and the insert cDNA's were subcloned into pBluescript SK(–) by in vivo excision [Short et al., *Nuc. Acids Res.*, 16:7583–7599 (1988)] as recommended by the manufacturer.

Plasmid DNA prepared from cultures of each clone were subjected to restriction analysis using EcoRI. Two clones of a suitable length were selected for sequence analysis using Taq Tak® and Sequenase® sequencing kits. The two clones were pCAM-40 (2.3 kb) and pCAM-34 (2.7 kb). The sequencing information from this procedure confirmed that the insert of pCAM-40 encoded the full length bovine brain 61 kDa CaM-PDE. The sequence of this clone and the amino acid sequence deduced therefrom are set forth in SEQ ID NO: 5 and SEQ ID NO: 6.

Transient expression of the 61 kDa CaM-PDE cDNA in COS-7 cells (A.T.C.C. CRL 1651) was accomplished as follows. Vector pCDM8 [Seed, *Nature*, 329:840–843 (1987)] in *E. coli* host cells MC1061-p3 was generously provided by Dr. Brian Seed, Massachusetts General Hospital, Boston, Mass. This vector is also available from Invitrogen, Inc. (San Diego, Calif.). Plasmid pCAM-40 was digested with HindIII and NotI, yielding a 2.3 kb fragment which was ligated into CDM8 vector DNA which had been digested with HindIII and NotI. The resulting plasmid was propagated in MC1061-p3 cells. Plasmid DNA was prepared using the alkaline lysis method of Ausubel et al., eds., *Current Protocols in Molecular Biology*, 1:1.7.1 (John Wiley & Sons, New York, 1989) and purified using Qiagen-Tip 500 columns (Qiagen, Inc. Chatsworth, Calif.) according to the manufacturer protocol.

COS-7 cells were transfected with the p-CAM-40/CDM8 construct (or mock transfected with the CDM8 vector alone) using the DEAE-dextran method Ausubel et al., supra at 1:9.2 et seq. Specifically, 10 µg of ethanol precipitated DNA was resuspended in 80 µl TBS buffer, and added to 160 µl of 10 mg per ml DEAE-dextran dropwise to a 100 mm plate of 50% confluent COS-7 cells in 4 ml of DMEM supplemented with 10% NuSerum, and mixed by swirling. The cells were incubated for 3–4 hours at 37° in a water-saturated 7% $CO_2$ atmosphere. The medium was removed and the cells were immediately treated with 10% DMSO in PBS for 1 minute. Following this treatment, the cells were washed with PBS, then DMEM, and finally cultured in DMEM supplemented with 10% fetal bovine serum and antibiotics (50 µg/ml streptomycin sulfate) in a 7%-$CO_2$ incubator for 36 hours.

COS cells were scraped from the plates and homogenized in a buffer containing 40 mM Tris-HCl (pH=7.5), 5 mM EDTA, 15 mM benzamidine, 15 mM beta-mercaptoethanol, 1 µg per ml pepstatin A and 1 µg per ml peupeptin using a Dounce homogenizer (1 ml per 100 mm plate). Homogenates were assayed for PDE activity according to the procedures of Hanson et al., *Proc. Nat'l. Acad. Sci., U.S.A.*, 79:2788–2792 (1982), using [$^3$H]cGMP as the substrate. Reactions were carried out at 30° for 10 minutes in a buffer containing 20 mM Tris-HCl (pH=7.5), 20 mM imidazole (pH=7.5), 3 mM $MgCl_2$, 15 mM µg acetate, 0.2 mg per ml BSA and 1 µM $^3$H-cAMP with either 2 mM EGTA or 0.2 mM $CaCl_2$ and 4 µg per ml CaM. Assays were stopped by incubating the tubes in a 90° water bath for 1 minute. After cooling, 10 µl of 2.5 mg per ml snake venom was added to each assay and incubated at 37° for 5 minutes. The samples were diluted with 250 µl of 20 mM Tris-HCl (pH=7.5) and immediately applied to 0.7 ml A-25 ion exchange columns. The columns were washed three times with 0.5 ml of 20 mM Tris-HCl (pH=7.5) and the eluate was collected in scintillation vials. Samples were counted for 1 minute using a Packard Model 1600TR scintillation counter. Specific cyclic nucleotide hydrolytic activity was expressed as picomoles cAMP or cGMP hydrolyzed per minute per mg protein. Protein concentration was estimated according to the method of Bradford, *Anal. Biochem.*, 72:248–254 (1976), using BSA as a standard. When compared to mock transfected cells, extracts of cells transfected with pCAM-40 cDNA contained significantly greater cAMP and cGMP hydrolytic activities in the presence of EGTA. Assays of the pCAM-40 cDNA-transfected cells in the presence of calcium and CaM resulted in stimulation of cAMP and cGMP hydrolysis.

EXAMPLE II
Isolation, Purification, and Sequence Determination of a 59 kDa CaM-PDE From Bovine Lung A fully degenerate sense oligonucleotide corresponding to the amino acid sequence

SEQ ID NO: 7

MDDHVTI from the bovine heart 59 kDa CaM-pde was synthesized. The nucleotide sequence of this oligonucleotide is

SEQ ID NO: 8

5'-ATGAGRAGRCAYGTHACNAT-3'.

An antisense oligonucleotide was designed from the FIGS.1A–1C sequence of bovine brain 61 kDa CaM-PDE, corresponding to the amino acid sequence

SEQ ID NO: 9

LRCLVKQ and having the sequence,

SEQ ID NO: 10

5'-CTGCTTCACTAAGCATCTTAG-3'.

This primer pair was used to prime a PCR reaction using bovine heart first strand cDNA (as prepared in Example I) as a template. This predicted a PCR product of 75 bp, 54 bp of which were unique 59 kDa sequence and 21 bp of which were shared between the 59 kDa and 61 kDa isozymes. The PCR products were analyzed by sieving agarose gel electrophoresis, and a band migrating at 75 bp was excised from the gel. The DNA was subcloned into pBluescript KS+, and colonies positive by the blue/white selection scheme were screened by PCR using primers directed against vector sequences. Colonies with inserts of the appropriate size were selected, and one of these (pCaM59/75.14) was chosen for sequencing. Plasmid DNA was prepared using a Qiagen P20 push column and used as template for sequencing using the dideoxy method. The sequence of the PCR product is

SEQ ID NO: 11

5' - ATGAGAAGGCACGTAACGATCAGGAGGAAACATCTCCAA AGACCCATCTTT- AGACTAAGATGCTTAGTGAAGCAG-3'.

Analysis of the sequence revealed differences in two codons between the sequence obtained and the predicted sequence. Re-examination of the sense oligonucleotide primer sequence revealed that an inadvertent transposition of two codons had led to a mistake in the design of the oligonucleotide. A second set of oligonucleotide PCR primers was prepared which predicted a 54 bp product with minimum overlap between the 59 and 61 kDa isozymes; in addition, the second sense primer incorporated a correction of the mistake in the design of the original sense primer. The sense oligonucleotide had the sequence

SEQ ID NO: 12

5'-ATGGAYGAYCACGTAACGATC-3' and the antisense oligonucleotide had the sequence

SEQ ID NO: 13

5'-AAGTATCTCATTGGAGAACAG-3'

This primer pair was used to prime a PCR reaction using bovine heart first-strand cDNA as template and the PCR products subcloned and screened exactly as described above. Two clones (pCaM59/54.9 and pCaM59/54.10) were selected for sequencing based on insert size and sequenced as described above; both clones contained 54 bp inserts of the predicted sequence

SEQ ID NO: 14

5'-ATGGATGATCACGTAACGATCAGGAGGAAACATCTCCAAA GACCCATCT- TTAGA-3', predicting the amino acid sequence

SEQ ID NO: 15

MDDHVTIRRKHLQRPIFR

A cDNA library was constructed from bovine lung mRNA and screened using procedures as described in Example IV, infra, with respect to screening of a bovine adrenal cortex library. Approximately $1.2 \times 10^6$ plaque-forming units were probed with a $^{32}$P-labelled, 1.6 kb EcoRI restriction endonuclease-cleavage product of the pCAM-40 cDNA. This initial screening produced 4 putative 59 kDA CaM-PDE cDNA clones. Preliminary sequence analysis indicated that one clone, designated p59KCAMPDE-2, contained the complete coding sequence of the putative 59 kDa CaM-PDE. A series of nested deletions were constructed from the p59KCAMPDE-2 plasmid [See, Sonnenburg et al., *J. Biol. Chem.*, 266 (26): 17655–17661 (1991)], and the resultant templates were sequenced by an adaptation of the method of Sanger using the Taq DyeDeoxy™ Terminator Cycle Sequencing Kit and an Applied Biosystems Model 373A DNA Sequencing System. The DNA and deduced amino acid sequences are set out in SEQ. ID NO: 16 and 17, respectively. A large open reading frame within the cDNA encodes a 515 residue polypeptide with an estimated molecular weight of ≅59 kilodaltons that is nearly identical to the 61 kDa CaM-PDE amino acid sequence except for the amino-terminal 18 residues. Moreover, the predicted amino acid sequence of the p59KCAMPDE-2 open reading frame is identical to the available sequence of the 59 kDa CaM-PDE purified from bovine heart, Novack et al., *Biochemistry*, 30:7940–7947 (1991). These results indicate that the p59KCAMPDE-2 cDNA represents an mRNA species encoding the 59 kDa CaM-PDE.

Transient expression of the 59 kDa bovine lung PDE was accomplished as in Example I. Specifically, a 2.66 kb, EcoRI/blunt-ended fragment of p59KCAMPDE-2 cDNA was subcloned into pCDM8 which had been digested with XhoI and blunt-ended. The recombinant plasmid, designated p59KCAMPDE-2/CDM[8 was used to transiently transfect COS-7 cells and extracts prepared from transfected COS-7 cells were assayed for CaM-PDE activity using 2 µM cAMP. COS-7 cells transfected with the p59KCAMPDE-2 cDNA yielded a cAMP hydrolytic activity that was stimulated 4–5 fold in the presence of calcium and calmodulin. Mock transfected COS-7 cells had no detectable calmodulin-stimulated cAMP hydrolytic activity.

EXAMPLE III
Isolation, Purification, and Sequence Determination of 63 kDa CaM-PDE cDNA From Bovine Brain Multiple fully and partially redundant oligonucleotides corresponding to the amino acid sequence reported in FIGS.1A–1C were synthesized for use in attempting to obtain a cDNA clone for the 63 kDa CaM-PDE. Annealing temperatures used for the polymerase chain reactions were varied between 2° to 20° C. below the theoretical melting temperature for the lowest melting oligonucleotide of each sense-antisense pair. Except for probes 63-12s and 63-13a, which are discussed below, the PCR products of each of the oligonucleotide pairs under a wide range of conditions gave multiple ethidium bromide bands when agarose gel-electrophoresed. Use of 63-12s and 63-13a resulted in a PCR product that coded for 63 kDa CaM-PDE when sequenced.

A fully redundant sense 23-mer oligonucleotide, designated 63-12s, was assembled having the following sequence

SEQ ID NO: 18

5'ATHCAYGAYTAYGARCAYACNGG-3' based on an amino acid sequence,

SEQ ID NO: 19

IHDYEHTG which is conserved in the 61 kDa bovine CaM-PDEs (see FIGS. 1A–1C. A partially redundant antisense 32-mer oligonucleotide, designated. 63-13a, had the sequence

SEQ ID NO: 20

5'-TCYTTRTCNCCYTGNCGRAARAAYTCYTCCAT-3' and was based on the following conserved sequence in the 63 kDa CaM-PDE,

SEQ ID NO: 21

MEEFFRQGDKE

Messenger RNA was prepared from bovine brain cerebral cortex and poly A⁺ selected. First strand complementary DNA was produced using AMV or MMLV reverse transcriptase. De-tritylated oligonucleotides were phosphorylated using 1 mM $\gamma$-$^{32}$P]ATP at 1×10$^6$ cpm/nmol and T4 polynucleotide kinase. After separation of 5' $^{32}$p-labelled oligonucleotides from free ATP using NENsorb 20 columns, each was suspended as a 20 µM (5' phosphate) stock and combined finally at 400 nM each in the PCR. The reaction was run using 50 ng total cDNA and 200 µM dNTP to obtain about 1 µg of PCR product. The reaction had an initial denaturation step at 94° C. for 5 min followed by 30 cycles of 1 min 94° C. denaturation, an annealing step at 50° C. for 1 min, and a 2 min extension step at 72° C. Under the reaction conditions, a single ethidium bromide-staining band of 450 base pairs was obtained on agarose gel electrophoresis of 100 ng of the PCR product. Five µg of 5' phosphorylated PCR product was ligated to 15 ng EcoRV-cut Bluescript KS(+) plasmid using T4 DNA ligase in 5% PEG-6000 for 12 h at 21° C. Putative positives of XL 1-blue transformations were white colonies using isopropyl thiogalactoside (IPTG) and bromo- chloro- indolyl galactoside (Xgal) for chromogenic selection. Such picks were sequenced using T3 or T7 primers, dideoxynucleotide terminators, and Sequenase.

One resultant clone (p11.5B) had the nucleotide sequence and translated amino acid sequence provided in SEQ ID NO: 22 and SEQ ID NO: 23, respectively. The codons for the amino acids YEH found in oligonucleotide 63-12s were replaced by codons for the amino acid sequence NTR in p11.5B. This was probably due to a contaminant in 63-12s. Since the translated open reading frame (ORF) was similar to that reported in FIGS. 1A–1C for the 63 kDa CaM PDE, p11.5B was used to screen a bovine brain cDNA library for a full length cDNA clone.

A bovine brain cDNA library was constructed in λ ZAP II. First strand cDNA was treated with RNase H, *E. coli* DNA polymerase, and *E. coli* DNA ligase to synthesize second strand cDNA. The cDNA was blunt-ended by T4-DNA polymerase; EcoRI sites in the cDNA were protected with EcoRI methylase and S-adenosyl methionine and EcoRI linkers were ligated on with T4 DNA ligase. After EcoRI restriction endonuclease treatment, free linkers were separated from the cDNA by gel filtration over Sepharose CL-4B. λ ZAP II arms were ligated onto the cDNA and packaged by an in vitro Gigapack Gold packaging kit obtained from Stratagene. 9.5×10$^5$ recombinants were obtained with 5.8% nonrecombinant plaques as assessed by plating with IPTG and X-gal. The library was amplified once by the plate lysate method to obtain 1.4×10$^7$ pfu/mL.

An initial screen of a total bovine brain cDNA library in λ ZAP II was performed. 700,000 pfu were screened using $^{32}$P-labelled oligonucleotide 63-1s at a hybridization and wash temperature of 40° C. Oligonucleotide 63-1s was it fully redundant 23-mer having the sequence

SEQ ID NO: 24

5'-AARAARAAYYTNGARTAYACNGC-3' corresponding to the amino acid sequence

SEQ ID NO: 25

KKNLEYTA

A total of 21 putative positives were picked. Subsequent rescreens were impeded by the very high background found using this screening method. Therefore, aliquots of each primary pick were pooled and 50,000 pfu of the pool were replated and rescreened with p11.5B radiolabelled by random primers and [α-$^{32}$p]dCTP. One positive was obtained, plaque-purified, and rescued as a plasmid p12.3a. Its DNA sequence is provided in SEQ ID NO: 26. Subsequently, the bovine brain cerebral cortex library was screened further with p11.5B. Two further independent clones, p12.27.9 and p12.27.11, were obtained out of a primary screen of 1.4×10$^6$ pfu. They were plaque-purified and rescued for sequencing.

Clone p12.3a coders for a protein sequence with most of the aligned peptides isolated from bovine 63 kDa CaM-PDE as shown in FIGS. 1A–1C SEQ ID NO: 26 and SEQ ID NO: 27 set forth the coding region (i.e., the 1844 nucleotides of an approximately 2.5 kilobase insert) of p12.3a. Base numbers 248–290 code for amino acid sequence

SEQ ID NO: 28

QLENGEVNIEELKK, while the comparable (FIGS. 1A–1C) peptide has the sequence

SEQ ID NO: 29

QLIPGRVNIISLKK

Base numbers 942–990 code for an amino acid sequence

SEQ ID NO: 30

KSECAILYNDRSVLEN while the isolated (FIGS.1A–1C) peptide sequence is

SEQ ID NO: 31

KDETAILYNDRTVLEN.

None of the nonaligned 63 kDa peptide sequence is found in any reading frame of p12.3a; also, the molecular weight of the p12.3a open reading frame, as translated, is 60,951 not 63,000. Therefore, this cDNA may represent an isozyme variant of the 63 kDa protein. The other two independent clones (p12.27.9 and p12.27.11) seem to have ORF sequence identical to p12.3a. The open reading frame of one clone begins at nucleotide number 823 of p12.3a and is identical to p12.3a through its termination codon. The other clone starts at nucleotide 198 and is identical to p12.3a throughout its length. None of the three clones has the anomalous NTR peptide sequence found in p11.5B; all three have YEH as the 61 kDa CaM PDE.

Transient expression of the 63kDa CaM-PDE cDNA in COS-7 cells was accomplished as follows. A fragment of the cDNA insert of plasmid p 12.3 including the protein coding region of SEQ.ID NO: 26 and flanked by BamHI restriction sites was; prepared by PCR. More specifically, oligonucleotides corresponding to base Nos. 94–117 (with the putative initiation codon) and the antisense of base Nos. 1719–1735 (with sequence immediately 3' of the termination codon) of SEQ.ID NO. 26 were synthesized with two tandem BamHI sites on their 5' ends. The two primers had the following sequences:

SEQ. ID NO: 32

5'-GGATCCGGATCCCGCAGACGGAGGCTGAGCATGG-3'

SEQ. ID NO: 33

5'-GGATCCGGATCCAGGACCTGGCCAGGCCCGGC-3'

The two oligonucleotides were used in a PCR cycling 30 times from a 1 min incubation at 94° C. to a 2 min 72° C. incubation with a final 10 min extension reaction at 72° C. The 100 µl reaction used 20 µM of each oligonucleotide and 100 pg p12.3a as the template in order to produce 5 µg 1665 base pair product.

The product was extracted once with an equal volume of 1:1 phenol:chloroform, made 0.3 M with regard to sodium acetate, and precipitated with two volumes of ethanol overnight. The precipitate was dried, rehydrated into 50 µl, and the cDNA was digested with 5 units BamHI restriction endonuclease for one hour at 37° C. Afterwards, the solution was extracted once with an equal volume of 1:1 phenol:chloroform. The 1641 base pair cDNA with BamHI 5' and 3' ends was purified from the aqueous layer using Qiagen Q-20 columns (Qiagen, Inc., Chatsworth, Calif.) and the protocol given by the manufacturer.

The cut, purified PCR product was ligated into BamHI digested, alkaline phosphatase-treated Bluescript KS(+) plasmid. The ligation product was subcloned into XL1 cells; resulting transformants were screened by sequencing. One transformant (designated p11.6.c6) was isolated with the BamHI insert oriented such that the Bluescript KS(+) HindIII restriction site was 30 bases 5' to the sequence of the insert encoding the initiation codon. This plasmid was digested with HindIII and XbaI restriction endonucleases to release the 1689 base pair fragment. The fragment was ligated into HindIII- and XbaI-digested CDM8 vector DNA as in Example I.

COS-7 cells were transfected with the p12.3.a/CDM8 construct or mock transfected with the CDM8 vector alone using the DEAE-dextran method as described in Example 1. A ratio of 10 µg DNA/400 µg DEAE-dextran was used, with a final DEAE-dextran concentration in the media of 100 µg/ml. After 48 h, cells were suspended in 1 ml of homogenization buffer (40 mM Tris HCl, pH=7.5, 15 mM benzamidine HCl, 15 mM 6-mercaptoethanol, 0.7 µg/ml pepstatin A, 0.5 µg/ml leupeptin, and 5 mM Na$_4$EDTA) and disrupted on ice using a Dounce homogenizer. The homogenates were diluted ½ to make a final 50% (v/v) glycerol for storage at −20° C. and used either to assay for phosphodiesterase activity or to determine protein concentration. CaM-dependent and independent activities were determined as in Example 1. Cells transfected with a p12.3.a DNA had a 15-fold increase in CaM-stimulated cAMP phosphodiesterase activity and a 12-fold increase in CaM-stimulated cGMP phosphodiesterase activity over basal levels. Mock transfected COS-7 cells showed no PDE activity over basal levels even with CaM stimulation.

EXAMPLE IV

Isolation, Purification, sequence Determination, and Expression of cGS-PDE cDNA From Bovine Adrenal Cortex Total RNA was prepared from bovine adrenal outer cortex using the method of Chomczynski et al., supra. Polyadenylated RNA was purified from total RNA preparations using the Poly(A) QuickTm mRNA purification kit according to the manufaicturer's protocol. First strand cDNA was synthesized by adding 80 units of AMV reverse transcriptase to a reaction mixture (40 µl, final volume) containing 50 mM Tris-HCl (pH 8.3@420), 10 mM MgCl$_2$, 10 mM dithiothreitol, 0.5 mM (each) deoxynucleotide triphosphates, 50 mM KCl, 2.5 mM sodium pyrophosphate, 5 µg deoxythymidylic acid oligomers (12–18 bases) and 5 µg bovine adrenal cortex mRNA denatured for 15 min at 65° C. The reaction was incubated at 42° C. for 60 min. The second strand was synthesized using the method of Watson et al., *DNA Cloning: A Practical Approach*, 1:79–87 (1985) and the ends of the cDNA were made blunt with T4 DNA polymerase. EcoRI restriction endonuclease sites were methylated [Maniatis et al., supra] using a EcoRI methylase (Promega), and EcoRI linkers (50-fold molar excess) were ligated to the cDNA using T4 DNA ligase. Excess linkers were removed by digesting the cDNA with EcoRI restriction endonuclease, followed by Sepharose CL-4B chromatography. Ausubel et al., supra. The cDNA (25–50 ng per µg vector) was ligated into EcoRI-digested, dephosphorylated ZAP® II (Stratagene) arms [Short et al., *Nuc.Acids Res.*, 16:7583–751)9 (1988)] and packaged [Maniatis et al., supra] with Gigapack® Gold extracts according to the manufacturer's protocol.

Initially, an unamplified bovine adrenal cortex cDNA library was made and screened with a redundant 23-mer antisense oligonucleotide probes end-labeled with γ-[$^{32}$P] ATP and T4 polynucleotide kinase. The oligomers corresponding to the amino acid sequences

SEQ ID NO: 34
EMMMYHMK and

SEQ ID NO: 35
YHNWMHAF were made using an Applied Biosystems model 380A DNA synthesizer. Their sequences are as follows:

SEQ ID NO: 36
5'-TT CAT RTG RTA CAT CAT CAT YTC-3'

SEQ ID NO: 37
5'-AA NGC RTG CAT CCA RTT RTG RTA-3'

Duplicate nitrocellulose filter circles bearing plaques from 12 confluent 150 mm plates (approximately 50,000 pfu/plate) were hybridized at 45° C. overnight in a solution containing 6X SSC, 1X Denhardt's solution, 100 µg/ml yeast tRNA, 0.05% sodium pyrophosphate and $10^6$ cpm/ml radiolabeled probe (>$10^6$ cpm per pmol). The filters were washed three times in 6X SSC at room temperature, followed by a higher-stringency 6X SSC wash at 100° C. below the minimum melting temperature of the oligomer probes, and exposed to x-ray film overnight.

A single 2.1 kb cDNA clone (designated pcGS-3:2.1) was isolated and sequenced. The amino acid sequence enclosed by the large ORF of this clone was identical to peptide sequences of the cGS-PDE purified from the supernatant fraction of a bovine heart homogenate. LeTrong et al., supra.

A second, amplified, bovine adrenal cortex cDNA library was screened using the ($^{32}$P)-labeled CGS-3:2.1 partial cDNA, yielding a 4.2 kb cDNA (designated 3CGS-5).

The library was constructed, amplified as in Maniatis et al., supra, plated and screened with the bovine cDNA insert from clone CGS-3:2.1. The probe was prepared using the method of Feinberg et al., supra, and the radiolabeled DNA was purified using Elutip-D® columns. Plaques (600,000 pfu on twelve 150 mm plates) bound to filter circles were hybridized at 42° C. overnight in a solution containing 50% formamide, 20 mM Tris-HCl (pH 7.5, 1X Denhardt's solution, 10% dextran sulfate, 0.11% SDS and $10^6$ cpm/ml [$^{32}$P]-labeled probe ($10^9$ cpm/µg). The filters were washed three times for 15 minutes with 2X SSC/0.1% SDS at room temperature, followed by two 15-minute washes with 0.1X SSC/0.1% SDS at 45° C. The filters were exposed to x-ray film overnight. Ausubel et al., supra.

From this initial screening, 52 putative clones were identified. Twenty of these clones were randomly selected, purified by several rounds of re-plating and screening [Maniatis et al., supra] and the insert cDNAS were subcloned into pBluescript SK(-) by in vivo excision [Short et al., supra] as recommended by the manufacturer. Plasmid DNA prepared from these clones were analyzed by restriction analysis and/or sequencing. From this survey, a 4.2 kb cDNA representing the largest open reading frame was identified. The cDNA inserts from the other putative clones were shorter, and appeared to be identical based on the nucleotide sequence of the insert ends.

Putative CGS-PDE cDNAs were sequenced by a modification of the Sanger method [Sanger et al., Proc.Natl.Acad.Sci. USA, 74:5463–5467] using Sequenase® or Taq Trak® kits as directed by the manufacturer. Templates were prepared from the cDNAs by constructing a series of nested deletions [Henikoff, Gene, 28:351–359 (1984)] in the vector, pBluescript SK(-) (Stratagene) using exonuclease III and mung bean nuclease according to the manufacturer's protocol. In cases where overlapping templates were not attained by this method, the cDNAs were cleaved at convenient restriction endonuclease sites and subcloned into pBluescript, or specific oligomers were manufactured to prime the template for sequencing. Single-stranded DNA templates were rescued by isolating the DNA from phagemid secreted by helper phage-infected XL1 cells harboring the pBluescript plasmid [Levinson et al., supra] as recommended by the manufacturer (Stratagene). Homology searches of GENBANK (Release 66.0), EMBL (Release 25.0), and NBRF nucleic acid (Release 36.0) and protein (Release 26.0) databases were conducted using Wordsearch, FASTA and TFASTA programs supplied with the Genetics Computer Group software package Devereux et al., Nuc.Acids Res., 12:387–395 (1984).

The nucleotide sequence and deduced amino acid sequence encoded by the large open reading frame of p3CGS-5 cDNA clone insert is provided in SEQ ID NO: 38 and SEQ ID NO: 39. Starting with the first methionine codon, the cDNA encodes a 921 residue polypeptide with a calculated molecular weight of about 103,000. Although no stop codons precede this sequence, an initiator methionine consensus sequence [Kozak, J.Cell Biol., 108:229–241 (1989)] has been identified. The presence of 36 adenosine residues at the 3' end of the cDNA preceded by a transcription termination consensus sequence [Birnstiel et al., Cell, 41:349–359 (1985)] suggests that all of the 3' untranslated sequence of the cGS-PDE mRNA is represented by this clone.

A putative phosphodiesterase-deficient (PPD) strain of S49 cells [Bourne et al., J.Cell.Physiol., 85:611–620 (1975)] was transiently transfected with the cGS-PDE cDNA using the DEAE-dextran method. The cGS-PDE cDNA was ligated into the unique BamHI cloning site in a mammalian expression vector, designated pZEM 228, following a zinc-inducible metallothionine promoter and prior to an SV40 transcription termination sequence. The DNA was purified from large-scale plasmid preparations using Qiagen pack-500 columns as directed by the manufacturer. PPD-S49 cells were cultured in DMEM containing 10% heat-inactivated horse serum, 50 µg/ml penicillin G and 50 µg/ml streptomycin sulfate at 37° C. in a water-saturated 7% $CO_2$ atmosphere. Prior to transfections, confluent 100 mm dishes of cells were replated at one-fifth of the original density and incubated for 24–36 h. In a typical transfection experiment, PPD-S49 cells (50–80% confluent) were washed with Tris-buffered-saline and approximately $2\times10^7$ cells were transfected with 10 µg of DNA mixed with 400 µg of DEAE-dextran in one ml of TBS. The cells were incubated at 37° C. for 1 hr with gentle agitation every 20 min. Next, DMSO was added to a final concentration of 10% and rapidly mixed by pipetting up and down. After 2 min, the cells were diluted with 15 volumes of TBS, collected by centrifugation, and washed, consecutively with TBS and DMEM. The cells were resuspended in complete medium and seeded into fresh 100 mm plates (1–2×107 cells/10 ml/plate). After 24 h, the cells were treated with TBS alone, or containing zinc sulfate (final concentration=125 µM) and incubated for an additional 24 h. The cells were harvested and washed once with TBS. The final cell pellets were resuspended in two mls of homogenization buffer (40 mM Tris-HCl; pH 7.5, 15 mM benzamidine, 15mM β-mercaptoethanol, 0.7 µg/ml pepstatin A, 0.5 µg/ml leupeptin and 5 mM EDTA) and disrupted on ice using a dounce homogenizer. The homogenates were centrifuged at 10,000×g for 5 min at 40° C. and the supernatants were assayed for phosphodiesterase activity and protein concentration.

cGS PDE activity was determined by a previously described method using [$^3$H]cAMP as the substrate as in Martins et al., *J.Biol.Chem.*, 257:1973–1979 (1982). Phosphodiesterase assays where performed in triplicate. The Bradford assay [Bradford, *Anal. Biochem.*, 72:248–254 (1976)] was used to quantitate protein using BSA as the standard.

In the absence of zinc treatment, no increase in basal activity or cGMP-stimulated phosphodiesterase activity was detected in PPD S49 cells transfected with the cGS PDE-ZEM 228 construct or the vector alone. However, zinc-treated cells; transfected with cGS-PDE cDNA, but not the vector alone, expressed cGMP-enhanced cAMP phosphodiesterase activity indicating that the cDNA encodes a cGS-PDE. The total activity of the homogenates and 50,000×g supernatants was not significantly different.

Transient expression of the CGS-PDE cDNA in COS-7 cells was accomplished as in Example I. A 4.2 kb fragment of p3CGS-5 was isolated using HindIII and NotI and was inserted into plasmid pCDM8, which had been digested with the same enzymes. The character of products produced in COS-7 cells transformed with the p3CGS-5/pCDM8 construct is discussed in Example V, infra.

EXAMPLE V

Isolation, Purification, and Partial Sequence Determination of CGS-PDE cDNA from Bovine Brain A. Isolation of Bovine Brain cGSPDE cDNA Clone. pBBCGSPDE-5

A bovine brain cDNA library constructed with the λ ZAP vector (kindly provided by Ronald E. Diehl, Merck, Sharp & Dohme) was screened with a 450 bp EcoRI/ApaI restriction endonuclease cleavage fragment of the p3CGS-5 cDNA corresponding to (p3CGS-5) nucleotide position numbers 1–452. The probe was prepared using the method of Feinberg et al., supra, and the [$^{32}$P]-labeled DNA was purified using Elutip D® columns. Plaques (a total of 600,000 plaques con 12–150 mm plates) bound to filter circles were hybridized at 42° overnight in a solution containing 50% formamide, 20 mM Tris HCl (pH 7.5), 1X Denhardt's solution, 10% dextran sulfate, 0.1% SDS and 10$^6$ cpm/ml [$^{32}$P]-labeled probe (10$^9$ cpm/μg). The filters were washed three times for 15 minutes with 2X SSC/0.1% SDS at room temperature, followed by two 15 minute washes with 0.1X SSC/0.1% SDS at 45%. The filters were exposed to x-ray film overnight.

Forty putative clones were picked from this first screen, of which six were randomly selected and purified by several rounds of re-plating and screening [Maniatis et al., supra]. The insert cDNAs were subcloned into pBluescript SK(−) by in vivo excision as recommended by the manufacturer. Plasmid DNA prepared from cultures of each clone was sequenced from the ends using Sequenase and Taq Trak sequencing kits. The sequence obtained from this experiment confirmed that the bovine brain cDNA clone, pBBCGSPDE-5 was a CGS-PDE cDNA, and that it was different than the adrenal cGS-PDE cDNA at the five-prime end.

Partial sequence analysis of the pBBCGSPDE-5 insert at its 5' end (encoding the amino terminal region of the protein) revealed the sense strand set out in SEQ ID NO: 40, while sequencing of the 3' end of the insert revealed the antisense sequence of SEQ ID NO: 41.

B. Isolation or Bovine Brain cGS-PDE cDNL Clone, pBBCGSPDE-7

Each of the forty putative clones selected from the first round of purification described above was spotted individually onto a lawn of host XL1 cells and incubated overnight at 370, The plaques were screened with a 370 bp PstI/SmaI restriction endonuclease cleavage fragment of the p3CGS-5 cDIA (corresponding p3CGS-5 nucleotide position numbers 2661–3034). The probe was prepared using the method of Feinberg et al., supra, and the [$^{32}$P]-labeled DNA was purified using Elutip-D® columns. Plaques bound to filter circles were hybridized at 42° overnight in a solution containing 50% formamide, 20 mM Tris-HCl (pH 7.5), 1X Denhardt's solution, 10% dextran sulfate, 0.1% SDS and 10$^6$ cpm/ml ($^{32}$P)-labeled probe (10$^9$ cpm/μg). The filters were washed three times for 15 minutes with 2X SSC/0.1% SDS at room temperature, followed by two 15-minute washes with 0.1X SSC/0.1% SDS at 45°. The filters were exposed to x-ray film overnight.

After several rounds of plating and rescreening, six putative clones were purified and sequenced from the ends. The sequence of the five-prime end of the cDNA clone pBBCGSPDE-7 was identical to clone pBBCGSPDE-5, but not the adrenal gland-derived clone, p3CGS-5. The sequence of the three-prime end of the pBBCGSPDE-7 cDNA clone was identical to the p3CGS-5 insert sequence.

Sequence analysis of the pBBCGSPDE-7 insert revealed the DNA sequence set out in SEQ ID NO: 42 and the amino acid sequence of SEQ. ID NO: 43.

The large open reading frame encodes a 942-residue polypeptide that is nearly identical to the adrenal gland CGS-PDE isozyme (921 residues). The difference in the primary structure of these two isozymes lies in the amino-terminal residues 1–46 of the brain cGS-PDE, and residues 1–25 of the adrenal cGS-PDE. The remaining carboxy-terminal residues of the brain and adrenal cGS-PDE are identical.

For transient expression in COS-7 cells, a 3.8 kb fragment of pBBCGSPDE-7 was isolated using HindIII and NotI and inserted into plasmid pCDM8 which had been cut with HindIII and NotI restriction endonucleases. The recombinant pBBCGSPDE-7/CDM8 construct was used to transiently transfect COS-7 cells. The properties of the pBBCGSPDE-7/CDM8 construct and the p3CGS-5/CDM8 construct prepared in Example IV products were subsequently compared. Membrane and supernatant fractions were prepared from extracts of transfected COS-7 cells and assayed for cGS-PDE activity. Both the pBBCGSPDE-7/CDM8 and p3CGS5/CDM8 plasmid constructs produced cGS-PDE activities in COS-7 cell extracts, and most of the activity was detected in the supernatant fractions.

However, a 10-fold greater percentage of total cGS-PDE activity was detected in membranes from COS-7 cell extracts transfected with the pBBCGSPDE-7/CDM8 construct than in membranes prepared from p3CGS-5/CDM8-transfected COS-7 cells. These results indicate that, relative to the adrenal cGS-PDE, the isozyme encoded by the pBBCGSPDE-7 cDNA preferentially associates with cellular membranes.

EXAMPLE VI

Use of CGS-PDE Bovine Adrenal cDNA to Obtain Human CGS-PDE cDNAs

Several human cDNA clones, homologous to a cDNA clone encoding the bovine cyclic GMP-stimulated phosphodiesterase, were isolated by hybridization using a nucleic acid probe derived from the bovine cDNA. A combination of sequence analysis and hybridization studies indicates that these human cDNA clones encompass an open reading frame corresponding to a human phosphodiesterase.

cDNA libraries were probed with DNA from plasmid p3CGS-5 which contains a 4.2-kb cDNA insert encoding the bovine cGS-PDE. This plasmid was digested with the restriction enzymes SmaI and EcoRI. The approximately 3.0 kb fragment derived from the cDNA insert was isolated and purified by agarose gel electrophoresis. This fragment contains the entire open reading-frame of the PDE. The fragment was labeled with radioactive nucleotides by random priming.

The cDNA libraries were plated on a 150 mm petri dishes at a density of approximately 50,000 plaques per plate. Duplicate nitrocellulose filter replicas were prepared. The radioactive nucleic acid probe was used for hybridization to the filters overnight at 42° C. in 50% formamide, 5x SSPE (0.9M NaCl, 0.05M NaH$_2$PO$_4$.H$_2$O, 0.04M NaOH, and 0.005M Na$_2$EDTA.2H$_2$O), 0.5% SDS, 100 µg/ml salmon testes DNA, and 5x Denhardt's solution. The filters were washed initially at room temperature and subsequently at 65° C. in 2x SSC containing 0.1% SDS. Positive plaques were purified and their inserts were subcloned into an appropriate sequencing vector for DNA sequence analysis by standard techniques.

First, a λgt10 cDNA library prepared from human hippocampus mRNA (clontech, random and dT primed) was screened. Of the approximately 500,000 plaques examined, 33 hybridized to the probe. One of these phages was digested with EcoRI to remove the cDNA insert. This insert-containing EcoRI fragment was cloned into Bluescript KS that had been digested with EcoRI and then treated with calf intestine alkaline phosphatase. One product of this reaction was the plasmid pGSPDE9.2, which showed two major differences when compared to the bovine cGS-PDE cDNA. The 5'0.4 kb of the pGSPDE9.2 insert diverged from the bovine cDNA. Approximately 0.7 kb from the 5' end of the human cDNA there is a 0.7 kb region that diverges from the bovine cDNA. This region may be an intron. Twenty-five of the remaining hippocampus plaques that had hybridized to the bovine probe were examined by PCR, hybridization and/or sequencing. None were found to extend through the regions that differed between the bovine and human cDNAs.

Phages λ GSPDE7.1 and λ GSPDE7.4, two other phages from the hippocampus library, were digested with EcoRI and HindIII. Each yielded a 1.8-kb fragment that contains most of the cDNA insert and approximately 0.2-kb of phage lambda DNA. The λ DNA is present in the fragment because in each case one of the EcoRI sites that typically bracket a cDNA insert had been destroyed, possibly when the library was constructed. The EcoRI/HindIII fragments were cloned into Bluescript KS digested with EcoRI and HindIII. This procedure gave rise to the plasmids pGSPDE7.1 and pGSPDE7.4. The cDNA inserts encode DNA homologous to the 3' portion of the bovine phosphodiesterase cDNA. Both of the cDNA inserts in these clones begin at an EcoRI site and the sequences are homologous adjacent this site.

Portions of pGSPDE7.1 and pGSPDE7.4 cDNA inserts were sequenced and are identical except for a short region of their 3' ends. The cDNA insert in pGSPDE7.1 ends with a sequence of approximately 70 adenine bases, while the cDNA insert in pGSPDE7.4 ends with three additional nucleotides not present in pGSPDE7.1 followed by a sequence of approximately 20 adenine bases.

Next, a cDNA library prepared in λ ZapII (Stratagene) from human heart mRNA yielded one hybridizing plaque from the approximately 500,000 screened. The Bluescript; SK(−) plasmid pGSPDE6.1 containing the hybridizing insert was excised in vivo from the λ ZapII clone. Sequence analysis showed that the insert is homologous to the bovine phosphodiesterase cDNA. The homologous reunion spans the position of the EcoRI found in the sequence formed by joining the sequence of the insert from pGSPDE9.2 to the sequence of the insert in pGSPDE7.1 or PGSPDE7.4. Thus, it is thought that the two clones from the hippocampus form a complete open reading frame.

A third λ gt10library derived from human placenta mRNA yielded five hybridizing plaques from approximately 800,000 screened. These placental cDNA clones were short and their sequences were identical to portions of the hippocampus cDNA pGSPDE9.2. Screening 5×10$^5$ plaques from U118 glioblastoma cDNA library, 5×10$^5$ from a spleen cDNA library and 5×10$^5$ from an adrenal library (Cushings Disease) gave no hybridization plaques.

Given the homology between the bulk of human and bovine cGS-PDE sequence, it was decided to obtain multiple independent cDNA clones containing the 5' end of the human cGS-PDE to determine if the 0.4 kb 5' sequence was an artifact. An approximately 0.95 kb EcoRI-HindII fragment from the 5' end of the bovine cGS cDNA plasmid p3cgs5 was random primed and used as a probe to screen a number of human cDNA libraries. Hippocampus library screening was carried out under the same screening conditions as described above. All remaining screenings were carried out as described with respect to human heart cDNA library screenings in Example VII, infra. No positives were obtained screening 5×10$^5$ plaques from a human T cell library (Hut78, dT-primed), 10$^6$ plaques from the hippocampus cDNA library (random and dT-primed), 5×10$^5$ plaques from a human liver cDNA library (dT-primed, 5' stretch, Clontech), 5×10$^5$ plaques from a human SW1088 glioblastoma cDNA library (dT-primed), 5×10$^5$ plaques from the same heart cDNA library (random and dT-primed), and 1.5×10$^6$ plaques from a human lung cDNA library (random primed). Two positives were obtained from screening 5×10$^5$ plaques from a human fetal brain cDNA library (random and dT-primed, Stratagene). These were designated as HFB9.1 and HFB9.2.

Bluescript SK(−) plasmids pHFB9.2 and pHFB9.1 were excised in vivo from the λZapII clones. DNA sequence analysis revealed that HFB9.1 starts about 80 nucleotides further 3' than does HFB9.2 and reads into an intron approximately 1.9 kb of the way into HFB9.2. HFB9.2 covers the entire open reading frame of the cGS-PDE, but reads into what may be an intron 59 nucleotides after the stop codon. Both of them lack the 5'0.4 kb and the presumed intron found in pGSPDE9.2. The entire open reading frame of HFB9.2 was isolated and assembled into yeast expression vector pBNY6N. The resulting plasmid, designated pHcgs6n, includes the coding region of the cDNA as an EcoRI/XhoI insert. DNA and deduced amino acid sequences for the insert are provided in SEQ.ID No: 44 and 45, respectively.

EXAMPLE VII
Use of CaM-PDE 61 kDa Bovine Brain cDNA to Obtain Human CaM-PDE 61 kDa cDNA Human cDNA clones, λ CaM H6a and λ CaM H3a, which are homologous to the cDNA encoding the bovine 61 kDa CaM-PDE, were obtained by hybridization using a nucleic acid probe derived from the cDNA encoding the bovine species enzyme. A combination of sequence analysis and hybridization studies indicate that λ Cam H6a contains most of an open reading frame encoding a human CaM-PDE.

The hybridization probe used to isolate the human DNA was derived from first strand cDNA of bovine lung tissue by PCR treatment. More specifically the 23-mer oligonucleotide designated PCR-2S in Example I (see, SEQ ID NO: 1) was combined in a PCR reaction with bovine lung cDNA and a redundant antisense 23-mer oligonucleotide (PCR-5AS) based on the pCAM insert sequence with

SEQ ID NO: 46
5'TCRTTNGTNGTNCCYTTCATRTT-3' representing the amino acid sequence

SEQ ID NO: 47
NMKGTTND, according to the general procedures of Examples I and III, to generate a 1098 bp cDNA fragment representing a large portion of the coding region of the pCAM-40 insert. The PCR products were purified on a 1% agarose gel using 0.4M Tris-acetate/0.001M EDTA buffer containing 0.5 µg/ml ethidium bromide. The DNA products were visualized with UV light, cleanly excised from the gel with a razor blade, purified using Geneclean II reagent kit and ligated into EcoRV-cut pBluescript vector DNA.

To determine if the PCR amplification products were CAM-PDE cDNAS, the subcloned PCR DNA products were sequenced from the ends using T3 and T7 promoter primers and either Sequenase or Taq Polymerase sequencing kits. Approximately 250 bases from each end of this DNA were then compared to the amino acid sequence of bovine CAM-PDE, confirming that the PCR DNA product was a partial CAM PDE cDNA. This clone was designated pCAM-1000 and contained a 1.1 -kb insert of nucleic acid that corresponds to nucleotides 409 to 1505 of the insert of pCAM-40. pCaM1000 was digested with the restriction enzymes HindIII and BamHI. The 1.1 -kb fragment was purified by agarose gel electrophoresis and then digested with the restriction enzyme AccI. The two fragments were separated and purified by agarose gel electrophoresis. These separated fragments were labeled with radioactive nucleotides by random priming.

Human cDNA libraries were plated on 150 mm petri dishes at a density of approximately 50,000 plaques per dish and duplicate nitrocellulose filter replicas were prepared. Each probe was hybridized to a separate set of the duplicate filters. The filters were hybridized overnight at 65° C. in 3x SSC, 0.1% sarkosyl, 50 µg/ml salmon testes DNA, 10x Denhardt's solution, 20 mM sodium phosphate (pH 6.8). They were washed at 65° C. in 2x SSC containing 0.1% SDS.

A λ gt10 library prepared from human hippocampus mRNA yielded three hybridizing plaques of the approximately 500,000 screened. Of these three hybridizing plaques, two hybridized to both probes and the third hybridized to the longer of the two probes. The λ Cam H6a clone contains an approximately 2 kb insert that is homologous to the cDNA encoding the bovine clone of pCAM-40.

The λ cam H6a cDNA was subcloned into the plasmid Bluescript KS for sequence analysis. Although the cDNA library had been constructed with EcoRI linkers, one of the EcoRI sites that should have flanked the cDNA insert did not cut with EcoRI. Thus, the cDNA was subcloned as two fragments: an approximately 0.7 kb EcoRI/HindIII fragment (pcamH6C) and an approximately 1.6 kb HindIII fragment that contained approximately 1.3 kb of cDNA and 0.25 kb of flanking λgt10 vector DNA (pcamH6B). DNA sequence analysis revealed that it encoded most of a human CaM-PDE homologous to the bovine 61k CaM-PDE, except that the human cDNA appeared to be missing two base pairs in the middle of the coding region. These missing nucleotides correspond to positions 626 and 627 of the human cDNA sequence if it is aligned with the pCAM-40 bovine 61 kDa CaM-PDE (SEQ. ID NO: 5 for maximum homology.

Another of the cDNA clones from the hippocampus cDNA library that had been screened with the bovine 61 kDa CaM-PDE probes was λCamH2a. It contained an approximately 1.0 kb insert. As was the case for λCamH6a cDNA, only one of the two EcoRI sites that should be present-at the ends of the insert would cut. The original subcloning and DNA sequence analysis for this cDNA utilized PCR fragments generated with oligos in the flanking λgt10 vector arms. This cDNA overlaps much of the 5' end of the insert in λCamH6a and contained the additional two nucleotides predicted by the bovine sequence and required to maintain the PDE open reading frame. The λCamH2a insert also appeared to contain two introns; one 5' of the initiator methionine and one downstream of the HindIII site. The EcoRI/HindIII fragment from λCamH2a (corresponding to the region covered by pcamH6C) was subcloned into the plasmid Bluescript SK⁻ and designated pcamH2A-16. This was then used as the source of the two additional bp in the construction of yeast expression plasmids described below.

Two different plasmids were constructed for human CaM-PDE expression in yeast. One plasmid, pHcam61-6N-7, contains the entire open reading frame. The second plasmid, pHcam61met140, starts at an internal methionine (beginning at nucleotide position 505) and extends to the end of the open reading frame. These expression plasmids were constructed by modifying the 3' portion of the open reading frame and then adding the two differently modified 5' ends to the 3' end. The sequence of the cDNA insert of pHcam61-6N-7 is set out in SEQ. ID NO: 48 and the deduced amino acid sequence of the CaM-PDE encoded thereby is set out in SEQ. ID NO: 49. During construction of the cDNA insert, the nucleotide at position 826 was altered from T to C, but the encoded amino acid was conserved. Plasmid pHcam61met140, as noted above, has a cDNA insert lacking the first 140 codons of the coding region of the pHcam61-6N-7 but is otherwise identical thereto.

A third cDNA, λcamH3a, contained an approximately 2.7 kb insert. This cDNA insert was subcloned for sequence analysis. Although the cDNA library had been constructed with EcoRI, the inserted cDNA in λCamH3a could not be excised with EcoRI.

Presumably one of the EcoRI sites was destroyed during the construction of the library. The cDNA insert was excised from the λ clone by digestion with HindIII and EcoRI. This digestion yields two relevant fragments, a 0.6 kb HindIII fragment which contains a portion of DNA from the left arm of λgt10 attached to the cDNA insert and an approximately 2.4 kb HindIII/EcoRI fragment containing the remainder of the cDNA insert. These two fragments were assembled in the plasmid Bluescript KS to yield an approximately 3 kb fragment. The orientation of the small HindIII fragment was the same as the original λ clone. This subclone is known as pcamH3EF. Although this cDNA hybridizes to the bovine probe from the bovine CaM-PDE 61 kDa cDNA, sequence analysis revealed that it appeared to be the product of a different CaM-PDE gene. Plasmid pcamH3EF contains what may be the entire open reading frame and would encode a protein approximately 75% homologous to the protein encoded by the insert of pHcam61-6N-7 over much of its lengths. DNA and deduced amino acid sequences are set out in SEQ. ID NOS: 50 and 51, respectively. The DNA sequence of the region between nucleotide 80 and 100 of pcamH3EF is uncertain. This area is 5' to the initiator methionine codon and thus does not effect the open reading frame.

An approximately 2.4 kb fragment of pcamH3EF was gel purified following digestion with the restriction enzymes HindIII and EcoRI. This fragment was used to screen additional human cDNA libraries in a similar manner to the screen described above. Screening approximately 5×10⁵ plaques from a human heart cDNA library (Stratagene) yielded two plaques that hybridized to the pcamH3EF probe. The Bluescript SK[31] plasmid pcamHella was excised in vivo from one of these positive λZapII clones. DNA and deduced amino acid sequences for the cDNA insert are set out in SEQ. ID NO: 52 and 53, respectively. Sequence analysis of pcamHella showed that the insert began at nucleotide position 610 of pcamH3EF and was nearly identical through nucleotide position 2066, at which point the DNA sequence diverged from that of pcamH3EF. The cDNA insert of pcamHella continued for approximately 0.6 kb. The consequence of this divergence is to alter the carboxy terminus of the protein that would be encoded by the open reading frame within the cDNA. The pcamH3EF cDNA could encode a protein of 634 amino acids (MW72,207). Assuming the 5' end of the pcamHella cDNA is the same as that of the 5' end of pcamH3EF (5' to nucleotide position 610), pcamHella could encode a 709 amino acid protein (MW80,759). These divergent 3' ends may be the consequence of alternative splicing, lack of splicing, or unrelated DNA sequences being juxtaposed during the cloning process.

EXAMPLE VIII

Expression of Bovine and Human PDE cDNAs for Complementation of Yeast Phenotypic Defects The present example relates to the expression of bovine and PDE clones in yeast demonstrating the capacity of functional PDE expression products to suppress the heat shock phenotype associated with mutation of yeast phosphodiesterase genes and also relates to the biochemical assay of expression products. The host cells used in these procedures were S. cerevisiae yeast strains 10DAB (ATCC accession No. 74049) and YKS45, both of which were pde[1−] pde[2−] resulting in a phenotype characterized by heat shock sensitivity, i.e., the inability of cells to survive exposure to elevated temperatures on the order of 55°–56° C. In these complementation procedures, the inserted gene product was noted to conspicuously modify the heat shock phenotype.

This capacity, in turn, demonstrates the feasibility of systems designed to assay chemical compounds for their ability to modify (and especially the ability to inhibit) the in vivo enzymatic activity of mammalian $Ca^{2+}$/calmodulin stimulated and cGMP stimulated cyclic nucleotide phosphodiesterase.

A. Yeast Phenotype Complementation by Expression of a cDNA Encoding CaM-PDE

A 2.2 kb cDNA fragment, adapted for insertion into yeast expression plasmids pADNS (ATCC accession No. 68588) and pADANS (ATCC accession No. 68587) was derived from plasmid pCAM-40 (Example I) by polymerase chain reaction. Briefly, the following PCR amplification was employed to alter the pCAM-40 DNA insert to align it appropriately with the ADH1 promoter in the vectors.

One oligonucleotide primer (Oligo A) used in the PCR reaction

SEQ ID NO: 54
5'-TACGAAGCTTTGATGGGGTCTACTGCTAC-3' anneals to the pCaM-40 cDNA clone at base pair positions 100–116 and includes a HindIII site before the initial methionine codon. A second oligonucleotide primer (Oligo B)

SEQ ID NO: 55
5'-TACGAAGCTTTGATGGTTGGCTTGGCATATC-3' was designed to anneal at positions 520–538 and also includes a HindIII site two bases before a methionine codon. The third oligonucleotide

SEQ ID NO: 56
5'-ATTACCCCTCATAAAG-3' annealed to a position in the plasmid that was 3' of the insert. For one reaction, Oligo A and oligo C were used as primers with pCAM-40 as the template. The nucleic acid product of this reaction included the entire open reading frame. A second reaction used Oligo B and Oligo C as primers on the template pCAM-40 and yielded a nucleic acid product that lacked the portion of the cDNA sequence encoding the calmodulin binding domain. These amplified products were digested with HindIII and NotI and ligated to HindIII/NotI-digested yeast expression vectors pADNS and pADANS. Plasmid clones containing inserts were selected and transformed into S. cerevisiae strain 10DAB by lithium acetate transformation.

Transformed yeast were streaked in patches on agar plates containing synthetic medium lacking the amino acid leucine (SC-leucine agar) and grown for 3 days at 30° C. Replicas of this agar plate were made with three types of agar plates: one replica on SC-leucine agar, one replica on room temperature YPD agar, and three replicas on YPD agar plates that had been warmed to 56° C. The three warmed plates were maintained at 56° C. for 10, 20, or 30 minutes. These replicas were than allowed to cool to room temperature and then all of the plates were placed at 30° C. Yeast transformed with plasmids constructed to express the CaM-PDE were resistant to the thermal pulse. More specifically, both the construct designed to express the complete open reading frame and that designed to express the truncated protein (including the catalytic region but not the calmodulin binding domain), in either pADNS or pADANS, complemented the heat shock sensitivity phenotype of the 10DAB host cells, i.e., rendered them resistant to the 56° C. temperature pulse.

In a like manner, plasmids pHcam61-6N-7 and pHcam61met140(Example VII) were transformed into yeast host 10DAB. Heat shock phenotypes were suppressed in both transformants.

B. Biochemical Assay of Expression Products

The bovine CaM-PDE expression product was also evaluated by preparing cell-free extracts from the 10DAB yeast cells and measuring the extracts' biochemical phosphodiesterase activity. For this purpose, 200 ml cultures of transformed yeast were grown in liquid SC-leucine to a density of about 6 million cells per ml. The cells were collected by centrifugation and the cell pellets were frozen. Extracts were prepared by thawing the frozen cells on ice, mixing the cells with 1 ml of PBS and an equal volume of glass beads, vortexing them to disrupt the yeast cells, and centrifuging the disrupted cells at approximately 12,000×g for 5 min to remove insoluble debris. The supernatant was assayed for phosphodiesterase activity.

Extracts of yeast cells, up to 50 µl, were assayed for phosphodiesterase activity in 50 mM Tris (pH 8.0), 1.0 mM EGTA, 0.01 mg/mL BSA (bovine serum albumin), [$^3$H]-cyclic nucleotide (4–10,000 cpm/pmol), and 5 mM $MgCl_2$ in a final volume of 250 al at 30° C. in 10×75 mm glass test tubes. The incubations were terminated by adding 250 µl of 0.5M sodium carbonate pH 9.3, 1M NaCl, and 0.1% SDS.

The products of the phosphodiesterase reaction were separated from the cyclic nucleotide by chromatography on 8×33 mm columns of BioRad Affi-Gel 601 boronic acid gel. The columns were equilibrated with 0.25M sodium bicarbonate (pH 9.3) and 0.5M NaCl. The reactions were applied to the columns. The assay tubes were rinsed with 0.25M sodium bicarbonate (pH 9.3) and 0.5M NaCl and this rinse was applied to the columns.

The boronate columns were washed twice with 3.75 ml of 0.25M sodium bicarbonate (pH 9.3) and 0.5M NaCl followed by 0.5 ml of 50 mM sodium acetate (pH 4.5). The product was eluted with 2.5 ml of 50 mM sodium acetate (pH 4.5) containing 0.1M sorbitol and collected in scintillation vials. The eluate was mixed with 4.5 ml Ecolite Scintillation Cocktail and the radioactivity measured by liquid scintillation spectrometry.

Both the construct designed to express the complete bovine open reading frame and that designed to express a truncated protein, in either pADNS or pADANS, expressed active protein as determined by biochemical phosphodiesterase assay of cell extracts. Extracts of 10DAB harboring pcam61met140 yielded measurable phorphodiesterase activity (see, infra, second method of part D) while the extract of 10DAB cells harboring pcamH61-6N-7 lacked detectable activity.

C. Yeast Phenotype Complementation by Expression of a cDNA Encoding a cGS-PDE

The plasmid p3CGS-S, which contains a 4.2-kb DNA fragment encoding the bovine cGS-PDE, was adapted for cloning into pADNS and pADANS by replacing the first 147 bases of the cDNA with a restriction site suitable for use in insertion into plasmids. The oligonucleotide BS1, having the sequence

SEQ ID NO: 57
5'TACGAAGCTTTGATGCGCCGACAGCCTGC, encodes a HindIII site and anneals to positions 148–165 of the cDNA insert. An oligonucleotide designated BS3

SEQ ID NO: 58
GGTCTCCTGTTGCAGATATTG, anneals to positions 835–855 just 3' of a unique NsiI site. The resulting PCR-generated fragment following digestion with HindIII and NsiI was then ligated to HindIII- and NsiI-digested p3CGS-5 thereby replacing the original 5' end of the bovine cDNA. A plasmid derived from this ligation was digested with HindIII and NotI to release the modified cDNA insert. The insert was cloned into pADNS and pADANS at their HindIII and NotI sites. These plasmids were then transformed into the yeast strain 10DAB by the lithium acetate method and the transformed cells were grown and subjected to elevated temperatures as in Section A, above. Yeast transformed with plasmids constructed to express the bovine cGS-PDE were resistant to the thermal pulse.

In a like manner, plasmid pHcgs6n (Example VI) was transformed into yeast: host strain YKS45 by lithium acetate transformation. Heat shock analysis was performed as above except that the plates were initially grown two days at 30° C. and the warmed plates were maintained at 56° C. for 10, 20, 30 and 45 minutes. Yeast transformed with the plasmid designed to express the full length human cGS-PDE was resistant to thermal pulse.

D. Biochemical Assay of Expression Product

The expression of the bovine cGS-PDE was also evaluated by preparing cell-free extracts from the yeast and measuring the extracts' biochemical phosphodiesterase activity. For this purpose, 50 ml cultures of transformed 10DAB yeast cells were grown in liquid SC-leucine to a density of about 10 million cells per ml. Sherman et al., *Methods in Yeast Genetics*, Cold Spring Harbor Laboratory, Cold Spring Harbor, N.Y. (1986). The cells were collected by centrifugation, the cell pellets were washed once with water, and the final cell pellets were frozen. To prepare an extract, the frozen cells were thawed on ice, mixed with 1 ml of PBS and an equal volume of glass beads, vortexed to disrupt the yeast cells, and centrifuged to remove debris. The supernatant was then assayed for phosphodiesterase activity as in Section B, above. Constructs in either pADNS or pADANS expressed active protein as determined by biochemical phosphodiesterase assay of cell extracts.

YKS45 transformed with plasmid pHcgs6n were grown in SC-leu medium to $1-2\times10^7$ cells/ml. The cells were harvested by centrifugation and the cell pellets were frozen. A frozen cell pellet, typically containing $10^{10}$ cells, was mixed with lysis buffer (25 mM Tris HCl pH 8, 5 mM EDTA, 5 mM EGTA, 1 mM o-phenathroline, 0.5 mM AEBSF, 0.01 mg/mL pepstatin, 0.01 mg/mL leupeptin, 0.01 mg/mL aprotinin, 0.1% 2-mercaptoethanol) to bring the total volume to 2.5 ml. The mixture was thawed on ice and then added to an equal volume of glass beads. The cells were disrupted by cycles of vortexing and chilling on ice, then additional lysis buffer was mixed with the disrupted cells to bring the total lysis buffer added to 5 ml. The suspension was centrifuged for 5 min. at 12,000×g. The supernatant was removed and either assayed immediately or frozen rapidly in a dry ice ethanol bath and stored at −70° C.

Phosphodiesterase activity was assayed by mixing an aliquot of cell extract in (40 mM Tris-Cl pH 8.0, 1. mM EGTA, 0.1 mg/mL BSA) containing 5 mM $MgCl_2$ and radioactive substrate, incubating at 30° C. for up to 30 min. and terminating the reaction with stop buffer (0.1M ethanolamine pH 9.0, 0.5M ammonium sulfate, 10 mM EDTA, 0.05% SDS final concentration). The product was separated from the cyclic nucleotide substrate by chromatography on BioRad Affi-Gel 601. The sample was applied to a column containing approximately 0.25 ml of Affi-Gel 601 equilibrated in column buffer (0.1M ethanolamine pH 9.0 containing 0.5M ammonium sulfate). The column was washed five times with 0.5 ml of column buffer. The product was eluted with four 0.5 ml aliquots of 0.25M acetic acid and mixed with 5 ml Ecolume (ICN Biochemicals). The radioactive product was measured by scintillation counting. Extracts from yeast expressing the human cGS-PDE hydrolyzed both cyclic AMP and cyclic GMP, as expected for this isozyme.

EXAMPLE IX

Tissue Expression Studies Involving CaM-PDE and CGS-PDE Polynucleotides

A. Northern Blot Analysis

DNAs isolated in Examples I, III, and IV above were employed to develop probes for screening total or poly A-selected RNAs isolated from a variety of tissues and the results are summarized below.

1. Northern analysis was performed on mRNA prepared from a variety of bovine adrenal cortex, adrenal medulla, heart, aorta, cerebral cortex, basal ganglia, hippocampus, cerebellum, medulla/spinal cord, liver, kidney cortex, kidney medulla, kidney papillae, trachea, lung, spleen and T-lymphocyte tissues using an approximately 3 kb radiolabeled cDNA fragment isolated from plasmid p3CGS-5 upon digestion with EcoRI and SmaI. A single 4.5 kb mRNA species-was detected in most tissues. The size of the CGS- PDE E WA appeared to be slightly larger (approximately 4.6 kb) in RNA isolated from cerebral cortex, basal ganglia and hippocampus. The cGS PDE mRNA was most abundant in adrenal cortex. It was also abundant in adrenal medulla and heart. It appeared to be differentially expressed in anatomically distinct regions of the brain and kidney. Among RNAs isolated from five different brain regions, cGS PDE mRNA was most abundant in hippocampus, cerebral cortex, and basal ganglia. Very little cGS PDE transcript was detected in cerebellum or medulla and spinal cord RNAs. Although the cGS PDE mRNA was detected in all regions of the kidney, it appeared to be most abundant in the outer red medulla and papillae. The cGS PDE mRNA was also detected in liver, trachea, lung, spleen, and T-lymphocyte RNA. Very little cGS PDE mRNA was detected in RNA isolated from aorta.

2. Radiolabeled DNA probes were prepared from random hexamer primed fragments extended on heat denatured 1.6 kb EcoRI restriction endonuclease fragments of the cDNA insert of plasmid pCAM-40. In Northern analysis, the DNA probes hybridized with 3.8 and 4.4 kb mRNAs in brain and most of the other tissues analyzed including cerebral cortex, basal ganglia, hippocampus, cerebellum, medulla and spinal cord, heart, aorta, kidney medulla, kidney papillae, and lung. Hybridization of probe with the 3.8 kb mRNA from liver, kidney cortex and trachea was only detected after longer autoradiographic exposure.

3. Northern blot analysis of mRNA from several tissues of the central nervous system was carried out using a subcloned, labeled p12.3a DNA fragment (containing most of the conserved PDE catalytic domain) as a probe. The most intense hybridization signal was seen in mRNA from the basal ganglia and strong signals were also seen in mRNA from other tissues including kidney papilla and adrenal medulla.

B. RNAse Protection

1. Three antisense riboprobes were constructed. Probe III corresponds to the catalytic domain-encoding region of p3cGS-5 (273 bp corresponding to bases 2393 through 2666 of SEQ. ID NO: 38); probe II to the cGMP-binding domain encoding (468 bp corresponding to bases 959 through 1426; and probe I to the 5' end and portions of amino terminal-encoding region (457 bases corresponding to bases 1 through 457).

Total RNAs extracted from all of the examined tissues completely protected probes II and III. Nearly complete protection (457 bases) of riboprobe I with RNAs isolated from adrenal cortex, adrenal medulla, and liver was also observed. However, RNA isolated from cerebral cortex, basal ganglia, and hippocampus only protected an approximately 268-base fragment of riboprobe I. A relatively small amount of partially protected probe I identical in size with the major fragments observed in the brain RNA samples was also detected in RNAs isolated from all of the examined tissues except liver. Interestingly, heart RNA yielded both completely protected (457 base) riboprobe and, like brain RNA, a 268-base fragment. Unlike the protection pattern observed using RNAs isolated from any of the other tissues, however, the partially protected riboprobe I fragment appeared to be more abundant. The results suggest that two different cGS-PDE RNA species are expressed.

2. Radiolabeled antisense riboprobes corresponding to a portion of either the CaM-binding domain on the catalytic domain of CaM-PDE were constructed from restriction endonuclease cleavage fragments (AccI/SstI and Tth111I/HincII) of pCAM-40cDNA. Total RNAs isolated from five different brain regions (cerebral cortex, basal ganglia, hippocampus, cerebellum, and medulla/spinal cord) completely protected the antisense riboprobes encoding both the CaM-binding and catalytic domains. Total RNAs from heart, aorta, lung, trachea and kidney completely protected the riboprobe corresponding to the catalytic domain but only protected about 150 bases of the CaM-binding domain riboprobe, suggesting that an isoform structurally related to the 61kD CaM-PDE is expressed in these tissues.

3. Antisense riboprobes were generated based on plasmid p12.3a and corresponding to bases −1 through 363 and 883–1278 of SEQ. ID NO: 26. The former probe included 113 bases of the 5' noncoding sequence as well as the start methionine cordon through the putative CaM-binding domain, while the latter encoded the catalytic domain. Among all tissues assayed, RNA from basal ganglia most strongly protected each probe. Strong signals of a size corresponding to the probe representing the amino terminus were observed in protection by cerebral cortex, cerebellum, basal ganglia, hippocampus and adrenal medulla RNA. No protection was afforded to this probe by kidney papilla or testis RNA even though the tissue showed signals on the Northern analysis and RNAse protection of the conserved domain probe, suggesting that a structurally related isozyme is expressed in this tissue.

While the present invention has been described in terms of specific methods and compositions, it is understood that variations; and modifications will occur to those skilled in the art upon consideration of the invention. Consequently only such limitations as appear in the appended claims should be placed thereon. Accordingly, it is intended in the appended claims to cover all such equivalent variations which come within the scope of the invention as claimed.

---

What is claimed is:

1. An assay method for identifying, a chemical agent which modifies the enzymatic activity of a mammalian $Ca^{2+}$/calmodulin sensitive cyclic nucleotide phosphodiesterase said method comprising:

(a) stably transforming, with a polynucleotide sequence encoding a mammalian $Ca^{2+}$/calmodulin stimulated phosphodiesterase selected from the group consisting of a polypeptide as set forth in SEQ ID NOs: 6, 17, 27, 49, 51, and 53, a eucaryotic host cell having a heat-shock sensitivity phenotypic character susceptible to alteration, such that upon expression of said polynucleotide sequence said cell exhibits an altered heat-shock phenotype;

(b) growing the transformed host cell formed in step (a) in a nutrient medium under conditions allowing expression of said polynucleotide sequence in said transformed host cell accompanied by the corresponding alteration in the transformed host cell phenotype;

(c) contacting the transformed host cells grown according to step (b) with a chemical agent to be assayed; and (d) determining if the chemical agent of step (c) modifies the enzymatic activity of the enzyme of step (a) by determining if the altered heat-shock phenotype of the cells of step (c) has been modified.

2. An assay method according to claim 1 wherein said host cell is a yeast host cell.

3. An assay method for identifying a chemical agent which modifies the enzymatic activity of a mammalian $Ca^{2+}$/calmodulin sensitive cyclic nucleotide phosphodiesterase, said method comprising:

(a) stably transforming, with a polynucleotide sequence encoding a mammalian $Ca^{2+}$/calmodulin sensitive cyclic nucleotide phosphodiesterase selected from the group consisting of a polypeptide as set forth in SEQ ID NOs: 6, 17, 27, 49, 51, and 53, a eucaryotic host cell having a heat-shock phenotypic character susceptible to alteration, such that upon expression of said polynucleotide sequence said cell exhibits an altered heat-shock phenotype;

(b) growing the transformed host cell formed in step (a) in a nutrient medium under conditions allowing expression of said polynucleotide sequence in said transformed host cell accompanied by the corresponding alteration in the host cell phenotype;

(c) identifying said transformed host cells having an altered heat-shock phenotype;

(d) disrupting said transformed host cells;

(e) isolating cytosol from said disrupted transformed host cells;

(f) contacting said cytosol with said chemical agent; and (g) determining whether said enzymatic activity has been altered.

4. An assay method according to claim 3 wherein said host cell is a yeast host cell.

* * * * *

UNITED STATES PATENT AND TRADEMARK OFFICE
CERTIFICATE OF CORRECTION

PATENT NO.    : 5,800,987
DATED         : September 1, 1998
INVENTOR(S)   : Joseph A. Beavo et al.

It is certified that error appears in the above-identified patent and that said Letters Patent is hereby corrected as shown below:

Title page,
Under References Cited, Kincaid et al., replace "Dependint" with -- Dependent --, and Seed, replace "Proein" with -- Protein --.

Column 2,
Line 37, replace "hinds" with -- binds --.
Line 62, replace "proteins; have" with -- proteins have --.

Column 3,
Line 37, replace "mean" with -- means --.
Line 59, replace "be, greatly" with -- be greatly --.

Column 7,
Line 64, replace "oliqonucleotides" with -- oligonucleotides --.

Column 11,
Line 1, replace "CAMP" with -- cAMP --.
Line 41, replace "bard" with -- band --.

Column 12,
Line 49, replace "$\cong 59$" with -- $\approx 59$ --.
Line 63, replace "p59KCAMPDE-2/CDM[8was" with -- p59KCAMPDE-2/CDM8, was --.

Column 18,
Line 39, replace "colamns" with -- columns --.

Column 19,
Line 4, replace "where" with -- were --.

Column 21,
Line 50, replace "an, EcoRI" with -- an EcoRI --.

Column 23,
Line 19, replace "cDNAS" with -- cDNAs --.

UNITED STATES PATENT AND TRADEMARK OFFICE
CERTIFICATE OF CORRECTION

PATENT NO. : 5,800,987
DATED : September 1, 1998
INVENTOR(S) : Joseph A. Beavo et al.

It is certified that error appears in the above-identified patent and that said Letters Patent is hereby corrected as shown below:

Column 24,
Line 3, replace "present-at" with -- present at --.
Line 61, replace "effect" with -- affect --.

Column 26,
Line 32, replace "than" with -- then --.

Column 27,
Line 21, replace "phorphodiesterase" with -- phosphodiesterase --.

Column 28,
Line 67, replace "species-was" with -- species was --.

Column 29,
Line 1, replace "PDE E WA" with -- PDE mRNA --.

Column 30,
Line 44, replace "variations;" with -- variations --.

Column 127,
Line 8, replace "identifying, a" with -- identifying a --.

Signed and Sealed this

Twenty-first Day of May, 2002

*Attest:*

JAMES E. ROGAN
*Attesting Officer*     *Director of the United States Patent and Trademark Office*

SEQUENCE LISTING ( 1 ) GENERAL INFORMATION:

( i i i ) NUMBER OF SEQUENCES: 58

( 2 ) INFORMATION FOR SEQ ID NO:1:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:1:

AARATGGGNA TGAARAARAA                        20

( 2 ) INFORMATION FOR SEQ ID NO:2:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:2:

Lys Met Gly Met Met Lys Lys Lys
1               5

( 2 ) INFORMATION FOR SEQ ID NO:3:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:3:

ACRTTCATYT CYTCYTCYTG CAT                    23

( 2 ) INFORMATION FOR SEQ ID NO:4:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:4:

Met Gln Glu Glu Glu Met Asn Val
1               5

( 2 ) INFORMATION FOR SEQ ID NO:5:

( i ) SEQUENCE CHARACTERISTICS:
        ( A ) LENGTH: 2291 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 100..1689

( x i ) SEQUENCE DESCRIPTION: SEQ ID NO:5:

GGCTCAGAAA CTGTAGGAAT TCTGATGTGC TTCGGTGCAT GGAACAGTAA CAGATGAGCT        60

GCTTTGGGGA GAGCTGGAAC GCTCAGTCGG AGTATCATC ATG GGG TCT ACT GCT         114
                                             Met Gly Ser Thr Ala
                                               1               5

ACA GAA ACT GAA GAA CTG GAA AAC ACT ACT TTT AAG TAT CTC ATT GGA        162
Thr Glu Thr Glu Glu Leu Glu Asn Thr Thr Phe Lys Tyr Leu Ile Gly
            10                  15                  20

GAA CAG ACT GAA AAA ATG TGG CAA CGC CTG AAA GGA ATA CTA AGA TGC        210
Glu Gln Thr Glu Lys Met Trp Gln Arg Leu Lys Gly Ile Leu Arg Cys
        25                  30                  35

| | | | | | | | | | | | | | | | | |
|---|---|---|---|---|---|---|---|---|---|---|---|---|---|---|---|---|
| TTA | GTG | AAG | CAG | CTG | GAA | AAA | GGT | GAT | GTT | AAC | GTC | ATC | GAC | TTA | AAG | 258 |
| Leu | Val | Lys | Gln | Leu | Glu | Lys | Gly | Asp | Val | Asn | Val | Ile | Asp | Leu | Lys | |
| | | 40 | | | | 45 | | | | | 50 | | | | | |
| AAG | AAT | ATT | GAA | TAT | GCA | GCA | TCT | GTG | TTG | GAA | GCA | GTT | TAT | ATT | GAT | 306 |
| Lys | Asn | Ile | Glu | Tyr | Ala | Ala | Ser | Val | Leu | Glu | Ala | Val | Tyr | Ile | Asp | |
| | 55 | | | | 60 | | | | | 65 | | | | | | |
| GAA | ACA | AGG | AGA | CTG | CTG | GAC | ACC | GAT | GAT | GAG | CTC | AGT | GAC | ATT | CAG | 354 |
| Glu | Thr | Arg | Arg | Leu | Leu | Asp | Thr | Asp | Asp | Glu | Leu | Ser | Asp | Ile | Gln | |
| 70 | | | | | 75 | | | | 80 | | | | | | 85 | |
| TCG | GAT | TCC | GTC | CCA | TCA | GAA | GTC | CGG | GAC | TGG | TTG | GCT | TCT | ACC | TTT | 402 |
| Ser | Asp | Ser | Val | Pro | Ser | Glu | Val | Arg | Asp | Trp | Leu | Ala | Ser | Thr | Phe | |
| | | | | 90 | | | | | 95 | | | | | 100 | | |
| ACA | CGG | AAA | ATG | GGG | ATG | ATG | AAA | AAG | AAA | TCT | GAG | GAA | AAA | CCA | AGA | 450 |
| Thr | Arg | Lys | Met | Gly | Met | Met | Lys | Lys | Lys | Ser | Glu | Glu | Lys | Pro | Arg | |
| | | | 105 | | | | 110 | | | | | 115 | | | | |
| TTT | CGG | AGC | ATT | GTG | CAT | GTT | GTT | CAA | GCT | GGA | ATT | TTT | GTG | GAA | AGA | 498 |
| Phe | Arg | Ser | Ile | Val | His | Val | Val | Gln | Ala | Gly | Ile | Phe | Val | Glu | Arg | |
| | | 120 | | | | | 125 | | | | | 130 | | | | |
| ATG | TAC | AGA | AAG | TCC | TAT | CAC | ATG | GTT | GGC | TTG | GCA | TAT | CCA | GAG | GCT | 546 |
| Met | Tyr | Arg | Lys | Ser | Tyr | His | Met | Val | Gly | Leu | Ala | Tyr | Pro | Glu | Ala | |
| | 135 | | | | | 140 | | | | | 145 | | | | | |
| GTC | ATA | GTA | ACA | TTA | AAG | GAT | GTT | GAT | AAA | TGG | TCT | TTT | GAT | GTA | TTT | 594 |
| Val | Ile | Val | Thr | Leu | Lys | Asp | Val | Asp | Lys | Trp | Ser | Phe | Asp | Val | Phe | |
| 150 | | | | | 155 | | | | | 160 | | | | | 165 | |
| GCC | TTG | AAT | GAA | GCA | AGT | GGA | GAA | CAC | AGT | CTG | AAG | TTT | ATG | ATT | TAT | 642 |
| Ala | Leu | Asn | Glu | Ala | Ser | Gly | Glu | His | Ser | Leu | Lys | Phe | Met | Ile | Tyr | |
| | | | | | 170 | | | | | 175 | | | | | 180 | |
| GAA | CTA | TTC | ACC | AGA | TAT | GAT | CTT | ATC | AAC | CGT | TTC | AAG | ATT | CCT | GTT | 690 |
| Glu | Leu | Phe | Thr | Arg | Tyr | Asp | Leu | Ile | Asn | Arg | Phe | Lys | Ile | Pro | Val | |
| | | | 185 | | | | | 190 | | | | 195 | | | | |
| TCT | TGC | CTA | ATT | GCC | TTT | GCA | GAA | GCT | CTA | GAA | GTT | GGT | TAC | AGC | AAG | 738 |
| Ser | Cys | Leu | Ile | Ala | Phe | Ala | Glu | Ala | Leu | Glu | Val | Gly | Tyr | Ser | Lys | |
| | | 200 | | | | | 205 | | | | | 210 | | | | |
| TAC | AAA | AAT | CCA | TAC | CAC | AAT | TTG | ATT | CAT | GCA | GCT | GAT | GTC | ACT | CAA | 786 |
| Tyr | Lys | Asn | Pro | Tyr | His | Asn | Leu | Ile | His | Ala | Ala | Asp | Val | Thr | Gln | |
| | 215 | | | | | 220 | | | | | 225 | | | | | |
| ACT | GTG | CAT | TAC | ATA | ATG | CTT | CAT | ACA | GGT | ATC | ATG | CAC | TGG | CTC | ACT | 834 |
| Thr | Val | His | Tyr | Ile | Met | Leu | His | Thr | Gly | Ile | Met | His | Trp | Leu | Thr | |
| 230 | | | | | 235 | | | | | 240 | | | | | 245 | |
| GAA | CTG | GAA | ATT | TTA | GCA | ATG | GTC | TTT | GCC | GCT | GCC | ATT | CAT | GAC | TAT | 882 |
| Glu | Leu | Glu | Ile | Leu | Ala | Met | Val | Phe | Ala | Ala | Ala | Ile | His | Asp | Tyr | |
| | | | | 250 | | | | | 255 | | | | | 260 | | |
| GAG | CAT | ACA | GGG | ACT | ACA | AAC | AAT | TTT | CAC | ATT | CAG | ACA | AGG | TCA | GAT | 930 |
| Glu | His | Thr | Gly | Thr | Thr | Asn | Asn | Phe | His | Ile | Gln | Thr | Arg | Ser | Asp | |
| | | | 265 | | | | 270 | | | | | 275 | | | | |
| GTT | GCC | ATT | TTG | TAT | AAT | GAT | CGC | TCT | GTC | CTT | GAA | AAT | CAT | CAT | GTG | 978 |
| Val | Ala | Ile | Leu | Tyr | Asn | Asp | Arg | Ser | Val | Leu | Glu | Asn | His | His | Val | |
| | | 280 | | | | | 285 | | | | | 290 | | | | |
| AGT | GCA | GCT | TAT | CGC | CTT | ATG | CAA | GAA | GAA | GAA | ATG | AAT | GTC | CTG | ATA | 1026 |
| Ser | Ala | Ala | Tyr | Arg | Leu | Met | Gln | Glu | Glu | Glu | Met | Asn | Val | Leu | Ile | |
| | 295 | | | | | 300 | | | | | 305 | | | | | |
| AAT | TTA | TCC | AAA | GAT | GAC | TGG | AGG | GAT | CTT | CGG | AAC | CTA | GTG | ATT | GAA | 1074 |
| Asn | Leu | Ser | Lys | Asp | Asp | Trp | Arg | Asp | Leu | Arg | Asn | Leu | Val | Ile | Glu | |
| 310 | | | | | 315 | | | | | 320 | | | | | 325 | |
| ATG | GTG | TTG | TCT | ACA | GAC | ATG | TCG | GGT | CAC | TTC | CAG | CAA | ATT | AAA | AAT | 1122 |
| Met | Val | Leu | Ser | Thr | Asp | Met | Ser | Gly | His | Phe | Gln | Gln | Ile | Lys | Asn | |
| | | | | 330 | | | | | 335 | | | | | 340 | | |
| ATA | AGA | AAT | AGT | TTG | CAG | CAA | CCT | GAA | GGG | CTT | GAC | AAA | GCC | AAA | ACC | 1170 |
| Ile | Arg | Asn | Ser | Leu | Gln | Gln | Pro | Glu | Gly | Leu | Asp | Lys | Ala | Lys | Thr | |
| | | | 345 | | | | | 350 | | | | | 355 | | | |

| | | | | | | | | | | | | | | | | |
|---|---|---|---|---|---|---|---|---|---|---|---|---|---|---|---|---|
| ATG | TCC | CTG | ATT | CTC | CAT | GCA | GCA | GAC | ATC | AGT | CAC | CCA | GCC | AAA | TCC | 1218 |
| Met | Ser | Leu | Ile | Leu | His | Ala | Ala | Asp | Ile | Ser | His | Pro | Ala | Lys | Ser | |
| | | 360 | | | | | 365 | | | | | 370 | | | | |
| TGG | AAG | CTG | CAC | CAC | CGA | TGG | ACC | ATG | GCC | CTA | ATG | GAG | GAG | TTT | TTC | 1266 |
| Trp | Lys | Leu | His | His | Arg | Trp | Thr | Met | Ala | Leu | Met | Glu | Glu | Phe | Phe | |
| | 375 | | | | | 380 | | | | | 385 | | | | | |
| CTA | CAG | GGA | GAT | AAA | GAA | GCT | GAA | TTA | GGG | CTT | CCA | TTT | TCC | CCG | CTT | 1314 |
| Leu | Gln | Gly | Asp | Lys | Glu | Ala | Glu | Leu | Gly | Leu | Pro | Phe | Ser | Pro | Leu | |
| 390 | | | | | 395 | | | | | 400 | | | | | 405 | |
| TGC | GAT | CGG | AAG | TCA | ACG | ATG | GTG | GCC | CAG | TCC | CAA | ATA | GGT | TTC | ATT | 1362 |
| Cys | Asp | Arg | Lys | Ser | Thr | Met | Val | Ala | Gln | Ser | Gln | Ile | Gly | Phe | Ile | |
| | | | | 410 | | | | | 415 | | | | | 420 | | |
| GAT | TTC | ATA | GTA | GAA | CCA | ACA | TTT | TCT | CTT | CTG | ACA | GAC | TCA | ACA | GAG | 1410 |
| Asp | Phe | Ile | Val | Glu | Pro | Thr | Phe | Ser | Leu | Leu | Thr | Asp | Ser | Thr | Glu | |
| | | | 425 | | | | | 430 | | | | | 435 | | | |
| AAA | ATT | ATT | ATT | CCT | CTT | ATA | GAG | GAA | GAC | TCG | AAA | ACC | AAA | ACT | CCT | 1458 |
| Lys | Ile | Ile | Ile | Pro | Leu | Ile | Glu | Glu | Asp | Ser | Lys | Thr | Lys | Thr | Pro | |
| | | | 440 | | | | | 445 | | | | | 450 | | | |
| TCC | TAT | GGA | GCA | AGC | AGA | CGA | TCA | AAT | ATG | AAA | GGC | ACC | ACC | AAT | GAT | 1506 |
| Ser | Tyr | Gly | Ala | Ser | Arg | Arg | Ser | Asn | Met | Lys | Gly | Thr | Thr | Asn | Asp | |
| | 455 | | | | | 460 | | | | | 465 | | | | | |
| GGA | ACC | TAC | TCC | CCC | GAC | TAC | TCC | CTT | GCC | AGC | GTG | GAC | CTG | AAG | AGC | 1554 |
| Gly | Thr | Tyr | Ser | Pro | Asp | Tyr | Ser | Leu | Ala | Ser | Val | Asp | Leu | Lys | Ser | |
| 470 | | | | | 475 | | | | | 480 | | | | | 485 | |
| TTC | AAA | AAC | AGC | CTG | GTG | GAC | ATC | ATC | CAG | CAG | AAC | AAA | GAG | AGG | TGG | 1602 |
| Phe | Lys | Asn | Ser | Leu | Val | Asp | Ile | Ile | Gln | Gln | Asn | Lys | Glu | Arg | Trp | |
| | | | | 490 | | | | | 495 | | | | | 500 | | |
| AAA | GAG | TTA | GCT | GCT | CAA | GGT | GAA | CCT | GAT | CCC | CAT | AAG | AAC | TCA | GAT | 1650 |
| Lys | Glu | Leu | Ala | Ala | Gln | Gly | Glu | Pro | Asp | Pro | His | Lys | Asn | Ser | Asp | |
| | | | 505 | | | | | 510 | | | | | 515 | | | |
| CTA | GTA | AAT | GCT | GAA | GAA | AAA | CAT | GCT | GAA | ACA | CAT | TCA | TAGGTCTGAA | | | 1699 |
| Leu | Val | Asn | Ala | Glu | Glu | Lys | His | Ala | Glu | Thr | His | Ser | | | | |
| | | 520 | | | | | 525 | | | | | 530 | | | | |

| | | | | | |
|---|---|---|---|---|---|
| ACACCTGAAA | GACGTCTTTC | ATTCTAAGGA | TGGGAGGAAA | CAAATTCACA | AGAAATCATG | 1759 |
| AAGACATATA | AAAGCTACAT | ATGCATAAAA | AACTCTGAAT | TCAGGTCCCC | ATGGCTGTCA | 1819 |
| CAAATGAATG | AACAGAACTC | CCAACCCCGC | CTTTTTTTAA | TATAATGAAA | GTGCCTTAGC | 1879 |
| ATGGTTGCAG | CTGTCACCAC | TACAGTGTTT | TACAGACGGT | TTCTACTGAG | CATCACAATA | 1939 |
| AAGAGAATCT | TGCATTACAA | AAAAAAGAAA | AAAATGTGGC | TCGCTTTTAA | GATGAAGCAT | 1999 |
| TTCCCAGTAT | TTCTGAGTCA | GTTGTAAGAT | TCTTAATCG | ATACTAATAG | TTTCACTAAT | 2059 |
| AGCCACTGTC | AGTGTCACGC | ACTGTGATGA | AATCTTATAC | TTAGTCCTTC | AACAGTTCCA | 2119 |
| GAGTTGTGAC | TGTGCTTAAT | AGTTTGCATA | TGAATTCTGG | ATAGAAATCA | AATCACAAAC | 2179 |
| TGCATAGAAA | TTTTAAAAAC | CAGCTCCATA | TTAAATTTTT | TTAAGATATT | GTCTTGTATT | 2239 |
| GAAACTCCAA | TACTTTGGCC | ACCTGATGCA | AAGAGCTGAC | TCATTTGAAA | CC | 2291 |

( 2 ) INFORMATION FOR SEQ ID NO:6:

( i ) SEQUENCE CHARACTERISTICS:
        ( A ) LENGTH: 530 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

| | | | | | | | | | | | | | | | |
|---|---|---|---|---|---|---|---|---|---|---|---|---|---|---|---|
| Met | Gly | Ser | Thr | Ala | Thr | Glu | Thr | Glu | Glu | Leu | Glu | Asn | Thr | Thr | Phe |
| 1 | | | | 5 | | | | | 10 | | | | | 15 | |
| Lys | Tyr | Leu | Ile | Gly | Glu | Gln | Thr | Glu | Lys | Met | Trp | Gln | Arg | Leu | Lys |

```
                     20                          25                            30
Gly  Ile  Leu  Arg  Cys  Leu  Val  Lys  Gln  Leu  Glu  Lys  Gly  Asp  Val  Asn
               35                      40                      45

Val  Ile  Asp  Leu  Lys  Lys  Asn  Ile  Glu  Tyr  Ala  Ala  Ser  Val  Leu  Glu
          50                      55                      60

Ala  Val  Tyr  Ile  Asp  Glu  Thr  Arg  Arg  Leu  Leu  Asp  Thr  Asp  Asp  Glu
65                            70                      75                      80

Leu  Ser  Asp  Ile  Gln  Ser  Asp  Ser  Val  Pro  Ser  Glu  Val  Arg  Asp  Trp
                    85                      90                          95

Leu  Ala  Ser  Thr  Phe  Thr  Arg  Lys  Met  Gly  Met  Met  Lys  Lys  Lys  Ser
               100                     105                    110

Glu  Glu  Lys  Pro  Arg  Phe  Arg  Ser  Ile  Val  His  Val  Val  Gln  Ala  Gly
               115                     120                    125

Ile  Phe  Val  Glu  Arg  Met  Tyr  Arg  Lys  Ser  Tyr  His  Met  Val  Gly  Leu
     130                     135                    140

Ala  Tyr  Pro  Glu  Ala  Val  Ile  Val  Thr  Leu  Lys  Asp  Val  Asp  Lys  Trp
145                           150                    155                     160

Ser  Phe  Asp  Val  Phe  Ala  Leu  Asn  Glu  Ala  Ser  Gly  Glu  His  Ser  Leu
                    165                     170                    175

Lys  Phe  Met  Ile  Tyr  Glu  Leu  Phe  Thr  Arg  Tyr  Asp  Leu  Ile  Asn  Arg
               180                     185                    190

Phe  Lys  Ile  Pro  Val  Ser  Cys  Leu  Ile  Ala  Phe  Ala  Glu  Ala  Leu  Glu
          195                     200                    205

Val  Gly  Tyr  Ser  Lys  Tyr  Lys  Asn  Pro  Tyr  His  Asn  Leu  Ile  His  Ala
     210                     215                    220

Ala  Asp  Val  Thr  Gln  Thr  Val  His  Tyr  Ile  Met  Leu  His  Thr  Gly  Ile
225                           230                    235                     240

Met  His  Trp  Leu  Thr  Glu  Leu  Glu  Ile  Leu  Ala  Met  Val  Phe  Ala  Ala
                    245                     250                    255

Ala  Ile  His  Asp  Tyr  Glu  His  Thr  Gly  Thr  Thr  Asn  Asn  Phe  His  Ile
               260                     265                    270

Gln  Thr  Arg  Ser  Asp  Val  Ala  Ile  Leu  Tyr  Asn  Asp  Arg  Ser  Val  Leu
          275                     280                    285

Glu  Asn  His  His  Val  Ser  Ala  Ala  Tyr  Arg  Leu  Met  Gln  Glu  Glu  Glu
     290                     295                    300

Met  Asn  Val  Leu  Ile  Asn  Leu  Ser  Lys  Asp  Asp  Trp  Arg  Asp  Leu  Arg
305                           310                    315                     320

Asn  Leu  Val  Ile  Glu  Met  Val  Leu  Ser  Thr  Asp  Met  Ser  Gly  His  Phe
                    325                     330                    335

Gln  Gln  Ile  Lys  Asn  Ile  Arg  Asn  Ser  Leu  Gln  Gln  Pro  Glu  Gly  Leu
               340                     345                    350

Asp  Lys  Ala  Lys  Thr  Met  Ser  Leu  Ile  Leu  His  Ala  Ala  Asp  Ile  Ser
          355                     360                    365

His  Pro  Ala  Lys  Ser  Trp  Lys  Leu  His  His  Arg  Trp  Thr  Met  Ala  Leu
     370                     375                    380

Met  Glu  Glu  Phe  Phe  Leu  Gln  Gly  Asp  Lys  Glu  Ala  Glu  Leu  Gly  Leu
385                           390                    395                     400

Pro  Phe  Ser  Pro  Leu  Cys  Asp  Arg  Lys  Ser  Thr  Met  Val  Ala  Gln  Ser
                    405                     410                    415

Gln  Ile  Gly  Phe  Ile  Asp  Phe  Ile  Val  Glu  Pro  Thr  Phe  Ser  Leu  Leu
               420                     425                    430

Thr  Asp  Ser  Thr  Glu  Lys  Ile  Ile  Ile  Pro  Leu  Ile  Glu  Glu  Asp  Ser
          435                     440                    445
```

-continued

| Lys | Thr | Lys | Thr | Pro | Ser | Tyr | Gly | Ala | Ser | Arg | Arg | Ser | Asn | Met | Lys |
|     | 450 |     |     |     | 455 |     |     |     |     |     | 460 |     |     |     |     |
| Gly | Thr | Thr | Asn | Asp | Gly | Thr | Tyr | Ser | Pro | Asp | Tyr | Ser | Leu | Ala | Ser |
| 465 |     |     |     |     | 470 |     |     |     | 475 |     |     |     |     |     | 480 |
| Val | Asp | Leu | Lys | Ser | Phe | Lys | Asn | Ser | Leu | Val | Asp | Ile | Ile | Gln | Gln |
|     |     |     |     | 485 |     |     |     |     | 490 |     |     |     |     | 495 |     |
| Asn | Lys | Glu | Arg | Trp | Lys | Glu | Leu | Ala | Ala | Gln | Gly | Glu | Pro | Asp | Pro |
|     |     |     | 500 |     |     |     |     | 505 |     |     |     |     | 510 |     |     |
| His | Lys | Asn | Ser | Asp | Leu | Val | Asn | Ala | Glu | Glu | Lys | His | Ala | Glu | Thr |
|     |     |     | 515 |     |     |     | 520 |     |     |     |     | 525 |     |     |     |
| His | Ser |
|     | 530 |

( 2 ) INFORMATION FOR SEQ ID NO:7:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:7:

Met Asp Asp His Val Thr Ile
1               5

( 2 ) INFORMATION FOR SEQ ID NO:8:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:8:

ATGAGRAGRC AYGTHACNAT    20

( 2 ) INFORMATION FOR SEQ ID NO:9:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:9:

Leu Arg Cys Leu Val Lys Gln
1               5

( 2 ) INFORMATION FOR SEQ ID NO:10:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( i v ) ANTI-SENSE: YES ( x i ) SEQUENCE DESCRIPTION: SEQ ID NO:10:

CTGCTTCACT AAGCATCTTA G    21

( 2 ) INFORMATION FOR SEQ ID NO:11:

( i ) SEQUENCE CHARACTERISTICS:
    ( A ) LENGTH: 75 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:11:

ATGAGAAGGC ACGTAACGAT CAGGAGGAAA CATCTCCAAA GACCCATCTT TAGACTAAGA    60

TGCTTAGTGA AGCAG    75

( 2 ) INFORMATION FOR SEQ ID NO:12:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:12:

ATGGAYGAYC ACGTAACGAT C    21

( 2 ) INFORMATION FOR SEQ ID NO:13:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: DNA ( i v ) ANTI-SENSE: YES ( x i ) SEQUENCE DESCRIPTION: SEQ ID NO:13:

AAGTATCTCA TTGGAGAACA G    21

( 2 ) INFORMATION FOR SEQ ID NO:14:

( i ) SEQUENCE CHARACTERISTICS:
    ( A ) LENGTH: 54 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:14:

ATGGATGATC ACGTAACGAT CAGGAGGAAA CATCTCCAAA GACCCATCTT TAGA    54

( 2 ) INFORMATION FOR SEQ ID NO:15:

( i ) SEQUENCE CHARACTERISTICS:
    ( A ) LENGTH: 18 amino acids
    ( B ) TYPE: amino acid
    ( D ) TOPOLOGY: linear ( i i ) MOLECULE TYPE: protein ( x i ) SEQUENCE DESCRIPTION: SEQ ID NO:15:

Met Asp Asp His Val Thr Ile Arg Arg Lys His Leu Gln Arg Pro Ile
 1               5                  10                  15
Phe Arg ( 2 ) INFORMATION FOR SEQ ID NO:16:

( i ) SEQUENCE CHARACTERISTICS:
        ( A ) LENGTH: 2656 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 136..1677

( x i ) SEQUENCE DESCRIPTION: SEQ ID NO:16:

```
TTGCTGTCGA GAGAAAGAGG AAACTACTTT TGCCTTCTGG GCTCCTTGCA GGACAATAGA          60

TCAGGATAAG CTTCCACATT CTCTCCCTGG ATTTCTGGAG TGGTTTCCAG GAACAAGCTA         120

AACTTTCACC TTTAA ATG GAT GAC CAT GTC ACA ATC AGG AGG AAA CAT CTC         171
                Met Asp Asp His Val Thr Ile Arg Arg Lys His Leu
                 1               5                       10

CAA AGA CCC ATC TTT AGA CTA AGA TGC TTA GTG AAG CAG CTG GAA AAA          219
Gln Arg Pro Ile Phe Arg Leu Arg Cys Leu Val Lys Gln Leu Glu Lys
         15                  20                  25

GGT GAT GTT AAC GTC ATC GAC TTA AAG AAG AAT ATT GAA TAT GCA GCA          267
Gly Asp Val Asn Val Ile Asp Leu Lys Lys Asn Ile Glu Tyr Ala Ala
     30                  35                  40

TCT GTG TTG GAA GCA GTT TAT ATT GAT GAA ACA AGG AGA CTG CTG GAC          315
Ser Val Leu Glu Ala Val Tyr Ile Asp Glu Thr Arg Arg Leu Leu Asp
 45                  50                  55                  60

ACC GAT GAT GAG CTC AGT GAC ATT CAG TCG GAT TCC GTC CCA TCA GAA          363
Thr Asp Asp Glu Leu Ser Asp Ile Gln Ser Asp Ser Val Pro Ser Glu
                 65                  70                  75

GTC CGG GAC TGG TTG GCT TCT ACC TTT ACA CGG AAA ATG GGG ATG ATG          411
Val Arg Asp Trp Leu Ala Ser Thr Phe Thr Arg Lys Met Gly Met Met
             80                  85                  90

AAA AAG AAA TCT GAG GAA AAA CCA AGA TTT CGG AGC ATT GTG CAT GTT          459
Lys Lys Lys Ser Glu Glu Lys Pro Arg Phe Arg Ser Ile Val His Val
         95                  100                 105

GTT CAA GCT GGA ATT TTT GTG GAA AGA ATG TAC AGA AAG TCC TAT CAC          507
Val Gln Ala Gly Ile Phe Val Glu Arg Met Tyr Arg Lys Ser Tyr His
     110                 115                 120

ATG GTT GGC TTG GCA TAT CCA GAG GCT GTC ATA GTA ACA TTA AAG GAT          555
Met Val Gly Leu Ala Tyr Pro Glu Ala Val Ile Val Thr Leu Lys Asp
125                 130                 135                 140

GTT GAT AAA TGG TCT TTT GAT GTA TTT GCC TTG AAT GAA GCA AGT GGA          603
Val Asp Lys Trp Ser Phe Asp Val Phe Ala Leu Asn Glu Ala Ser Gly
                145                 150                 155

GAA CAC AGT CTG AAG TTT ATG ATT TAT GAA CTA TTC ACC AGA TAT GAT          651
Glu His Ser Leu Lys Phe Met Ile Tyr Glu Leu Phe Thr Arg Tyr Asp
            160                 165                 170

CTT ATC AAC CGT TTC AAG ATT CCT GTT TCT TGC CTA ATT GCC TTT GCA          699
Leu Ile Asn Arg Phe Lys Ile Pro Val Ser Cys Leu Ile Ala Phe Ala
        175                 180                 185

GAA GCT CTA GAA GTT GGT TAC AGC AAG TAC AAA AAT CCA TAC CAC AAT          747
Glu Ala Leu Glu Val Gly Tyr Ser Lys Tyr Lys Asn Pro Tyr His Asn
    190                 195                 200

TTG ATT CAT GCA GCT GAT GTC ACT CAA ACT GTG CAT TAC ATA ATG CTT          795
Leu Ile His Ala Ala Asp Val Thr Gln Thr Val His Tyr Ile Met Leu
205                 210                 215                 220

CAT ACA GGT ATC ATG CAC TGG CTC ACT GAA CTG GAA ATT TTA GCA ATG          843
His Thr Gly Ile Met His Trp Leu Thr Glu Leu Glu Ile Leu Ala Met
```

```
                     225                          230                          235
GTC TTT GCC GCT GCC ATT CAT GAC TAT GAG CAT ACA GGG ACT ACA AAC              891
Val Phe Ala Ala Ala Ile His Asp Tyr Glu His Thr Gly Thr Thr Asn
            240                  245                  250

AAT TTT CAC ATT CAG ACA AGG TCA GAT GTT GCC ATT TTG TAT AAT GAT              939
Asn Phe His Ile Gln Thr Arg Ser Asp Val Ala Ile Leu Tyr Asn Asp
        255                  260                  265

CGC TCT GTC CTT GAA AAT CAT CAT GTG AGT GCA GCT TAT CGC CTT ATG              987
Arg Ser Val Leu Glu Asn His His Val Ser Ala Ala Tyr Arg Leu Met
    270                  275                  280

CAA GAA GAA GAA ATG AAT GTC CTG ATA AAT TTA TCC AAA GAT GAC TGG             1035
Gln Glu Glu Glu Met Asn Val Leu Ile Asn Leu Ser Lys Asp Asp Trp
285                  290                  295                  300

AGG GAT CTT CGG AAC CTA GTG ATT GAA ATG GTG TTG TCT ACA GAC ATG             1083
Arg Asp Leu Arg Asn Leu Val Ile Glu Met Val Leu Ser Thr Asp Met
                305                  310                  315

TCG GGT CAC TTC CAG CAA ATT AAA AAT ATA AGA AAT AGT TTG CAG CAA             1131
Ser Gly His Phe Gln Gln Ile Lys Asn Ile Arg Asn Ser Leu Gln Gln
            320                  325                  330

CCT GAA GGG CTT GAC AAA GCC AAA ACC ATG TCC CTG ATT CTC CAT GCA             1179
Pro Glu Gly Leu Asp Lys Ala Lys Thr Met Ser Leu Ile Leu His Ala
        335                  340                  345

GCA GAC ATC AGT CAC CCA GCC AAA TCC TGG AAG CTG CAC CAC CGA TGG             1227
Ala Asp Ile Ser His Pro Ala Lys Ser Trp Lys Leu His His Arg Trp
    350                  355                  360

ACC ATG GCC CTA ATG GAG GAG TTT TTC CTA CAG GGA GAT AAA GAA GCT             1275
Thr Met Ala Leu Met Glu Glu Phe Phe Leu Gln Gly Asp Lys Glu Ala
365                  370                  375                  380

GAA TTA GGG CTT CCA TTT TCC CCG CTT TGC GAT CGG AAG TCA ACG ATG             1323
Glu Leu Gly Leu Pro Phe Ser Pro Leu Cys Asp Arg Lys Ser Thr Met
                385                  390                  395

GTG GCC CAG TCC CAA ATA GGT TTC ATT GAT TTC ATA GTA GAA CCA ACA             1371
Val Ala Gln Ser Gln Ile Gly Phe Ile Asp Phe Ile Val Glu Pro Thr
            400                  405                  410

TTT TCT CTT CTG ACA GAC TCA ACA GAG AAA ATT ATT ATT CCT CTT ATA             1419
Phe Ser Leu Leu Thr Asp Ser Thr Glu Lys Ile Ile Ile Pro Leu Ile
        415                  420                  425

GAG GAA GAC TCG AAA ACC AAA ACT CCT TCC TAT GGA GCA AGC AGA CGA             1467
Glu Glu Asp Ser Lys Thr Lys Thr Pro Ser Tyr Gly Ala Ser Arg Arg
    430                  435                  440

TCA AAT ATG AAA GGC ACC ACC AAT GAT GGA ACC TAC TCC CCC GAC TAC             1515
Ser Asn Met Lys Gly Thr Thr Asn Asp Gly Thr Tyr Ser Pro Asp Tyr
445                  450                  455                  460

TCC CTT GCC AGC GTG GAC CTG AAG AGC TTC AAA AAC AGC CTG GTG GAC             1563
Ser Leu Ala Ser Val Asp Leu Lys Ser Phe Lys Asn Ser Leu Val Asp
                465                  470                  475

ATC ATC CAG CAG AAC AAA GAG AGG TGG AAA GAG TTA GCT GCT CAA GGT             1611
Ile Ile Gln Gln Asn Lys Glu Arg Trp Lys Glu Leu Ala Ala Gln Gly
            480                  485                  490

GAA CCT GAT CCC CAT AAG AAC TCA GAT CTA GTA AAT GCT GAA GAA AAA             1659
Glu Pro Asp Pro His Lys Asn Ser Asp Leu Val Asn Ala Glu Glu Lys
        495                  500                  505

CAT GCT GAA ACA CAT TCA TAGGTCTGAA ACACCTGAAA GACGTCTTTC                    1707
His Ala Glu Thr His Ser
510

ATTCTAAGGA TGGGAGAGTG CTGTAACTAC AAAACTTTCA AGCTTCTAAG TAAAAGGAAA           1767

GCAAAAACAA AATTACAGAA AAATATTTTT GCAGCTCTGA GGCTATTTAG ATTGTCCTTG           1827

TTGTTTTAAA TACATGGGAA CCAAGTGAGA AGAGGGGCTG CTCAGAAGTT GTAGTCGAAG           1887
```

| | | | | | |
|---|---|---|---|---|---|
| TCCTAAGACA | ACAATGAAGC | ATCAGAGCCC | TGACTCTGTG | ACCTGATGAA | CTCTTCGTTG | 1947 |
| TAACTCTCAA | GCTGGGAAAC | CACAGCGAAT | CCTGTTCCTG | AAAGCAGTGA | ACCAGCCTGC | 2007 |
| ATCCACCACT | GTTATTGCAA | AGCACGAAAG | CATCACCCAC | GTGGGGGTCA | TCACAATGCA | 2067 |
| AGTCACGCAA | GACCTATGAC | CAAGATGACA | AGAACCTCCA | GCCCTTGTTG | GAGACAGACA | 2127 |
| CTAGAACTGA | GAGTGGGATT | TGCCTTCTGG | GGTGTTAATC | CCATCAGGAT | GTAACAAAAT | 2187 |
| ATATTACAGG | TCAAGGGATA | AGGGACAAGA | AGTGTGTGTC | TGTGTGTGTG | TGTGTGTATG | 2247 |
| TGCGCGCACT | CAAAAATGTC | TGTGAAAATG | GAAGCCCACA | CTCTTCTGCA | CAGAGAGCAT | 2307 |
| TATTTGATGT | GATTTATAAT | TTTACTACAA | ACAAACGAAC | TGCAGCCATT | GGAGACTGCT | 2367 |
| TCCTTGTCAT | GTTTGCCTG | AGCATGTGCA | GAGCCTTGCC | TTTGTTCCAA | ATTGAAGAAC | 2427 |
| TACCTTTATT | TGTTATTAGC | TGCCAAGAAA | GGTCAAGCCC | AAGTAGGTGT | TGTCATTTTC | 2487 |
| ACCGTACAAA | CTCTTCAATG | ATTGTTAGAC | TAAAGGAATT | TGTTTTGTG | AAAGGTAGAA | 2547 |
| ATTAGATGGA | AAAGATCAAG | AGTAGTCATC | AATTAAAGAA | GAAAGTGAAG | GTGGATATGT | 2607 |
| CCATCCTAAT | GAGTTTTCTG | TTGCACCTGC | TTCTTCCCTG | CGACAGCAA | | 2656 |

( 2 ) INFORMATION FOR SEQ ID NO:17:

( i ) SEQUENCE CHARACTERISTICS:
        ( A ) LENGTH: 514 amino acids
        ( B ) TYPE: amino acid
        ( D ) TOPOLOGY: linear ( i i ) MOLECULE TYPE: protein ( x i ) SEQUENCE DESCRIPTION: SEQ ID NO:17:

```
Met  Asp  Asp  His  Val  Thr  Ile  Arg  Arg  Lys  His  Leu  Gln  Arg  Pro  Ile
 1                  5                      10                      15

Phe  Arg  Leu  Arg  Cys  Leu  Val  Lys  Gln  Leu  Glu  Lys  Gly  Asp  Val  Asn
              20                      25                      30

Val  Ile  Asp  Leu  Lys  Lys  Asn  Ile  Glu  Tyr  Ala  Ala  Ser  Val  Leu  Glu
         35                      40                      45

Ala  Val  Tyr  Ile  Asp  Glu  Thr  Arg  Arg  Leu  Leu  Asp  Thr  Asp  Asp  Glu
     50                      55                      60

Leu  Ser  Asp  Ile  Gln  Ser  Asp  Ser  Val  Pro  Ser  Glu  Val  Arg  Asp  Trp
 65                      70                      75                      80

Leu  Ala  Ser  Thr  Phe  Thr  Arg  Lys  Met  Gly  Met  Met  Lys  Lys  Lys  Ser
              85                      90                      95

Glu  Glu  Lys  Pro  Arg  Phe  Arg  Ser  Ile  Val  His  Val  Gln  Ala  Gly
                 100                     105                    110

Ile  Phe  Val  Glu  Arg  Met  Tyr  Arg  Lys  Ser  Tyr  His  Met  Val  Gly  Leu
             115                     120                    125

Ala  Tyr  Pro  Glu  Ala  Val  Ile  Val  Thr  Leu  Lys  Asp  Val  Asp  Lys  Trp
     130                     135                    140

Ser  Phe  Asp  Val  Phe  Ala  Leu  Asn  Glu  Ala  Ser  Gly  Glu  His  Ser  Leu
145                     150                     155                    160

Lys  Phe  Met  Ile  Tyr  Glu  Leu  Phe  Thr  Arg  Tyr  Asp  Leu  Ile  Asn  Arg
              165                     170                    175

Phe  Lys  Ile  Pro  Val  Ser  Cys  Leu  Ile  Ala  Phe  Ala  Glu  Ala  Leu  Glu
             180                     185                    190

Val  Gly  Tyr  Ser  Lys  Tyr  Lys  Asn  Pro  Tyr  His  Asn  Leu  Ile  His  Ala
             195                     200                    205

Ala  Asp  Val  Thr  Gln  Thr  Val  His  Tyr  Ile  Met  Leu  His  Thr  Gly  Ile
     210                     215                     220
```

```
Met  His  Trp  Leu  Thr  Glu  Leu  Glu  Ile  Leu  Ala  Met  Val  Phe  Ala  Ala
225                      230                      235                     240

Ala  Ile  His  Asp  Tyr  Glu  His  Thr  Gly  Thr  Thr  Asn  Asn  Phe  His  Ile
                    245                      250                     255

Gln  Thr  Arg  Ser  Asp  Val  Ala  Ile  Leu  Tyr  Asn  Asp  Arg  Ser  Val  Leu
               260                      265                     270

Glu  Asn  His  His  Val  Ser  Ala  Ala  Tyr  Arg  Leu  Met  Gln  Glu  Glu  Glu
          275                      280                     285

Met  Asn  Val  Leu  Ile  Asn  Leu  Ser  Lys  Asp  Asp  Trp  Arg  Asp  Leu  Arg
     290                      295                     300

Asn  Leu  Val  Ile  Glu  Met  Val  Leu  Ser  Thr  Asp  Met  Ser  Gly  His  Phe
305                      310                      315                     320

Gln  Gln  Ile  Lys  Asn  Ile  Arg  Asn  Ser  Leu  Gln  Gln  Pro  Glu  Gly  Leu
               325                      330                     335

Asp  Lys  Ala  Lys  Thr  Met  Ser  Leu  Ile  Leu  His  Ala  Ala  Asp  Ile  Ser
               340                      345                     350

His  Pro  Ala  Lys  Ser  Trp  Lys  Leu  His  His  Arg  Trp  Thr  Met  Ala  Leu
               355                      360                     365

Met  Glu  Glu  Phe  Phe  Leu  Gln  Gly  Asp  Lys  Glu  Ala  Glu  Leu  Gly  Leu
370                      375                      380

Pro  Phe  Ser  Pro  Leu  Cys  Asp  Arg  Lys  Ser  Thr  Met  Val  Ala  Gln  Ser
385                      390                      395                     400

Gln  Ile  Gly  Phe  Ile  Asp  Phe  Ile  Val  Glu  Pro  Thr  Phe  Ser  Leu  Leu
               405                      410                     415

Thr  Asp  Ser  Thr  Glu  Lys  Ile  Ile  Ile  Pro  Leu  Ile  Glu  Glu  Asp  Ser
               420                      425                     430

Lys  Thr  Lys  Thr  Pro  Ser  Tyr  Gly  Ala  Ser  Arg  Arg  Ser  Asn  Met  Lys
          435                      440                     445

Gly  Thr  Thr  Asn  Asp  Gly  Thr  Tyr  Ser  Pro  Asp  Tyr  Ser  Leu  Ala  Ser
     450                      455                     460

Val  Asp  Leu  Lys  Ser  Phe  Lys  Asn  Ser  Leu  Val  Asp  Ile  Ile  Gln  Gln
465                      470                      475                     480

Asn  Lys  Glu  Arg  Trp  Lys  Glu  Leu  Ala  Ala  Gln  Gly  Glu  Pro  Asp  Pro
                    485                      490                     495

His  Lys  Asn  Ser  Asp  Leu  Val  Asn  Ala  Glu  Glu  Lys  His  Ala  Glu  Thr
               500                      505                     510

His  Ser
```

( 2 ) INFORMATION FOR SEQ ID NO:18:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:18:

ATHCAYGAYT AYGARCAYAC NGG     23

( 2 ) INFORMATION FOR SEQ ID NO:19:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:19:

```
Ile His Asp Tyr Glu His Thr Gly
1               5
```

( 2 ) INFORMATION FOR SEQ ID NO:20:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:20:

TCYTTRTCNC CYTGNCGRAA RAAYTCYTCC AT          32

( 2 ) INFORMATION FOR SEQ ID NO:21:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:21:

```
Met Glu Glu Phe Phe Arg Gln Gly Asp Lys Glu
1               5                   10
```

( 2 ) INFORMATION FOR SEQ ID NO:22:

( i ) SEQUENCE CHARACTERISTICS:
        ( A ) LENGTH: 412 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..412

( x i ) SEQUENCE DESCRIPTION: SEQ ID NO:22:

```
ATT CAT GAT TAT AAC ACA CGG GGC ACT ACC AAC AGC TTC CAC ATC CAG      48
Ile His Asp Tyr Asn Thr Arg Gly Thr Thr Asn Ser Phe His Ile Gln
 1               5                  10                  15

ACC AAA TCG GAA TGC GCC ATC CTG TAC AAC GAC CGC TCA GTG CTG GAG      96
Thr Lys Ser Glu Cys Ala Ile Leu Tyr Asn Asp Arg Ser Val Leu Glu
             20                  25                  30

AAT CAC CAC ATC AGC TCG GTT TTC CGA ATG ATG CAG GAC GAC GAC ATG     144
Asn His His Ile Ser Ser Val Phe Arg Met Met Gln Asp Asp Asp Met
         35                  40                  45

AAC ATC TTC ATC AAC CTC ACC AAG GAT GAG TTT GTA GAG CTG CGG GCT     192
Asn Ile Phe Ile Asn Leu Thr Lys Asp Glu Phe Val Glu Leu Arg Ala
     50                  55                  60

CTG GTC ATT GAG ATG GTG TTG GCC ACA GAC ATG TCC TGC CAT TTC CAG     240
Leu Val Ile Glu Met Val Leu Ala Thr Asp Met Ser Cys His Phe Gln
 65                  70                  75                  80

CAA GTG AAG TCC ATG AAG ACA GCC TTG CAG CAG CTG GAG AGG ATT GAC     288
Gln Val Lys Ser Met Lys Thr Ala Leu Gln Gln Leu Glu Arg Ile Asp
             85                  90                  95

AAG TCC AAG GCC CTC TCT CTG CTG CTT CAT GCT GCT GAC ATC AGC CAC     336
Lys Ser Lys Ala Leu Ser Leu Leu Leu His Ala Ala Asp Ile Ser His
            100                 105                 110
```

| | | | | | | | | | | | | | | | |
|---|---|---|---|---|---|---|---|---|---|---|---|---|---|---|---|
| CCC | ACC | AAG | CAG | TGG | TCG | GTT | CAC | AGC | CGC | TGG | ACC | AAG | GCC | CTC | ATG |
| Pro | Thr | Lys | Gln | Trp | Ser | Val | His | Ser | Arg | Trp | Thr | Lys | Ala | Leu | Met |
| | | 115 | | | | | 120 | | | | | 125 | | | |

384

| | | | | | | | |
|---|---|---|---|---|---|---|---|
| GAG | GAG | TTC | TTC | CGA | CAA | GGG | GAC | AAA | G |
| Glu | Glu | Phe | Phe | Arg | Gln | Gly | Asp | Lys |
| | 130 | | | | | 135 | | |

412

( 2 ) INFORMATION FOR SEQ ID NO:23:

( i ) SEQUENCE CHARACTERISTICS:
        ( A ) LENGTH: 137 amino acids
        ( B ) TYPE: amino acid
        ( D ) TOPOLOGY: linear ( i i ) MOLECULE TYPE: protein ( x i ) SEQUENCE DESCRIPTION: SEQ ID NO:23:

```
Ile His Asp Tyr Asn Thr Arg Gly Thr Thr Asn Ser Phe His Ile Gln
 1               5                  10                  15

Thr Lys Ser Glu Cys Ala Ile Leu Tyr Asn Asp Arg Ser Val Leu Glu
                20                  25                  30

Asn His His Ile Ser Ser Val Phe Arg Met Met Gln Asp Asp Met
            35                  40                  45

Asn Ile Phe Ile Asn Leu Thr Lys Asp Glu Phe Val Glu Leu Arg Ala
        50                  55                  60

Leu Val Ile Glu Met Val Leu Ala Thr Asp Met Ser Cys His Phe Gln
65                  70                  75                  80

Gln Val Lys Ser Met Lys Thr Ala Leu Gln Gln Leu Glu Arg Ile Asp
                85                  90                  95

Lys Ser Lys Ala Leu Ser Leu Leu Leu His Ala Ala Asp Ile Ser His
                100                 105                 110

Pro Thr Lys Gln Trp Ser Val His Ser Arg Trp Thr Lys Ala Leu Met
            115                 120                 125

Glu Glu Phe Phe Arg Gln Gly Asp Lys
    130                 135
```

( 2 ) INFORMATION FOR SEQ ID NO:24:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:24:

AARAARAAYY TNGARTAYAC NGC

23

( 2 ) INFORMATION FOR SEQ ID NO:25:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:25:

```
Lys Lys Asn Leu Glu Tyr Thr Ala
 1               5
```

( 2 ) INFORMATION FOR SEQ ID NO:26:

( i ) SEQUENCE CHARACTERISTICS:
    ( A ) LENGTH: 1844 base pairs
    ( B ) TYPE: nucleic acid
    ( C ) STRANDEDNESS: single
    ( D ) TOPOLOGY: linear ( i i ) MOLECULE TYPE: cDNA ( i x ) FEATURE:
    ( A ) NAME/KEY: CDS
    ( B ) LOCATION: 114..1715

( x i ) SEQUENCE DESCRIPTION: SEQ ID NO:26:

| | | | | | | |
|---|---|---|---|---|---|---|
| GGCTGGGCAG | CGGGAAAGGA | GGAGCCGCAG | GAACTGCAGC | TCTGCCAGCT | TGGGCCGAGC | 60 |
| TTTAGAGACC | CCCGGCCTGG | CTGGTCCCTG | CCAGCCGCAG | ACGGAGGCTG | AGC ATG<br>Met<br>1 | 116 |

```
GAG CTG TCC CCC CGC AGC CCT CCC GAG ATG CTA GAG TCG GAC TGC CCT        164
Glu Leu Ser Pro Arg Ser Pro Pro Glu Met Leu Glu Ser Asp Cys Pro
              5                  10                 15

TCA CCC CTG GAG CTG AAG TCA GCC CCC AGC AAG AAG ATG TGG ATT AAG        212
Ser Pro Leu Glu Leu Lys Ser Ala Pro Ser Lys Lys Met Trp Ile Lys
     20                  25                  30

CTC CGG TCT CTG CTG CGC TAC ATG GTG AAG CAG TTG GAG AAC GGG GAG        260
Leu Arg Ser Leu Leu Arg Tyr Met Val Lys Gln Leu Glu Asn Gly Glu
 35                  40                  45

GTA AAC ATT GAG GAG CTG AAG AAA AAC CTG GAG TAC ACA GCT TCT CTG        308
Val Asn Ile Glu Glu Leu Lys Lys Asn Leu Glu Tyr Thr Ala Ser Leu
 50                  55                  60                  65

CTG GAG GCC GTC TAT ATA GAT GAG ACT CGG CAA ATC CTG GAC ACG GAG        356
Leu Glu Ala Val Tyr Ile Asp Glu Thr Arg Gln Ile Leu Asp Thr Glu
         70                  75                  80

GAT GAG CTG CAG GAG CTG CGG TCT GAT GCG GTG CCT TCA GAG GTG CGG        404
Asp Glu Leu Gln Glu Leu Arg Ser Asp Ala Val Pro Ser Glu Val Arg
             85                  90                  95

GAC TGG CTG GCC TCC ACC TTC ACC CAG CAG ACC CGG GCC AAA GGC CCG        452
Asp Trp Leu Ala Ser Thr Phe Thr Gln Gln Thr Arg Ala Lys Gly Pro
         100                 105                 110

AGC GAA GAG AAG CCC AAG TTC CGG AGC ATC GTG CAC GCG GTG CAG GCT        500
Ser Glu Glu Lys Pro Lys Phe Arg Ser Ile Val His Ala Val Gln Ala
 115                 120                 125

GGC ATC TTT GTG GAG CGG ATG TTC CGG AGA ACG TAC ACC TCT GTG GGC        548
Gly Ile Phe Val Glu Arg Met Phe Arg Arg Thr Tyr Thr Ser Val Gly
130                 135                 140                 145

CCC ACC TAC TCC ACT GCC GTC CTC AAC TGT CTC AAG AAC GTG GAC CTT        596
Pro Thr Tyr Ser Thr Ala Val Leu Asn Cys Leu Lys Asn Val Asp Leu
         150                 155                 160

TGG TGC TTT GAT GTC TTT TCC TTG AAC CGG GCA GCA GAT GAC CAC GCC        644
Trp Cys Phe Asp Val Phe Ser Leu Asn Arg Ala Ala Asp Asp His Ala
         165                 170                 175

CTG AGG ACC ATC GTT TTT GAG CTG CTG ACT CGG CAC AAC CTC ATC AGC        692
Leu Arg Thr Ile Val Phe Glu Leu Leu Thr Arg His Asn Leu Ile Ser
         180                 185                 190

CGC TTT AAG ATT CCC ACT GTG TTT TTG ATG ACT TTC CTG GAT GCC TTG        740
Arg Phe Lys Ile Pro Thr Val Phe Leu Met Thr Phe Leu Asp Ala Leu
 195                 200                 205

GAG ACA GGC TAC GGA AAG TAC AAG AAC CCT TAC CAC AAC CAG ATC CAC        788
Glu Thr Gly Tyr Gly Lys Tyr Lys Asn Pro Tyr His Asn Gln Ile His
210                 215                 220                 225

GCA GCT GAC GTC ACC CAG ACG GTC CAC TGC TTC TTG CTC CGC ACA GGG        836
Ala Ala Asp Val Thr Gln Thr Val His Cys Phe Leu Leu Arg Thr Gly
         230                 235                 240
```

-continued

| | | | | | | | | | | | | | | | | |
|---|---|---|---|---|---|---|---|---|---|---|---|---|---|---|---|---|
| ATG | GTG | CAC | TGC | CTG | TCG | GAG | ATT | GAG | GTC | CTG | GCC | ATC | ATC | TTT | GCT | 884 |
| Met | Val | His | Cys | Leu | Ser | Glu | Ile | Glu | Val | Leu | Ala | Ile | Ile | Phe | Ala | |
| | | | 245 | | | | | 250 | | | | | 255 | | | |
| GCA | GCG | ATC | CAC | GAC | TAT | GAG | CAC | ACT | GGC | ACT | ACC | AAC | AGC | TTC | CAC | 932 |
| Ala | Ala | Ile | His | Asp | Tyr | Glu | His | Thr | Gly | Thr | Thr | Asn | Ser | Phe | His | |
| | | 260 | | | | | 265 | | | | | 270 | | | | |
| ATC | CAG | ACC | AAA | TCG | GAA | TGC | GCC | ATC | CTG | TAC | AAC | GAC | CGC | TCA | GTG | 980 |
| Ile | Gln | Thr | Lys | Ser | Glu | Cys | Ala | Ile | Leu | Tyr | Asn | Asp | Arg | Ser | Val | |
| | 275 | | | | | 280 | | | | | 285 | | | | | |
| CTG | GAG | AAT | CAC | CAC | ATC | AGC | TCG | GTT | TTC | CGA | ATG | ATG | CAG | GAC | GAC | 1028 |
| Leu | Glu | Asn | His | His | Ile | Ser | Ser | Val | Phe | Arg | Met | Met | Gln | Asp | Asp | |
| 290 | | | | | 295 | | | | | 300 | | | | | 305 | |
| GAG | ATG | AAC | ATC | TTC | ATC | AAC | CTC | ACC | AAG | GAT | GAG | TTT | GTA | GAG | CTG | 1076 |
| Glu | Met | Asn | Ile | Phe | Ile | Asn | Leu | Thr | Lys | Asp | Glu | Phe | Val | Glu | Leu | |
| | | | | 310 | | | | | 315 | | | | | 320 | | |
| CGG | GCT | CTG | GTC | ATT | GAG | ATG | GTG | TTG | GCC | ACA | GAC | ATG | TCC | TGC | CAT | 1124 |
| Arg | Ala | Leu | Val | Ile | Glu | Met | Val | Leu | Ala | Thr | Asp | Met | Ser | Cys | His | |
| | | | 325 | | | | | 330 | | | | | 335 | | | |
| TTC | CAG | CAA | GTG | AAG | TCC | ATG | AAG | ACA | GCC | TTG | CAG | CAG | CTG | GAG | AGG | 1172 |
| Phe | Gln | Gln | Val | Lys | Ser | Met | Lys | Thr | Ala | Leu | Gln | Gln | Leu | Glu | Arg | |
| | | 340 | | | | | 345 | | | | | 350 | | | | |
| ATT | GAC | AAG | TCC | AAG | GCC | CTC | TCT | CTG | CTG | CTT | CAT | GCT | GCT | GAC | ATC | 1220 |
| Ile | Asp | Lys | Ser | Lys | Ala | Leu | Ser | Leu | Leu | Leu | His | Ala | Ala | Asp | Ile | |
| | 355 | | | | | 360 | | | | | 365 | | | | | |
| AGC | CAC | CCC | ACC | AAG | CAG | TGG | TCG | GTT | CAC | AGC | CGC | TGG | ACC | AAG | GCC | 1268 |
| Ser | His | Pro | Thr | Lys | Gln | Trp | Ser | Val | His | Ser | Arg | Trp | Thr | Lys | Ala | |
| 370 | | | | | 375 | | | | | 380 | | | | | 385 | |
| CTC | ATG | GAG | GAA | TTC | TTC | CGC | CAG | GGT | GAC | AAG | GAG | GCT | GAG | CTG | GGC | 1316 |
| Leu | Met | Glu | Glu | Phe | Phe | Arg | Gln | Gly | Asp | Lys | Glu | Ala | Glu | Leu | Gly | |
| | | | | 390 | | | | | 395 | | | | | 400 | | |
| CTG | CCC | TTT | TCT | CCG | CTC | TGT | GAC | CGC | ACT | TCC | ACC | CTC | GTG | GCG | CAG | 1364 |
| Leu | Pro | Phe | Ser | Pro | Leu | Cys | Asp | Arg | Thr | Ser | Thr | Leu | Val | Ala | Gln | |
| | | | 405 | | | | | 410 | | | | | 415 | | | |
| TCC | CAG | ATT | GGT | TTC | ATC | GAC | TTC | ATT | GTG | GAG | CCC | ACG | TTC | TCT | GTG | 1412 |
| Ser | Gln | Ile | Gly | Phe | Ile | Asp | Phe | Ile | Val | Glu | Pro | Thr | Phe | Ser | Val | |
| | | 420 | | | | | 425 | | | | | 430 | | | | |
| CTC | ACC | GAT | GTG | GCT | GAG | AAG | AGT | GTC | CAG | CCC | ACC | GGG | GAC | GAC | GAC | 1460 |
| Leu | Thr | Asp | Val | Ala | Glu | Lys | Ser | Val | Gln | Pro | Thr | Gly | Asp | Asp | Asp | |
| | 435 | | | | | 440 | | | | | 445 | | | | | |
| TCG | AAG | TCT | AAA | AAC | CAG | CCC | AGC | TTC | CAG | TGG | CGC | CAG | CCT | TCT | CTG | 1508 |
| Ser | Lys | Ser | Lys | Asn | Gln | Pro | Ser | Phe | Gln | Trp | Arg | Gln | Pro | Ser | Leu | |
| 450 | | | | | 455 | | | | | 460 | | | | | 465 | |
| GAT | GTA | GAA | GTG | GGA | GAC | CCC | AAC | CCT | GAC | GTG | GTC | AGC | TTC | CGC | TCC | 1556 |
| Asp | Val | Glu | Val | Gly | Asp | Pro | Asn | Pro | Asp | Val | Val | Ser | Phe | Arg | Ser | |
| | | | | 470 | | | | | 475 | | | | | 480 | | |
| ACC | TGG | ACC | AAA | TAC | ATT | CAG | GAG | AAC | AAG | CAG | AAA | TGG | AAG | GAA | CGG | 1604 |
| Thr | Trp | Thr | Lys | Tyr | Ile | Gln | Glu | Asn | Lys | Gln | Lys | Trp | Lys | Glu | Arg | |
| | | | 485 | | | | | 490 | | | | | 495 | | | |
| GCG | GCG | AGC | GGC | ATC | ACC | AAC | CAG | ATG | TCC | ATT | GAC | GAA | CTG | TCC | CCT | 1652 |
| Ala | Ala | Ser | Gly | Ile | Thr | Asn | Gln | Met | Ser | Ile | Asp | Glu | Leu | Ser | Pro | |
| | | 500 | | | | | 505 | | | | | 510 | | | | |
| TGT | GAG | GAA | GAG | GCC | CCA | GCC | TCC | CCT | GCC | GAA | GAC | GAG | CAC | AAC | CAG | 1700 |
| Cys | Glu | Glu | Glu | Ala | Pro | Ala | Ser | Pro | Ala | Glu | Asp | Glu | His | Asn | Gln | |
| | 515 | | | | | 520 | | | | | 525 | | | | | |
| AAC | GGG | AAT | CTG | GAC | TAGCGGGGCC | TGGCCAGGTC | CTCACTGAGT | CCTGAGTGTT | | | | | | | | 1755 |
| Asn | Gly | Asn | Leu | Asp | | | | | | | | | | | | |
| 530 | | | | | | | | | | | | | | | | |

CGATGTCATC AGCACCATCC ATCGGGACTG GCTCCCCCAT CTGCTCCGAG GGCGAATGGA   1815

TGTCAAGGAA CAGAAAACCC ACCCGAAGA                                      1844

( 2 ) INFORMATION FOR SEQ ID NO:27:

( i ) SEQUENCE CHARACTERISTICS:
        ( A ) LENGTH: 534 amino acids
        ( B ) TYPE: amino acid
        ( D ) TOPOLOGY: linear ( i i ) MOLECULE TYPE: protein ( x i ) SEQUENCE DESCRIPTION: SEQ ID NO:27:

```
Met Glu Leu Ser Pro Arg Ser Pro Pro Glu Met Leu Glu Ser Asp Cys
  1               5                  10                  15
Pro Ser Pro Leu Glu Leu Lys Ser Ala Pro Ser Lys Lys Met Trp Ile
             20                  25                  30
Lys Leu Arg Ser Leu Leu Arg Tyr Met Val Lys Gln Leu Glu Asn Gly
         35                  40                  45
Glu Val Asn Ile Glu Glu Leu Lys Lys Asn Leu Glu Tyr Thr Ala Ser
     50                  55                  60
Leu Leu Glu Ala Val Tyr Ile Asp Glu Thr Arg Gln Ile Leu Asp Thr
 65                  70                  75                  80
Glu Asp Glu Leu Gln Glu Leu Arg Ser Asp Ala Val Pro Ser Glu Val
                 85                  90                  95
Arg Asp Trp Leu Ala Ser Thr Phe Thr Gln Gln Thr Arg Ala Lys Gly
            100                 105                 110
Pro Ser Glu Glu Lys Pro Lys Phe Arg Ser Ile Val His Ala Val Gln
        115                 120                 125
Ala Gly Ile Phe Val Glu Arg Met Phe Arg Arg Thr Tyr Thr Ser Val
    130                 135                 140
Gly Pro Thr Tyr Ser Thr Ala Val Leu Asn Cys Leu Lys Asn Val Asp
145                 150                 155                 160
Leu Trp Cys Phe Asp Val Phe Ser Leu Asn Arg Ala Ala Asp Asp His
                165                 170                 175
Ala Leu Arg Thr Ile Val Phe Glu Leu Leu Thr Arg His Asn Leu Ile
            180                 185                 190
Ser Arg Phe Lys Ile Pro Thr Val Phe Leu Met Thr Phe Leu Asp Ala
        195                 200                 205
Leu Glu Thr Gly Tyr Gly Lys Tyr Lys Asn Pro Tyr His Asn Gln Ile
    210                 215                 220
His Ala Ala Asp Val Thr Gln Thr Val His Cys Phe Leu Leu Arg Thr
225                 230                 235                 240
Gly Met Val His Cys Leu Ser Glu Ile Glu Val Leu Ala Ile Ile Phe
                245                 250                 255
Ala Ala Ala Ile His Asp Tyr Glu His Thr Gly Thr Thr Asn Ser Phe
            260                 265                 270
His Ile Gln Thr Lys Ser Glu Cys Ala Ile Leu Tyr Asn Asp Arg Ser
        275                 280                 285
Val Leu Glu Asn His His Ile Ser Ser Val Phe Arg Met Met Gln Asp
    290                 295                 300
Asp Glu Met Asn Ile Phe Ile Asn Leu Thr Lys Asp Glu Phe Val Glu
305                 310                 315                 320
Leu Arg Ala Leu Val Ile Glu Met Val Leu Ala Thr Asp Met Ser Cys
                325                 330                 335
His Phe Gln Gln Val Lys Ser Met Lys Thr Ala Leu Gln Gln Leu Glu
            340                 345                 350
Arg Ile Asp Lys Ser Lys Ala Leu Ser Leu Leu Leu His Ala Ala Asp
```

```
                    355                        360                         365
Ile  Ser  His  Pro  Thr  Lys  Gln  Trp  Ser  Val  His  Ser  Arg  Trp  Thr  Lys
          370                        375                        380

Ala  Leu  Met  Glu  Glu  Phe  Phe  Arg  Gln  Gly  Asp  Lys  Glu  Ala  Glu  Leu
385                           390                         395                      400

Gly  Leu  Pro  Phe  Ser  Pro  Leu  Cys  Asp  Arg  Thr  Ser  Thr  Leu  Val  Ala
                    405                        410                        415

Gln  Ser  Gln  Ile  Gly  Phe  Ile  Asp  Phe  Ile  Val  Glu  Pro  Thr  Phe  Ser
               420                        425                        430

Val  Leu  Thr  Asp  Val  Ala  Glu  Lys  Ser  Val  Gln  Pro  Thr  Gly  Asp  Asp
               435                        440                        445

Asp  Ser  Lys  Ser  Lys  Asn  Gln  Pro  Ser  Phe  Gln  Trp  Arg  Gln  Pro  Ser
     450                        455                        460

Leu  Asp  Val  Glu  Val  Gly  Asp  Pro  Asn  Pro  Asp  Val  Val  Ser  Phe  Arg
465                           470                        475                      480

Ser  Thr  Trp  Thr  Lys  Tyr  Ile  Gln  Glu  Asn  Lys  Gln  Lys  Trp  Lys  Glu
                    485                        490                        495

Arg  Ala  Ala  Ser  Gly  Ile  Thr  Asn  Gln  Met  Ser  Ile  Asp  Glu  Leu  Ser
               500                        505                        510

Pro  Cys  Glu  Glu  Glu  Ala  Pro  Ala  Ser  Pro  Ala  Glu  Asp  Glu  His  Asn
          515                        520                        525

Gln  Asn  Gly  Asn  Leu  Asp
          530
```

(2) INFORMATION FOR SEQ ID NO:28:

(i) SEQUENCE CHARACTERISTICS:
    (A) LENGTH: 14 amino acids
    (B) TYPE: amino acid
    (D) TOPOLOGY: linear (ii) MOLECULE TYPE: peptide (xi) SEQUENCE DESCRIPTION: SEQ ID NO:28:

```
Gln  Leu  Glu  Asn  Gly  Glu  Val  Asn  Ile  Glu  Glu  Leu  Lys  Lys
1                   5                        10
```

(2) INFORMATION FOR SEQ ID NO:29:

(i) SEQUENCE CHARACTERISTICS:
    (A) LENGTH: 14 amino acids
    (B) TYPE: amino acid
    (D) TOPOLOGY: linear (ii) MOLECULE TYPE: peptide (xi) SEQUENCE DESCRIPTION: SEQ ID NO:29:

```
Gln  Leu  Ile  Pro  Gly  Arg  Val  Asn  Ile  Ile  Ser  Leu  Lys  Lys
1                   5                        10
```

(2) INFORMATION FOR SEQ ID NO:30:

(i) SEQUENCE CHARACTERISTICS:
    (A) LENGTH: 16 amino acids
    (B) TYPE: amino acid
    (D) TOPOLOGY: linear (ii) MOLECULE TYPE: peptide (xi) SEQUENCE DESCRIPTION: SEQ ID NO:30:

```
Lys  Ser  Glu  Cys  Ala  Ile  Leu  Tyr  Asn  Asp  Arg  Ser  Val  Leu  Glu  Asn
1                   5                        10                        15
```

( 2 ) INFORMATION FOR SEQ ID NO:31:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:31:

```
Lys Asp Glu Thr Ala Ile Leu Tyr Asn Asp Arg Thr Val Leu Glu Asn
 1               5                  10                  15
```

( 2 ) INFORMATION FOR SEQ ID NO:32:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:32:

```
GGATCCGGAT CCCGCAGACG GAGGCTGAGC ATGG                              34
```

( 2 ) INFORMATION FOR SEQ ID NO:33:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:33:

```
GGATCCGGAT CCAGGACCTG GCCAGGCCCG GC                                32
```

( 2 ) INFORMATION FOR SEQ ID NO:34:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:34:

```
Glu Met Met Met Tyr His Met Lys
 1               5
```

( 2 ) INFORMATION FOR SEQ ID NO:35:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:35:

```
Tyr His Asn Trp Met His Ala Phe
 1               5
```

( 2 ) INFORMATION FOR SEQ ID NO:36:

( i ) SEQUENCE CHARACTERISTICS:
        ( A ) LENGTH: 23 base pairs ( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:36:

TTCATRTGRT ACATCATCAT YTC     23

( 2 ) INFORMATION FOR SEQ ID NO:37:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:37:

AANGCRTGCA TCCARTTRTG RTA     23

( 2 ) INFORMATION FOR SEQ ID NO:38:

( i ) SEQUENCE CHARACTERISTICS:
( A ) LENGTH: 4131 base pairs
( B ) TYPE: nucleic acid
( C ) STRANDEDNESS: single
( D ) TOPOLOGY: linear ( i i ) MOLECULE TYPE: cDNA ( i x ) FEATURE:
( A ) NAME/KEY: CDS
( B ) LOCATION: 148..2910

( x i ) SEQUENCE DESCRIPTION: SEQ ID NO:38:

```
AGGCGCAGCG  GCCGGGCCGG  CGGGCGGGCG  GGCGGCTGCG  AGCATGGTCC  TGGTGCTGCA     60

CCACATCCTC  ATCGCTGTTG  TCCAATTCTT  CAGGCGGGGC  CAGCAGGTCT  TCCTCAAGCC    120

GGACGAGCCG  CCGCCGCCGC  CGCAGCC ATG CGC CGA CAG CCT GCA GCC AGC          171
                              Met Arg Arg Gln Pro Ala Ala Ser
                                1               5

CGG GAC CTC TTT GCA CAG GAG CCA GTG CCC CCA GGG AGT GGA GAC GGC          219
Arg Asp Leu Phe Ala Gln Glu Pro Val Pro Pro Gly Ser Gly Asp Gly
         10                  15                  20

GCA TTG CAG GAT GCT TTG CTG AGC CTG GGC TCC GTC ATC GAC GTT GCA          267
Ala Leu Gln Asp Ala Leu Leu Ser Leu Gly Ser Val Ile Asp Val Ala
 25                  30                  35                  40

GGC TTG CAA CAG GCT GTC AAG GAG GCC CTG TCG GCT GTG CTT CCC AAA          315
Gly Leu Gln Gln Ala Val Lys Glu Ala Leu Ser Ala Val Leu Pro Lys
                 45                  50                  55

GTG GAG ACG GTC TAC ACC TAC CTG CTG GAT GGG GAA TCC CGG CTG GTG          363
Val Glu Thr Val Tyr Thr Tyr Leu Leu Asp Gly Glu Ser Arg Leu Val
             60                  65                  70

TGT GAG GAG CCC CCC CAC GAG CTG CCC CAG GAG GGG AAA GTG CGA GAG          411
Cys Glu Glu Pro Pro His Glu Leu Pro Gln Glu Gly Lys Val Arg Glu
         75                  80                  85

GCT GTG ATC TCC CGG AAG CGG CTG GGC TGC AAT GGA CTG GGC CCC TCA          459
Ala Val Ile Ser Arg Lys Arg Leu Gly Cys Asn Gly Leu Gly Pro Ser
 90                  95                 100

GAC CTG CCT GGG AAG CCC TTG GCA AGG CTG GTG GCT CCA CTG GCT CCT          507
Asp Leu Pro Gly Lys Pro Leu Ala Arg Leu Val Ala Pro Leu Ala Pro
105                 110                 115                 120

GAC ACC CAA GTG CTG GTC ATA CCG CTG GTG GAC AAG GAG GCC GGG GCT          555
Asp Thr Gln Val Leu Val Ile Pro Leu Val Asp Lys Glu Ala Gly Ala
```

-continued

|     |     |     |     | 125 |     |     |     |     | 130 |     |     |     |     | 135 |     |      |
|-----|-----|-----|-----|-----|-----|-----|-----|-----|-----|-----|-----|-----|-----|-----|-----|------|
| GTG | GCA | GCT | GTC | ATC | TTG | GTG | CAC | TGT | GGT | CAG | CTG | AGT | GAC | AAT | GAG | 603  |
| Val | Ala | Ala | Val | Ile | Leu | Val | His | Cys | Gly | Gln | Leu | Ser | Asp | Asn | Glu |      |
|     |     |     | 140 |     |     |     |     | 145 |     |     |     |     | 150 |     |     |      |
| GAG | TGG | AGC | CTG | CAA | GCT | GTG | GAG | AAG | CAT | ACC | CTG | GTG | GCC | CTG | AAA | 651  |
| Glu | Trp | Ser | Leu | Gln | Ala | Val | Glu | Lys | His | Thr | Leu | Val | Ala | Leu | Lys |      |
|     |     | 155 |     |     |     |     | 160 |     |     |     |     | 165 |     |     |     |      |
| AGG | GTG | CAG | GCC | TTG | CAG | CAG | CGC | GAG | TCC | AGC | GTG | GCC | CCG | GAA | GCG | 699  |
| Arg | Val | Gln | Ala | Leu | Gln | Gln | Arg | Glu | Ser | Ser | Val | Ala | Pro | Glu | Ala |      |
|     | 170 |     |     |     |     | 175 |     |     |     |     | 180 |     |     |     |     |      |
| ACC | CAG | AAT | CCT | CCG | GAG | GAG | GCA | GCG | GGA | GAC | CAG | AAG | GGT | GGG | GTC | 747  |
| Thr | Gln | Asn | Pro | Pro | Glu | Glu | Ala | Ala | Gly | Asp | Gln | Lys | Gly | Gly | Val |      |
| 185 |     |     |     |     | 190 |     |     |     |     | 195 |     |     |     |     | 200 |      |
| GCA | TAC | ACA | AAC | CAA | GAC | CGA | AAG | ATC | CTG | CAG | CTT | TGC | GGG | GAG | CTC | 795  |
| Ala | Tyr | Thr | Asn | Gln | Asp | Arg | Lys | Ile | Leu | Gln | Leu | Cys | Gly | Glu | Leu |      |
|     |     |     |     | 205 |     |     |     |     | 210 |     |     |     |     | 215 |     |      |
| TAC | GAC | CTG | GAT | GCA | TCT | TCC | CTG | CAG | CTC | AAA | GTC | CTC | CAA | TAT | CTG | 843  |
| Tyr | Asp | Leu | Asp | Ala | Ser | Ser | Leu | Gln | Leu | Lys | Val | Leu | Gln | Tyr | Leu |      |
|     |     |     | 220 |     |     |     |     | 225 |     |     |     |     | 230 |     |     |      |
| CAA | CAG | GAG | ACC | CAG | GCA | TCC | CGC | TGC | TGC | CTG | CTG | CTG | GTA | TCC | GAG | 891  |
| Gln | Gln | Glu | Thr | Gln | Ala | Ser | Arg | Cys | Cys | Leu | Leu | Leu | Val | Ser | Glu |      |
|     |     | 235 |     |     |     |     | 240 |     |     |     |     | 245 |     |     |     |      |
| GAC | AAT | CTT | CAG | CTC | TCC | TGC | AAG | GTC | ATT | GGA | GAT | AAA | GTA | CTG | GAG | 939  |
| Asp | Asn | Leu | Gln | Leu | Ser | Cys | Lys | Val | Ile | Gly | Asp | Lys | Val | Leu | Glu |      |
|     | 250 |     |     |     |     | 255 |     |     |     |     | 260 |     |     |     |     |      |
| GAA | GAG | ATC | AGC | TTT | CCG | TTG | ACC | ACA | GGA | CGC | CTG | GGC | CAA | GTG | GTG | 987  |
| Glu | Glu | Ile | Ser | Phe | Pro | Leu | Thr | Thr | Gly | Arg | Leu | Gly | Gln | Val | Val |      |
| 265 |     |     |     |     | 270 |     |     |     |     | 275 |     |     |     |     | 280 |      |
| GAA | GAC | AAG | AAG | TCT | ATC | CAG | CTG | AAA | GAT | CTC | ACC | TCC | GAG | GAT | ATG | 1035 |
| Glu | Asp | Lys | Lys | Ser | Ile | Gln | Leu | Lys | Asp | Leu | Thr | Ser | Glu | Asp | Met |      |
|     |     |     |     | 285 |     |     |     |     | 290 |     |     |     |     | 295 |     |      |
| CAA | CAG | CTG | CAA | AGC | ATG | TTG | GGC | TGT | GAG | GTG | CAG | GCC | ATG | CTC | TGT | 1083 |
| Gln | Gln | Leu | Gln | Ser | Met | Leu | Gly | Cys | Glu | Val | Gln | Ala | Met | Leu | Cys |      |
|     |     |     | 300 |     |     |     |     | 305 |     |     |     |     | 310 |     |     |      |
| GTC | CCT | GTC | ATC | AGC | CGG | GCC | ACT | GAC | CAG | GTC | GTG | GCC | CTG | GCC | TGT | 1131 |
| Val | Pro | Val | Ile | Ser | Arg | Ala | Thr | Asp | Gln | Val | Val | Ala | Leu | Ala | Cys |      |
|     |     | 315 |     |     |     |     | 320 |     |     |     |     | 325 |     |     |     |      |
| GCC | TTC | AAC | AAG | CTC | GGA | GGA | GAC | TTG | TTC | ACA | GAC | CAG | GAC | GAG | CAC | 1179 |
| Ala | Phe | Asn | Lys | Leu | Gly | Gly | Asp | Leu | Phe | Thr | Asp | Gln | Asp | Glu | His |      |
|     | 330 |     |     |     |     | 335 |     |     |     |     | 340 |     |     |     |     |      |
| GTG | ATC | CAG | CAC | TGC | TTC | CAC | TAC | ACC | AGC | ACA | GTG | CTC | ACC | AGC | ACC | 1227 |
| Val | Ile | Gln | His | Cys | Phe | His | Tyr | Thr | Ser | Thr | Val | Leu | Thr | Ser | Thr |      |
| 345 |     |     |     |     | 350 |     |     |     |     | 355 |     |     |     |     | 360 |      |
| CTG | GCC | TTC | CAG | AAG | GAG | CAG | AAG | CTC | AAG | TGT | GAG | TGC | CAG | GCT | CTT | 1275 |
| Leu | Ala | Phe | Gln | Lys | Glu | Gln | Lys | Leu | Lys | Cys | Glu | Cys | Gln | Ala | Leu |      |
|     |     |     |     | 365 |     |     |     |     | 370 |     |     |     |     | 375 |     |      |
| CTC | CAA | GTG | GCG | AAG | AAC | CTC | TTC | ACT | CAT | CTG | GAT | GAC | GTC | TCC | GTG | 1323 |
| Leu | Gln | Val | Ala | Lys | Asn | Leu | Phe | Thr | His | Leu | Asp | Asp | Val | Ser | Val |      |
|     |     |     | 380 |     |     |     |     | 385 |     |     |     |     | 390 |     |     |      |
| CTG | CTC | CAG | GAG | ATC | ATC | ACA | GAG | GCC | AGG | AAC | CTC | AGC | AAT | GCT | GAG | 1371 |
| Leu | Leu | Gln | Glu | Ile | Ile | Thr | Glu | Ala | Arg | Asn | Leu | Ser | Asn | Ala | Glu |      |
|     |     | 395 |     |     |     |     | 400 |     |     |     |     | 405 |     |     |     |      |
| ATC | TGC | TCT | GTG | TTC | CTG | CTG | GAT | CAG | AAC | GAG | CTG | GTG | GCC | AAG | GTG | 1419 |
| Ile | Cys | Ser | Val | Phe | Leu | Leu | Asp | Gln | Asn | Glu | Leu | Val | Ala | Lys | Val |      |
|     | 410 |     |     |     |     | 415 |     |     |     |     | 420 |     |     |     |     |      |
| TTC | GAT | GGG | GGT | GTG | GTG | GAA | GAT | GAG | AGC | TAT | GAG | ATC | CGC | ATT | CCC | 1467 |
| Phe | Asp | Gly | Gly | Val | Val | Glu | Asp | Glu | Ser | Tyr | Glu | Ile | Arg | Ile | Pro |      |
| 425 |     |     |     |     | 430 |     |     |     |     | 435 |     |     |     |     | 440 |      |
| GCT | GAC | CAG | GGC | ATC | GCG | GGT | CAT | GTG | GCG | ACC | ACC | GGC | CAG | ATC | CTA | 1515 |
| Ala | Asp | Gln | Gly | Ile | Ala | Gly | His | Val | Ala | Thr | Thr | Gly | Gln | Ile | Leu |      |

-continued

```
                             445                          450                         455
AAC ATC CCA GAT GCT TAC GCA CAT CCG CTT TTC TAC CGA GGC GTG GAC    1563
Asn Ile Pro Asp Ala Tyr Ala His Pro Leu Phe Tyr Arg Gly Val Asp
            460                     465                     470

GAC AGC ACC GGC TTC CGG ACG CGC AAC ATC CTC TGC TTC CCC ATC AAG    1611
Asp Ser Thr Gly Phe Arg Thr Arg Asn Ile Leu Cys Phe Pro Ile Lys
        475                     480                     485

AAC GAG AAC CAG GAG GTC ATC GGT GTG GCC GAG CTG GTG AAC AAG ATC    1659
Asn Glu Asn Gln Glu Val Ile Gly Val Ala Glu Leu Val Asn Lys Ile
    490                     495                     500

AAT GGA CCA TGG TTC AGC AAG TTT GAT GAA GAC CTG GCT ACA GCC TTC    1707
Asn Gly Pro Trp Phe Ser Lys Phe Asp Glu Asp Leu Ala Thr Ala Phe
505                     510                     515                 520

TCC ATC TAC TGT GGC ATC AGC ATT GCC CAT TCC CTC CTA TAC AAG AAA    1755
Ser Ile Tyr Cys Gly Ile Ser Ile Ala His Ser Leu Leu Tyr Lys Lys
        525                     530                     535

GTG AAT GAG GCG CAG TAT CGC AGC CAC CTT GCC AAT GAG ATG ATG ATG    1803
Val Asn Glu Ala Gln Tyr Arg Ser His Leu Ala Asn Glu Met Met Met
        540                     545                     550

TAC CAC ATG AAG GTC TCT GAT GAC GAG TAC ACC AAA CTT CTC CAT GAC    1851
Tyr His Met Lys Val Ser Asp Asp Glu Tyr Thr Lys Leu Leu His Asp
        555                     560                     565

GGG ATC CAG CCT GTG GCT GCC ATC GAC TCC AAC TTT GCC AGT TTC ACA    1899
Gly Ile Gln Pro Val Ala Ala Ile Asp Ser Asn Phe Ala Ser Phe Thr
570                     575                     580

TAC ACT CCT CGC TCT CTG CCC GAG GAT GAC ACT TCC ATG GCC ATC CTG    1947
Tyr Thr Pro Arg Ser Leu Pro Glu Asp Asp Thr Ser Met Ala Ile Leu
585                     590                     595                 600

AGC ATG CTG CAG GAC ATG AAT TTC ATC AAT AAC TAC AAA ATT GAC TGC    1995
Ser Met Leu Gln Asp Met Asn Phe Ile Asn Asn Tyr Lys Ile Asp Cys
                605                     610                     615

CCG ACA CTG GCC CGG TTC TGT TTG ATG GTG AAG AAG GGC TAC CGG GAT    2043
Pro Thr Leu Ala Arg Phe Cys Leu Met Val Lys Lys Gly Tyr Arg Asp
            620                     625                     630

CCC CCC TAC CAC AAC TGG ATG CAC GCC TTT TCT GTC TCC CAC TTC TGC    2091
Pro Pro Tyr His Asn Trp Met His Ala Phe Ser Val Ser His Phe Cys
        635                     640                     645

TAC CTG CTC TAC AAG AAC CTG GAG CTC ACC AAC TAC CTC GAG GAC ATG    2139
Tyr Leu Leu Tyr Lys Asn Leu Glu Leu Thr Asn Tyr Leu Glu Asp Met
    650                     655                     660

GAG ATC TTT GCC TTG TTT ATT TCC TGC ATG TGT CAC GAC CTG GAC CAC    2187
Glu Ile Phe Ala Leu Phe Ile Ser Cys Met Cys His Asp Leu Asp His
665                     670                     675                 680

AGA GGC ACA AAC AAC TCC TTC CAG GTG GCC TCG AAA TCT GTG CTG GCC    2235
Arg Gly Thr Asn Asn Ser Phe Gln Val Ala Ser Lys Ser Val Leu Ala
                685                     690                     695

GCG CTC TAC AGC TCG GAA GGC TCT GTC ATG GAG AGG CAC CAC TTC GCT    2283
Ala Leu Tyr Ser Ser Glu Gly Ser Val Met Glu Arg His His Phe Ala
            700                     705                     710

CAG GCC ATT GCC ATC CTC AAC ACC CAC GGC TGC AAC ATC TTT GAC CAC    2331
Gln Ala Ile Ala Ile Leu Asn Thr His Gly Cys Asn Ile Phe Asp His
        715                     720                     725

TTC TCC CGG AAG GAT TAT CAG CGC ATG TTG GAC CTG ATG CGG GAC ATC    2379
Phe Ser Arg Lys Asp Tyr Gln Arg Met Leu Asp Leu Met Arg Asp Ile
        730                     735                     740

ATC TTG GCC ACA GAT CTG GCC CAC CAC CTC CGC ATC TTC AAG GAC CTC    2427
Ile Leu Ala Thr Asp Leu Ala His His Leu Arg Ile Phe Lys Asp Leu
745                     750                     755                 760

CAA AAG ATG GCC GAA GTG GGC TAT GAT CGA ACC AAC AAG CAG CAC CAC    2475
Gln Lys Met Ala Glu Val Gly Tyr Asp Arg Thr Asn Lys Gln His His
```

|  |  |  |  |  |  |  |  |  |  |  |  |  |  |  |  |  |
|---|---|---|---|---|---|---|---|---|---|---|---|---|---|---|---|---|
| AGC | CTC | CTT | CTC | TGC | CTC | CTT | ATG | ACC | TCC | TGT | GAC | CTC | TCT | GAC | CAG | 2523 |
| Ser | Leu | Leu | Leu<br>780 | Cys | Leu | Leu | Met | Thr<br>785 | Ser | Cys | Asp | Leu | Ser<br>790 | Asp | Gln | |
| ACC | AAG | GGC | TGG | AAG | ACC | ACG | AGG | AAG | ATC | GCG | GAG | CTG | ATC | TAC | AAA | 2571 |
| Thr | Lys | Gly<br>795 | Trp | Lys | Thr | Thr | Arg<br>800 | Lys | Ile | Ala | Glu | Leu<br>805 | Ile | Tyr | Lys | |
| GAG | TTC | TTC | TCC | CAG | GGA | GAC | TTG | GAG | AAG | GCC | ATG | GGC | AAC | AGG | CCG | 2619 |
| Glu | Phe<br>810 | Phe | Ser | Gln | Gly | Asp | Leu | Glu<br>815 | Lys | Ala | Met | Gly<br>820 | Asn | Arg | Pro | |
| ATG | GAG | ATG | ATG | GAC | CGT | GAG | AAG | GCC | TAC | ATC | CCC | GAG | CTG | CAG | ATC | 2667 |
| Met<br>825 | Glu | Met | Met | Asp | Arg<br>830 | Glu | Lys | Ala | Tyr | Ile<br>835 | Pro | Glu | Leu | Gln | Ile<br>840 | |
| AGC | TTC | ATG | GAG | CAC | ATC | GCA | ATG | CCC | ATC | TAC | AAG | CTG | CTG | CAA | GAC | 2715 |
| Ser | Phe | Met | Glu | His<br>845 | Ile | Ala | Met | Pro | Ile<br>850 | Tyr | Lys | Leu | Leu | Gln<br>855 | Asp | |
| CTG | TTC | CCC | AAG | GCG | GCC | GAG | TTG | TAC | GAA | CGC | GTG | GCC | TCT | AAT | CGT | 2763 |
| Leu | Phe | Pro | Lys<br>860 | Ala | Ala | Glu | Leu | Tyr<br>865 | Glu | Arg | Val | Ala | Ser<br>870 | Asn | Arg | |
| GAG | CAC | TGG | ACC | AAG | GTG | TCA | CAC | AAG | TTC | ACC | ATC | CGA | GGC | CTC | CCG | 2811 |
| Glu | His | Trp<br>875 | Thr | Lys | Val | Ser | His<br>880 | Lys | Phe | Thr | Ile | Arg<br>885 | Gly | Leu | Pro | |
| AGC | AAC | AAC | TCG | TTG | GAC | TTC | CTG | GAC | GAG | GAG | TAT | GAG | GTG | CCT | GAC | 2859 |
| Ser | Asn<br>890 | Asn | Ser | Leu | Asp | Phe<br>895 | Leu | Asp | Glu | Glu | Tyr<br>900 | Glu | Val | Pro | Asp | |
| CTG | GAT | GGC | GCT | AGG | GCT | CCC | ATC | AAT | GGC | TGT | TGC | AGC | CTT | GAT | GCT | 2907 |
| Leu<br>905 | Asp | Gly | Ala | Arg | Ala<br>910 | Pro | Ile | Asn | Gly | Cys<br>915 | Cys | Ser | Leu | Asp | Ala<br>920 | |
| GAG | TGAGTCCCTC | CTGGGACCCC | TCCCTGTCCA | GGCCTCCTCC | CACAAGCCTC | | | | | | | | | | | 2960 |
| Glu | | | | | | | | | | | | | | | | |

| | | | | |
|---|---|---|---|---|
| CACGGGCCTG | GCCGCACGCC | CTGGACCAG | AGCCAAGGGT | CCTGGATTCT | AGGCCAGGAC | 3020 |
| TTCCCATGTG | ACCCGGGCGA | GGTCTGACCT | TCCCGGGCCT | CAGCTTTCTT | GTCTGTATAA | 3080 |
| TGGAAGACTT | CAGCCTCACT | GAGACTTTGT | CACTTGTCCT | CTGAGAGCAC | AGGGGTAACC | 3140 |
| AATGAGCAGT | GGACCCTGCT | CTGCACCTCT | GACCGCATCT | TGGCAAGTCC | CCACCCTCCA | 3200 |
| GGCCACTCCT | TCTCTGAGGC | AGCCGGATGG | TTTCTTCTGG | GCCCCATTCC | TGCCCTACCA | 3260 |
| GACCTGTGCC | CTTTCCTGTG | GGGGCACCCT | CACTGGCTCC | CAGGATCCTC | AGGCAAGAAC | 3320 |
| ATGAGACATC | TGAGTGGGCA | AAGGGTGGGT | CTTAGAGACA | GTTATCAGCC | TGGCTGGAGG | 3380 |
| ACTAGAAGTA | GCCATGGGAC | CACCTGTGGC | CCAGAGGACT | GCCTTTGTAC | TTATGGTGGG | 3440 |
| GACTGGGACC | TGGGGATATA | AGGGTCCCAG | GAGGACACTG | CCAGGGGCC | AGTGCAGTGC | 3500 |
| TCTGGGGAGA | GGGGGCTCAG | GAAGAGAGGA | GGATAAGAAC | AGTGAGAAGG | AAGGATCCCT | 3560 |
| GGGTTGGGAG | GCAGGCCCAG | CATGGGTCAG | CCATGCTTCC | TCCTGGCTGT | GTGACCCTGG | 3620 |
| GCAAGTCCCT | TCCCCTCTCT | GCGAAACAGT | AGGGTGAGAC | AATCCATTCT | CTAAGACCCC | 3680 |
| TTTTAGATCC | AAGTCCCCAT | AGTTCTGTGG | AGTCCAGTA | GAGGCCACCG | AGGGTCCCTG | 3740 |
| GCCCCCTTGG | GCACAGAGCT | GACACTGAGT | CCCTCAGTGG | CCCCCTGAGT | ATACCCCCTT | 3800 |
| AGCCGGAGCC | CCTTCCCCAT | TCCTACAGCC | AGAGGGGGAC | CTGGCCTCAG | CCTGGCAGGG | 3860 |
| CCTCTCTCCT | CTTCAAGGCC | ATATCCACCT | GTGCCCCGGG | GCTTGGGAGA | CCCCCTAGGG | 3920 |
| CCGGAGCTCT | GGGGTCATCC | TGGCCACTGG | CTTCTCCTTT | CTCTGTTTTG | TTCTGTATGT | 3980 |
| GTTGTGGGGT | GGGGGAGGG | GGGCCACCTG | CCTTACCTAT | TCTGAGTTGC | CTTTAGAGAG | 4040 |
| ATGCGTTTTT | TCTAGGACTC | TGTGCAACTG | TTGTATATGG | TTCCGTGGGC | TGACCGCTTT | 4100 |
| GTACATGAGA | ATAAATCTAT | TTCTTTCTAC | C | | | 4131 |

(2) INFORMATION FOR SEQ ID NO:39:

(i) SEQUENCE CHARACTERISTICS:
        (A) LENGTH: 921 amino acids
        (B) TYPE: amino acid
        (D) TOPOLOGY: linear (ii) MOLECULE TYPE: protein (xi) SEQUENCE DESCRIPTION: SEQ ID NO:39:

```
Met Arg Arg Gln Pro Ala Ala Ser Arg Asp Leu Phe Ala Gln Glu Pro
 1               5                  10                  15

Val Pro Pro Gly Ser Gly Asp Gly Ala Leu Gln Asp Ala Leu Leu Ser
                20                  25                  30

Leu Gly Ser Val Ile Asp Val Ala Gly Leu Gln Gln Ala Val Lys Glu
            35                  40                  45

Ala Leu Ser Ala Val Leu Pro Lys Val Glu Thr Val Tyr Thr Tyr Leu
 50                  55                  60

Leu Asp Gly Glu Ser Arg Leu Val Cys Gln Glu Pro Pro His Glu Leu
 65                  70                  75                  80

Pro Gln Glu Gly Lys Val Arg Glu Ala Val Ile Ser Arg Lys Arg Leu
                85                  90                  95

Gly Cys Asn Gly Leu Gly Pro Ser Asp Leu Pro Gly Lys Pro Leu Ala
                100                 105                 110

Arg Leu Val Ala Pro Leu Ala Pro Asp Thr Gln Val Leu Val Ile Pro
            115                 120                 125

Leu Val Asp Lys Glu Ala Gly Ala Val Ala Ala Val Ile Leu Val His
 130                 135                 140

Cys Gly Gln Leu Ser Asp Asn Glu Glu Trp Ser Leu Gln Ala Val Glu
 145                 150                 155                 160

Lys His Thr Leu Val Ala Leu Lys Arg Val Gln Ala Leu Gln Gln Arg
                165                 170                 175

Glu Ser Ser Val Ala Pro Glu Ala Thr Gln Asn Pro Pro Glu Glu Ala
                180                 185                 190

Ala Gly Asp Gln Lys Gly Gly Val Ala Tyr Thr Asn Gln Asp Arg Lys
            195                 200                 205

Ile Leu Gln Leu Cys Gly Glu Leu Tyr Asp Leu Asp Ala Ser Ser Leu
 210                 215                 220

Gln Leu Lys Val Leu Gln Tyr Leu Gln Gln Glu Thr Gln Ala Ser Arg
 225                 230                 235                 240

Cys Cys Leu Leu Leu Val Ser Glu Asp Asn Leu Gln Leu Ser Cys Lys
                245                 250                 255

Val Ile Gly Asp Lys Val Leu Glu Glu Ile Ser Phe Pro Leu Thr
                260                 265                 270

Thr Gly Arg Leu Gly Gln Val Val Glu Asp Lys Lys Ser Ile Gln Leu
            275                 280                 285

Lys Asp Leu Thr Ser Glu Asp Met Gln Gln Leu Gln Ser Met Leu Gly
 290                 295                 300

Cys Glu Val Gln Ala Met Leu Cys Val Pro Val Ile Ser Arg Ala Thr
 305                 310                 315                 320

Asp Gln Val Val Ala Leu Ala Cys Ala Phe Asn Lys Leu Gly Gly Asp
                325                 330                 335

Leu Phe Thr Asp Gln Asp Glu His Val Ile Gln His Cys Phe His Tyr
            340                 345                 350

Thr Ser Thr Val Leu Thr Ser Thr Leu Ala Phe Gln Lys Glu Gln Lys
```

-continued

|     |     |     | 355 |     |     |     |     | 360 |     |     |     |     | 365 |     |     |
| --- | --- | --- | --- | --- | --- | --- | --- | --- | --- | --- | --- | --- | --- | --- | --- |
| Leu | Lys | Cys | Glu | Cys | Gln | Ala | Leu | Leu | Gln | Val | Ala | Lys | Asn | Leu | Phe |
|     | 370 |     |     |     | 375 |     |     |     |     | 380 |     |     |     |     |     |
| Thr | His | Leu | Asp | Asp | Val | Ser | Val | Leu | Leu | Gln | Glu | Ile | Ile | Thr | Glu |
| 385 |     |     |     | 390 |     |     |     |     | 395 |     |     |     |     |     | 400 |
| Ala | Arg | Asn | Leu | Ser | Asn | Ala | Glu | Ile | Cys | Ser | Val | Phe | Leu | Leu | Asp |
|     |     |     |     | 405 |     |     |     |     | 410 |     |     |     |     | 415 |     |
| Gln | Asn | Glu | Leu | Val | Ala | Lys | Val | Phe | Asp | Gly | Gly | Val | Val | Glu | Asp |
|     |     |     | 420 |     |     |     |     | 425 |     |     |     |     | 430 |     |     |
| Glu | Ser | Tyr | Glu | Ile | Arg | Ile | Pro | Ala | Asp | Gln | Gly | Ile | Ala | Gly | His |
|     |     | 435 |     |     |     |     | 440 |     |     |     |     | 445 |     |     |     |
| Val | Ala | Thr | Thr | Gly | Gln | Ile | Leu | Asn | Ile | Pro | Asp | Ala | Tyr | Ala | His |
|     | 450 |     |     |     |     | 455 |     |     |     |     | 460 |     |     |     |     |
| Pro | Leu | Phe | Tyr | Arg | Gly | Val | Asp | Asp | Ser | Thr | Gly | Phe | Arg | Thr | Arg |
| 465 |     |     |     |     | 470 |     |     |     |     | 475 |     |     |     |     | 480 |
| Asn | Ile | Leu | Cys | Phe | Pro | Ile | Lys | Asn | Glu | Asn | Gln | Glu | Val | Ile | Gly |
|     |     |     |     | 485 |     |     |     |     |     | 490 |     |     |     |     | 495 |
| Val | Ala | Glu | Leu | Val | Asn | Lys | Ile | Asn | Gly | Pro | Trp | Phe | Ser | Lys | Phe |
|     |     |     |     | 500 |     |     |     |     | 505 |     |     |     |     | 510 |     |
| Asp | Glu | Asp | Leu | Ala | Thr | Ala | Phe | Ser | Ile | Tyr | Cys | Gly | Ile | Ser | Ile |
|     |     | 515 |     |     |     |     | 520 |     |     |     |     | 525 |     |     |     |
| Ala | His | Ser | Leu | Leu | Tyr | Lys | Lys | Val | Asn | Glu | Ala | Gln | Tyr | Arg | Ser |
|     | 530 |     |     |     |     | 535 |     |     |     |     | 540 |     |     |     |     |
| His | Leu | Ala | Asn | Glu | Met | Met | Met | Tyr | His | Met | Lys | Val | Ser | Asp | Asp |
| 545 |     |     |     |     | 550 |     |     |     |     | 555 |     |     |     |     | 560 |
| Glu | Tyr | Thr | Lys | Leu | Leu | His | Asp | Gly | Ile | Gln | Pro | Val | Ala | Ala | Ile |
|     |     |     |     | 565 |     |     |     |     | 570 |     |     |     |     | 575 |     |
| Asp | Ser | Asn | Phe | Ala | Ser | Phe | Thr | Tyr | Thr | Pro | Arg | Ser | Leu | Pro | Glu |
|     |     |     | 580 |     |     |     |     | 585 |     |     |     |     | 590 |     |     |
| Asp | Asp | Thr | Ser | Met | Ala | Ile | Leu | Ser | Met | Leu | Gln | Asp | Met | Asn | Phe |
|     |     | 595 |     |     |     |     | 600 |     |     |     |     | 605 |     |     |     |
| Ile | Asn | Asn | Tyr | Lys | Ile | Asp | Cys | Pro | Thr | Leu | Ala | Arg | Phe | Cys | Leu |
|     | 610 |     |     |     |     | 615 |     |     |     |     | 620 |     |     |     |     |
| Met | Val | Lys | Lys | Gly | Tyr | Arg | Asp | Pro | Pro | Tyr | His | Asn | Trp | Met | His |
| 625 |     |     |     |     | 630 |     |     |     |     | 635 |     |     |     |     | 640 |
| Ala | Phe | Ser | Val | Ser | His | Phe | Cys | Tyr | Leu | Leu | Tyr | Lys | Asn | Leu | Glu |
|     |     |     |     | 645 |     |     |     |     | 650 |     |     |     |     | 655 |     |
| Leu | Thr | Asn | Tyr | Leu | Glu | Asp | Met | Glu | Ile | Phe | Ala | Leu | Phe | Ile | Ser |
|     |     |     |     | 660 |     |     |     |     | 665 |     |     |     |     | 670 |     |
| Cys | Met | Cys | His | Asp | Leu | Asp | His | Arg | Gly | Thr | Asn | Asn | Ser | Phe | Gln |
|     |     | 675 |     |     |     |     | 680 |     |     |     |     | 685 |     |     |     |
| Val | Ala | Ser | Lys | Ser | Val | Leu | Ala | Ala | Leu | Tyr | Ser | Ser | Glu | Gly | Ser |
|     | 690 |     |     |     |     | 695 |     |     |     |     | 700 |     |     |     |     |
| Val | Met | Glu | Arg | His | His | Phe | Ala | Gln | Ala | Ile | Ala | Ile | Leu | Asn | Thr |
| 705 |     |     |     |     | 710 |     |     |     |     | 715 |     |     |     |     | 720 |
| His | Gly | Cys | Asn | Ile | Phe | Asp | His | Phe | Ser | Arg | Lys | Asp | Tyr | Gln | Arg |
|     |     |     |     | 725 |     |     |     |     | 730 |     |     |     |     | 735 |     |
| Met | Leu | Asp | Leu | Met | Arg | Asp | Ile | Ile | Leu | Ala | Thr | Asp | Leu | Ala | His |
|     |     |     |     | 740 |     |     |     |     | 745 |     |     |     |     | 750 |     |
| His | Leu | Arg | Ile | Phe | Lys | Asp | Leu | Gln | Lys | Met | Ala | Glu | Val | Gly | Tyr |
|     |     |     | 755 |     |     |     |     | 760 |     |     |     |     | 765 |     |     |
| Asp | Arg | Thr | Asn | Lys | Gln | His | His | Ser | Leu | Leu | Leu | Cys | Leu | Leu | Met |
|     |     | 770 |     |     |     |     | 775 |     |     |     |     | 780 |     |     |     |

```
Thr  Ser  Cys  Asp  Leu  Ser  Asp  Gln  Thr  Lys  Gly  Trp  Lys  Thr  Thr  Arg
785                 790                      795                           800

Lys  Ile  Ala  Glu  Leu  Ile  Tyr  Lys  Glu  Phe  Phe  Ser  Gln  Gly  Asp  Leu
                    805                      810                      815

Glu  Lys  Ala  Met  Gly  Asn  Arg  Pro  Met  Glu  Met  Met  Asp  Arg  Glu  Lys
               820                      825                      830

Ala  Tyr  Ile  Pro  Glu  Leu  Gln  Ile  Ser  Phe  Met  Glu  His  Ile  Ala  Met
               835                      840                      845

Pro  Ile  Tyr  Lys  Leu  Leu  Gln  Asp  Leu  Phe  Pro  Lys  Ala  Ala  Glu  Leu
     850                      855                      860

Tyr  Glu  Arg  Val  Ala  Ser  Asn  Arg  Glu  His  Trp  Thr  Lys  Val  Ser  His
865                      870                      875                           880

Lys  Phe  Thr  Ile  Arg  Gly  Leu  Pro  Ser  Asn  Asn  Ser  Leu  Asp  Phe  Leu
                    885                      890                      895

Asp  Glu  Glu  Tyr  Glu  Val  Pro  Asp  Leu  Asp  Gly  Ala  Arg  Ala  Pro  Ile
               900                      905                      910

Asn  Gly  Cys  Cys  Ser  Leu  Asp  Ala  Glu
               915                 920
```

( 2 ) INFORMATION FOR SEQ ID NO:40:

( i ) SEQUENCE CHARACTERISTICS:
      ( A ) LENGTH: 249 base pairs
      ( B ) TYPE: nucleic acid
      ( C ) STRANDEDNESS: single
      ( D ) TOPOLOGY: linear ( i i ) MOLECULE TYPE: cDNA ( x i ) SEQUENCE DESCRIPTION: SEQ ID NO:40:

```
ATATCGAATT CGGTTTAGTC TGGTTGGGGA GGCAGACGAT GAGGAGCGAT GGGGCAGGCA        60
TGCGGCCACT CCATCCTCTG CAGGAGCCAG CAGTACCCGG CTGCGCGACC GGCTGAGCCG       120
CGGGGCCAGC AGGTCTTCCT CAAGCCGGAC GAGCCGCCGC CGCCGCCGCA GCCATGCGCC       180
GACAGCCTGC AGGATGCTTT GCTGAGCCTG GGCTCCGTCA TTGAGCTTGC AGGCTTGCGA       240
CAGGCTGTC                                                              249
```

( 2 ) INFORMATION FOR SEQ ID NO:41:

( i ) SEQUENCE CHARACTERISTICS:
      ( A ) LENGTH: 250 base pairs
      ( B ) TYPE: nucleic acid
      ( C ) STRANDEDNESS: single
      ( D ) TOPOLOGY: linear ( i i ) MOLECULE TYPE: cDNA ( i v ) ANTI-SENSE: YES ( x i ) SEQUENCE DESCRIPTION: SEQ ID NO:41:

```
GAATTCGGGT AGAGCAGGTA GCAGAAGTGG GAGACAGAAA AGGCGTGCAT CCAGTTGTGG        60
TAGGGGGGAT CCCGGTAGCC CTTCTTCACC ATCAAACAGA ACCGGGCCAG TGTCGGGCAG       120
TCAATTTTGT AGTTATTGAT GAAATTCATG TTCTGCAGCA TGCTCAGGAT GGCCATGGAG       180
TGTCATCCTT GGGCAGAGAG CGAGGAGTGT ATGTGAACTG GCAAGTTGGA GTCGATGGCA       240
GCCACAGGCT                                                             250
```

( 2 ) INFORMATION FOR SEQ ID NO:42:

( i ) SEQUENCE CHARACTERISTICS:
      ( A ) LENGTH: 3789 base pairs ( B ) TYPE: nucleic acid
( C ) STRANDEDNESS: single
( D ) TOPOLOGY: linear ( i i ) MOLECULE TYPE: cDNA ( i x ) FEATURE:
( A ) NAME/KEY: CDS
( B ) LOCATION: 181..3006

( x i ) SEQUENCE DESCRIPTION: SEQ ID NO:42:

```
GCGGGAACTG CCAGGGCAGC AGGGCTGGAT TGGGGTGTTG AGTCCAGGCT GAGTCGGGGA        60

CAGGCCACTG TTCTTGGTCC CCGTGCCTGC TGGGCCAGGC GCCCTGCCTG GAGCCCCGGG       120

CAGGGTGGAC AGGGTGAGGT GCCACTTTAG TCTGGTTGGG GAGGCAGACG ATGAGGAGCG       180

ATG GGG CAG GCA TGC GGC CAC TCC ATC CTC TGC AGG AGC CAG CAG TAC        228
Met Gly Gln Ala Cys Gly His Ser Ile Leu Cys Arg Ser Gln Gln Tyr
  1               5                  10                  15

CCG GCT GCG CGA CCG GCT GAG CCG CGG GGC CAG CAG GTC TTC CTC AAG        276
Pro Ala Ala Arg Pro Ala Glu Pro Arg Gly Gln Gln Val Phe Leu Lys
              20                  25                  30

CCG GAC GAG CCG CCG CCG CCG CAG CCA TGC GCC GAC AGC CTG CAG            324
Pro Asp Glu Pro Pro Pro Pro Gln Pro Cys Ala Asp Ser Leu Gln
          35                  40                  45

GAT GCT TTG CTG AGC CTG GGC TCC GTC ATT GAC GTT GCA GGC TTG CAA        372
Asp Ala Leu Leu Ser Leu Gly Ser Val Ile Asp Val Ala Gly Leu Gln
 50                  55                  60

CAG GCT GTC AAG GAG GCC CTG TCG GCT GTG CTT CCC AAA GTG GAG ACG        420
Gln Ala Val Lys Glu Ala Leu Ser Ala Val Leu Pro Lys Val Glu Thr
 65                  70                  75                  80

GTC TAC ACC TAC CTG CTG GAT GGG GAA TCC CGG CTG GTG TGT GAG GAG        468
Val Tyr Thr Tyr Leu Leu Asp Gly Glu Ser Arg Leu Val Cys Glu Glu
              85                  90                  95

CCC CCC CAC GAG CTG CCC CAG GAG GGG AAA GTG CGA GAG GCT GTG ATC        516
Pro Pro His Glu Leu Pro Gln Glu Gly Lys Val Arg Glu Ala Val Ile
             100                 105                 110

TCC CGG AAG CGG CTG GGC TGC AAT GGA CTG GGC CCC TCA GAC CTG CCT        564
Ser Arg Lys Arg Leu Gly Cys Asn Gly Leu Gly Pro Ser Asp Leu Pro
             115                 120                 125

GGG AAG CCC TTG GCA AGG CTG GTG GCT CCA CTG GCT CCT GAC ACC CAA        612
Gly Lys Pro Leu Ala Arg Leu Val Ala Pro Leu Ala Pro Asp Thr Gln
 130                 135                 140

GTG CTG GTC ATA CCG CTG GTG GAC AAG GAG GCC GGG GCT GTG GCA GCT        660
Val Leu Val Ile Pro Leu Val Asp Lys Glu Ala Gly Ala Val Ala Ala
 145                 150                 155                 160

GTC ATC TTG GTG CAC TGT GGT CAG CTG AGT GAC AAT GAG GAG TGG AGC        708
Val Ile Leu Val His Cys Gly Gln Leu Ser Asp Asn Glu Glu Trp Ser
             165                 170                 175

CTG CAA GCT GTG GAG AAG CAT ACC CTG GTG GCC CTG AAA AGG GTG CAG        756
Leu Gln Ala Val Glu Lys His Thr Leu Val Ala Leu Lys Arg Val Gln
             180                 185                 190

GCC TTG CAG CAG CGC GAG TCC AGC GTG GCC CCG GAA GCG ACC CAG AAT        804
Ala Leu Gln Gln Arg Glu Ser Ser Val Ala Pro Glu Ala Thr Gln Asn
             195                 200                 205

CCT CCG GAG GAG GCA GCG GGA GAC CAG AAG GGT GGG GTC GCA TAC ACA        852
Pro Pro Glu Glu Ala Ala Gly Asp Gln Lys Gly Gly Val Ala Tyr Thr
 210                 215                 220

GAC CAA GAC CGA AAG ATC CTG CAG CTT TGC GGG GAG CTC TAC GAC CTG        900
Asp Gln Asp Arg Lys Ile Leu Gln Leu Cys Gly Glu Leu Tyr Asp Leu
 225                 230                 235                 240

GAT GCA TCT TCC CTG CAG CTC AAA GTC CTC CAA TAT CTG CAA CAG GAG        948
Asp Ala Ser Ser Leu Gln Leu Lys Val Leu Gln Tyr Leu Gln Gln Glu
```

-continued

| | | | | | | | | | | | | | | | |
|---|---|---|---|---|---|---|---|---|---|---|---|---|---|---|---|
| | | | 245 | | | | | 250 | | | | | 255 | | |
| ACC | CAG | GCA | TCC | CGC | TGC | TGC | CTG | CTG | CTG | GTA | TCC | GAG | GAC | AAT | CTT | 996 |
| Thr | Gln | Ala | Ser | Arg | Cys | Cys | Leu | Leu | Leu | Val | Ser | Glu | Asp | Asn | Leu |
| | | 260 | | | | | 265 | | | | | 270 | | | |
| CAG | CTC | TCC | TGC | AAG | GTC | ATT | GGA | GAT | AAA | GTA | CTG | GAG | GAA | GAG | ATC | 1044 |
| Gln | Leu | Ser | Cys | Lys | Val | Ile | Gly | Asp | Lys | Val | Leu | Glu | Glu | Glu | Ile |
| | | 275 | | | | | 280 | | | | | 285 | | | |
| AGC | TTT | CCG | TTG | ACC | ACA | GGA | CGC | CTG | GGC | CAA | GTG | GTG | GAA | GAC | AAG | 1092 |
| Ser | Phe | Pro | Leu | Thr | Thr | Gly | Arg | Leu | Gly | Gln | Val | Val | Glu | Asp | Lys |
| | 290 | | | | | 295 | | | | | 300 | | | | |
| AAG | TCT | ATC | CAG | CTG | AAA | GAT | CTC | ACC | TCC | GAG | GAT | ATG | CAA | CAG | CTG | 1140 |
| Lys | Ser | Ile | Gln | Leu | Lys | Asp | Leu | Thr | Ser | Glu | Asp | Met | Gln | Gln | Leu |
| 305 | | | | | 310 | | | | | 315 | | | | | 320 |
| CAA | AGC | ATG | TTG | GGC | TGT | GAG | GTG | CAG | GCC | ATG | CTC | TGT | GTC | CCT | GTC | 1188 |
| Gln | Ser | Met | Leu | Gly | Cys | Glu | Val | Gln | Ala | Met | Leu | Cys | Val | Pro | Val |
| | | | | 325 | | | | | 330 | | | | | 335 | |
| ATC | AGC | CGG | GCC | ACT | GAC | CAG | GTC | GTG | GCC | CTG | GCC | TGT | GCC | TTC | AAC | 1236 |
| Ile | Ser | Arg | Ala | Thr | Asp | Gln | Val | Val | Ala | Leu | Ala | Cys | Ala | Phe | Asn |
| | | | 340 | | | | | 345 | | | | | 350 | | |
| AAG | CTC | GGA | GGA | GAC | TTG | TTC | ACA | GAC | CAG | GAC | GAG | CAC | GTG | ATC | CAG | 1284 |
| Lys | Leu | Gly | Gly | Asp | Leu | Phe | Thr | Asp | Gln | Asp | Glu | His | Val | Ile | Gln |
| | | 355 | | | | | 360 | | | | | 365 | | | |
| CAC | TGC | TTC | CAC | TAC | ACC | AGC | ACA | GTG | CTC | ACC | AGC | ACC | CTG | GCC | TTC | 1332 |
| His | Cys | Phe | His | Tyr | Thr | Ser | Thr | Val | Leu | Thr | Ser | Thr | Leu | Ala | Phe |
| | 370 | | | | | 375 | | | | | 380 | | | | |
| CAG | AAG | GAG | CAG | AAG | CTC | AAG | TGT | GAG | TGC | CAG | GCT | CTT | CTC | CAA | GTG | 1380 |
| Gln | Lys | Glu | Gln | Lys | Leu | Lys | Cys | Glu | Cys | Gln | Ala | Leu | Leu | Gln | Val |
| 385 | | | | | 390 | | | | | 395 | | | | | 400 |
| GCG | AAG | AAC | CTC | TTC | ACT | CAT | CTG | GAT | GAC | GTC | TCC | GTG | CTG | CTC | CAG | 1428 |
| Ala | Lys | Asn | Leu | Phe | Thr | His | Leu | Asp | Asp | Val | Ser | Val | Leu | Leu | Gln |
| | | | | 405 | | | | | 410 | | | | | 415 | |
| GAG | ATC | ATC | ACA | GAG | GCC | AGG | AAC | CTC | AGC | AAT | GCT | GAG | ATC | TGC | TCT | 1476 |
| Glu | Ile | Ile | Thr | Glu | Ala | Arg | Asn | Leu | Ser | Asn | Ala | Glu | Ile | Cys | Ser |
| | | | 420 | | | | | 425 | | | | | 430 | | |
| GTG | TTC | CTG | CTG | GAT | CAG | AAC | GAG | CTG | GTG | GCC | AAG | GTG | TTC | GAT | GGG | 1524 |
| Val | Phe | Leu | Leu | Asp | Gln | Asn | Glu | Leu | Val | Ala | Lys | Val | Phe | Asp | Gly |
| | | 435 | | | | | 440 | | | | | 445 | | | |
| GGT | GTG | GTG | GAA | GAT | GAG | AGC | TAT | GAG | ATC | CGC | ATT | CCC | GCT | GAC | CAG | 1572 |
| Gly | Val | Val | Glu | Asp | Glu | Ser | Tyr | Glu | Ile | Arg | Ile | Pro | Ala | Asp | Gln |
| | 450 | | | | | 455 | | | | | 460 | | | | |
| GGC | ATC | GCG | GGT | CAT | GTG | GCG | ACC | ACC | GGC | CAG | ATC | CTA | AAC | ATC | CCA | 1620 |
| Gly | Ile | Ala | Gly | His | Val | Ala | Thr | Thr | Gly | Gln | Ile | Leu | Asn | Ile | Pro |
| 465 | | | | | 470 | | | | | 475 | | | | | 480 |
| GAT | GCT | TAC | GCA | CAT | CCG | CTT | TTC | TAC | CGA | GGC | GTG | GAC | GAC | AGC | ACC | 1668 |
| Asp | Ala | Tyr | Ala | His | Pro | Leu | Phe | Tyr | Arg | Gly | Val | Asp | Asp | Ser | Thr |
| | | | | 485 | | | | | 490 | | | | | 495 | |
| GGC | TTC | CGG | ACG | CGC | AAC | ATC | CTC | TGC | TTC | CCC | ATC | AAG | AAC | GAG | AAC | 1716 |
| Gly | Phe | Arg | Thr | Arg | Asn | Ile | Leu | Cys | Phe | Pro | Ile | Lys | Asn | Glu | Asn |
| | | | 500 | | | | | 505 | | | | | 510 | | |
| CAG | GAG | GTC | ATC | GGT | GTG | GCC | GAG | CTG | GTG | AAC | AAG | ATC | AAT | GGA | CCA | 1764 |
| Gln | Glu | Val | Ile | Gly | Val | Ala | Glu | Leu | Val | Asn | Lys | Ile | Asn | Gly | Pro |
| | | 515 | | | | | 520 | | | | | 525 | | | |
| TGG | TTC | AGC | AAG | TTT | GAT | GAA | GAC | CTG | GCT | ACA | GCC | TTC | TCC | ATC | TAC | 1812 |
| Trp | Phe | Ser | Lys | Phe | Asp | Glu | Asp | Leu | Ala | Thr | Ala | Phe | Ser | Ile | Tyr |
| | 530 | | | | | 535 | | | | | 540 | | | | |
| TGT | GGC | ATC | AGC | ATT | GCC | CAT | TCC | CTC | CTA | TAC | AAG | AAA | GTG | AAT | GAG | 1860 |
| Cys | Gly | Ile | Ser | Ile | Ala | His | Ser | Leu | Leu | Tyr | Lys | Lys | Val | Asn | Glu |
| 545 | | | | | 550 | | | | | 555 | | | | | 560 |
| GCG | CAG | TAT | CGC | AGC | CAC | CTT | GCC | AAT | GAG | ATG | ATG | ATG | TAC | CAC | ATG | 1908 |
| Ala | Gln | Tyr | Arg | Ser | His | Leu | Ala | Asn | Glu | Met | Met | Met | Tyr | His | Met |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     |     |     | 565 |     |     |     |     | 570 |     |     |     |     | 575 |     |      |
| AAG | GTC | TCT | GAT | GAC | GAG | TAC | ACC | AAA | CTT | CTC | CAT | GAC | GGG | ATC | CAG | 1956 |
| Lys | Val | Ser | Asp | Asp | Glu | Tyr | Thr | Lys | Leu | Leu | His | Asp | Gly | Ile | Gln |      |
|     |     |     | 580 |     |     |     |     | 585 |     |     |     |     | 590 |     |     |      |
| CCT | GTG | GCT | GCC | ATC | GAC | TCC | AAC | TTT | GCC | AGT | TTC | ACA | TAC | ACT | CCT | 2004 |
| Pro | Val | Ala | Ala | Ile | Asp | Ser | Asn | Phe | Ala | Ser | Phe | Thr | Tyr | Thr | Pro |      |
|     |     | 595 |     |     |     | 600 |     |     |     |     | 605 |     |     |     |     |      |
| CGC | TCT | CTG | CCC | GAG | GAT | GAC | ACT | TCC | ATG | GCC | ATC | CTG | AGC | ATG | CTG | 2052 |
| Arg | Ser | Leu | Pro | Glu | Asp | Asp | Thr | Ser | Met | Ala | Ile | Leu | Ser | Met | Leu |      |
|     | 610 |     |     |     |     | 615 |     |     |     |     | 620 |     |     |     |     |      |
| CAG | GAC | ATG | AAT | TTC | ATC | AAT | AAC | TAC | AAA | ATT | GAC | TGC | CCG | ACA | CTG | 2100 |
| Gln | Asp | Met | Asn | Phe | Ile | Asn | Asn | Tyr | Lys | Ile | Asp | Cys | Pro | Thr | Leu |      |
| 625 |     |     |     |     | 630 |     |     |     |     | 635 |     |     |     |     | 640 |      |
| GCC | CGG | TTC | TGT | TTG | ATG | GTG | AAG | AAG | GGC | TAC | CGG | GAT | CCC | CCC | TAC | 2148 |
| Ala | Arg | Phe | Cys | Leu | Met | Val | Lys | Lys | Gly | Tyr | Arg | Asp | Pro | Pro | Tyr |      |
|     |     |     |     | 645 |     |     |     |     | 650 |     |     |     |     | 655 |     |      |
| CAC | AAC | TGG | ATG | CAC | GCC | TTT | TCT | GTC | TCC | CAC | TTC | TGC | TAC | CTG | CTC | 2196 |
| His | Asn | Trp | Met | His | Ala | Phe | Ser | Val | Ser | His | Phe | Cys | Tyr | Leu | Leu |      |
|     |     |     | 660 |     |     |     |     | 665 |     |     |     |     | 670 |     |     |      |
| TAC | AAG | AAC | CTG | GAG | CTC | ACC | AAC | TAC | CTC | GAG | GAC | ATG | GAG | ATC | TTT | 2244 |
| Tyr | Lys | Asn | Leu | Glu | Leu | Thr | Asn | Tyr | Leu | Glu | Asp | Met | Glu | Ile | Phe |      |
|     |     | 675 |     |     |     |     | 680 |     |     |     |     | 685 |     |     |     |      |
| GCC | TTG | TTT | ATT | TCC | TGC | ATG | TGT | CAC | GAC | CTG | GAC | CAC | AGA | GGC | ACA | 2292 |
| Ala | Leu | Phe | Ile | Ser | Cys | Met | Cys | His | Asp | Leu | Asp | His | Arg | Gly | Thr |      |
|     | 690 |     |     |     |     | 695 |     |     |     |     | 700 |     |     |     |     |      |
| AAC | AAC | TCC | TTC | CAG | GTG | GCC | TCG | AAA | TCT | GTG | CTG | GCC | GCG | CTC | TAC | 2340 |
| Asn | Asn | Ser | Phe | Gln | Val | Ala | Ser | Lys | Ser | Val | Leu | Ala | Ala | Leu | Tyr |      |
| 705 |     |     |     |     | 710 |     |     |     |     | 715 |     |     |     |     | 720 |      |
| AGC | TCG | GAA | GGC | TCT | GTC | ATG | GAG | AGG | CAC | CAC | TTC | GCT | CAG | GCC | ATT | 2388 |
| Ser | Ser | Glu | Gly | Ser | Val | Met | Glu | Arg | His | His | Phe | Ala | Gln | Ala | Ile |      |
|     |     |     |     | 725 |     |     |     |     | 730 |     |     |     |     | 735 |     |      |
| GCC | ATC | CTC | AAC | ACC | CAC | GGC | TGC | AAC | ATC | TTT | GAC | CAC | TTC | TCC | CGG | 2436 |
| Ala | Ile | Leu | Asn | Thr | His | Gly | Cys | Asn | Ile | Phe | Asp | His | Phe | Ser | Arg |      |
|     |     |     | 740 |     |     |     |     | 745 |     |     |     |     | 750 |     |     |      |
| AAG | GAT | TAT | CAG | CGC | ATG | TTG | GAC | CTG | ATG | CGG | GAC | ATC | ATC | TTG | GCC | 2484 |
| Lys | Asp | Tyr | Gln | Arg | Met | Leu | Asp | Leu | Met | Arg | Asp | Ile | Ile | Leu | Ala |      |
|     |     | 755 |     |     |     |     | 760 |     |     |     |     | 765 |     |     |     |      |
| ACA | GAT | CTG | GCC | CAC | CAC | CTC | CGC | ATC | TTC | AAG | GAC | CTC | CAA | AAG | ATG | 2532 |
| Thr | Asp | Leu | Ala | His | His | Leu | Arg | Ile | Phe | Lys | Asp | Leu | Gln | Lys | Met |      |
| 770 |     |     |     |     | 775 |     |     |     |     | 780 |     |     |     |     |     |      |
| GCC | GAA | GTG | GGC | TAT | GAT | CGA | ACC | AAC | AAG | CAG | CAC | CAC | AGC | CTC | CTT | 2580 |
| Ala | Glu | Val | Gly | Tyr | Asp | Arg | Thr | Asn | Lys | Gln | His | His | Ser | Leu | Leu |      |
| 785 |     |     |     |     | 790 |     |     |     |     | 795 |     |     |     |     | 800 |      |
| CTC | TGC | CTC | CTT | ATG | ACC | TCC | TGT | GAC | CTC | TCT | GAC | CAG | ACC | AAG | GGC | 2628 |
| Leu | Cys | Leu | Leu | Met | Thr | Ser | Cys | Asp | Leu | Ser | Asp | Gln | Thr | Lys | Gly |      |
|     |     |     |     | 805 |     |     |     |     | 810 |     |     |     |     | 815 |     |      |
| TGG | AAG | ACC | ACG | AGG | AAG | ATC | GCG | GAG | CTG | ATC | TAC | AAA | GAG | TTC | TTC | 2676 |
| Trp | Lys | Thr | Thr | Arg | Lys | Ile | Ala | Glu | Leu | Ile | Tyr | Lys | Glu | Phe | Phe |      |
|     |     |     | 820 |     |     |     |     | 825 |     |     |     |     | 830 |     |     |      |
| TCC | CAG | GGA | GAC | TTG | GAG | AAG | GCC | ATG | GGC | AAC | AGG | CCG | ATG | GAG | ATG | 2724 |
| Ser | Gln | Gly | Asp | Leu | Glu | Lys | Ala | Met | Gly | Asn | Arg | Pro | Met | Glu | Met |      |
|     |     | 835 |     |     |     |     | 840 |     |     |     |     | 845 |     |     |     |      |
| ATG | GAC | CGT | GAG | AAG | GCC | TAC | ATC | CCC | GAG | CTG | CAG | ATC | AGC | TTC | ATG | 2772 |
| Met | Asp | Arg | Glu | Lys | Ala | Tyr | Ile | Pro | Glu | Leu | Gln | Ile | Ser | Phe | Met |      |
| 850 |     |     |     |     | 855 |     |     |     |     | 860 |     |     |     |     |     |      |
| GAG | CAC | ATC | GCA | ATG | CCC | ATC | TAC | AAG | CTG | CTG | CAA | GAC | CTG | TTC | CCC | 2820 |
| Glu | His | Ile | Ala | Met | Pro | Ile | Tyr | Lys | Leu | Leu | Gln | Asp | Leu | Phe | Pro |      |
| 865 |     |     |     |     | 870 |     |     |     |     | 875 |     |     |     |     | 880 |      |
| AAG | GCG | GCC | GAG | TTG | TAC | GAA | CGC | GTG | GCC | TCT | AAT | CGT | GAG | CAC | TGG | 2868 |
| Lys | Ala | Ala | Glu | Leu | Tyr | Glu | Arg | Val | Ala | Ser | Asn | Arg | Glu | His | Trp |      |

-continued

```
                              885                              890                              895
ACC  AAG  GTG  TCA  CAC  AAG  TTC  ACC  ATC  CGA  GGC  CTC  CCG  AGC  AAC  AAC                    2916
Thr  Lys  Val  Ser  His  Lys  Phe  Thr  Ile  Arg  Gly  Leu  Pro  Ser  Asn  Asn
               900                              905                              910

TCG  TTG  GAC  TTC  CTG  GAC  GAG  GAG  TAT  GAG  GTG  CCT  GAC  CTG  GAT  GGC                    2964
Ser  Leu  Asp  Phe  Leu  Asp  Glu  Glu  Tyr  Glu  Val  Pro  Asp  Leu  Asp  Gly
               915                              920                              925

GCT  AGG  GCT  CCC  ATC  AAT  GGC  TGT  TGC  AGC  CTT  GAT  GCT  GAG                              3006
Ala  Arg  Ala  Pro  Ile  Asn  Gly  Cys  Cys  Ser  Leu  Asp  Ala  Glu
               930                              935                         940
```

| | | | | | |
|---|---|---|---|---|---|
| TGAGTCCCTC | CTGGGACCCC | TCCCTGTCCA | GGCCTCCTCC | CACAAGCCTC | CACGGGCCTG | 3066 |
| GCCGCACGCC | CTGGGACCAG | AGCCAAGGGT | CCTGGATTCT | AGGCCAGGAC | TTCCCATGTG | 3126 |
| ACCCGGGCGA | GGTCTGACCT | TCCCGGGCCT | CAGCTTTCTT | GTCTGTATAA | TGGAAGACTT | 3186 |
| CAGCCTCACT | GAGACTTTGT | CACTTGTCCT | CTGAGAGCAC | AGGGGTAACC | AATGAGCAGT | 3246 |
| GGACCCTGCT | CTGCACCTCT | GACCGCATCT | TGGCAAGTCC | CCACCCTCCA | GGCCACTCCT | 3306 |
| TCTCTGAGGC | AGCCGGATGG | TTTCTTCTGG | GCCCCATTCC | TGCCCTACCA | GACCTGTGCC | 3366 |
| CTTTCCTGTG | GGGCACCCT | CACTGGCTCC | CAGGATCCTC | AGGCAAGAAC | ATGAGACATC | 3426 |
| TGAGTGGGCA | AAGGGTGGGT | CTTAGAGACA | GTTATCAGCC | TGGCTGGAGG | ACTAGAAGTA | 3486 |
| GCCATGGGAC | CACCTGTGGC | CCAGAGGACT | GCCTTTGTAC | TTATGGTGGG | GACTGGGACC | 3546 |
| TGGGGATATA | AGGGTCCCAG | GAGGACACTG | CCAGGGGCC | AGTGCAGTGC | TCTGGGAGA | 3606 |
| GGGGGCTCAG | GAAGAGAGGA | GGATAAGAAC | AGTGAGAAGG | AAGGATCCCT | GGGTTGGGAG | 3666 |
| GCAGGCCCAG | CATGGGTCAG | CCATGCTTCC | TCCTGGCTGT | GTGACCCTGG | GCAAGTCCCT | 3726 |
| TCCCCTCTCT | GCGAAACAGT | AGGGTGAGAC | AATCCATTCT | CTAAGACCCC | TTTTAGATCC | 3786 |
| AAG | | | | | | 3789 |

( 2 ) INFORMATION FOR SEQ ID NO:43:

( i ) SEQUENCE CHARACTERISTICS:
        ( A ) LENGTH: 942 amino acids
        ( B ) TYPE: amino acid
        ( D ) TOPOLOGY: linear ( i i ) MOLECULE TYPE: protein ( x i ) SEQUENCE DESCRIPTION: SEQ ID NO:43:

```
Met  Gly  Gln  Ala  Cys  Gly  His  Ser  Ile  Leu  Cys  Arg  Ser  Gln  Gln  Tyr
 1                  5                      10                         15

Pro  Ala  Ala  Arg  Pro  Ala  Glu  Pro  Arg  Gly  Gln  Gln  Val  Phe  Leu  Lys
               20                      25                         30

Pro  Asp  Glu  Pro  Pro  Pro  Pro  Gln  Pro  Cys  Ala  Asp  Ser  Leu  Gln
          35                         40                     45

Asp  Ala  Leu  Leu  Ser  Leu  Gly  Ser  Val  Ile  Asp  Val  Ala  Gly  Leu  Gln
          50                      55                     60

Gln  Ala  Val  Lys  Glu  Ala  Leu  Ser  Ala  Val  Leu  Pro  Lys  Val  Glu  Thr
 65                      70                     75                         80

Val  Tyr  Thr  Tyr  Leu  Leu  Asp  Gly  Glu  Ser  Arg  Leu  Val  Cys  Glu  Glu
                    85                     90                         95

Pro  Pro  His  Glu  Leu  Pro  Gln  Glu  Gly  Lys  Val  Arg  Glu  Ala  Val  Ile
               100                     105                        110

Ser  Arg  Lys  Arg  Leu  Gly  Cys  Asn  Gly  Leu  Gly  Pro  Ser  Asp  Leu  Pro
          115                         120                    125

Gly  Lys  Pro  Leu  Ala  Arg  Leu  Val  Ala  Pro  Leu  Ala  Pro  Asp  Thr  Gln
 130                          135                        140
```

-continued

| | | | | | | | | | | | | | | | |
|---|---|---|---|---|---|---|---|---|---|---|---|---|---|---|---|
| Val | Leu | Val | Ile | Pro | Leu | Val | Asp | Lys | Glu | Ala | Gly | Ala | Val | Ala | Ala |
| 145 | | | | 150 | | | | 155 | | | | | | | 160 |
| Val | Ile | Leu | Val | His | Cys | Gly | Gln | Leu | Ser | Asp | Asn | Glu | Glu | Trp | Ser |
| | | | | 165 | | | | 170 | | | | | 175 | | |
| Leu | Gln | Ala | Val | Glu | Lys | His | Thr | Leu | Val | Ala | Leu | Lys | Arg | Val | Gln |
| | | | 180 | | | | | 185 | | | | | 190 | | |
| Ala | Leu | Gln | Gln | Arg | Glu | Ser | Ser | Val | Ala | Pro | Glu | Ala | Thr | Gln | Asn |
| | | 195 | | | | | 200 | | | | | 205 | | | |
| Pro | Pro | Glu | Glu | Ala | Ala | Gly | Asp | Gln | Lys | Gly | Gly | Val | Ala | Tyr | Thr |
| 210 | | | | | | 215 | | | | | 220 | | | | |
| Asp | Gln | Asp | Arg | Lys | Ile | Leu | Gln | Leu | Cys | Gly | Glu | Leu | Tyr | Asp | Leu |
| 225 | | | | | 230 | | | | | 235 | | | | | 240 |
| Asp | Ala | Ser | Ser | Leu | Gln | Leu | Lys | Val | Leu | Gln | Tyr | Leu | Gln | Gln | Glu |
| | | | | 245 | | | | | 250 | | | | | 255 | |
| Thr | Gln | Ala | Ser | Arg | Cys | Cys | Leu | Leu | Leu | Val | Ser | Glu | Asp | Asn | Leu |
| | | | 260 | | | | | 265 | | | | | 270 | | |
| Gln | Leu | Ser | Cys | Lys | Val | Ile | Gly | Asp | Lys | Val | Leu | Glu | Glu | Glu | Ile |
| | | 275 | | | | | 280 | | | | | 285 | | | |
| Ser | Phe | Pro | Leu | Thr | Thr | Gly | Arg | Leu | Gly | Gln | Val | Val | Glu | Asp | Lys |
| | 290 | | | | | 295 | | | | | 300 | | | | |
| Lys | Ser | Ile | Gln | Leu | Lys | Asp | Leu | Thr | Ser | Glu | Asp | Met | Gln | Gln | Leu |
| 305 | | | | | 310 | | | | | 315 | | | | | 320 |
| Gln | Ser | Met | Leu | Gly | Cys | Glu | Val | Gln | Ala | Met | Leu | Cys | Val | Pro | Val |
| | | | | 325 | | | | | 330 | | | | | 335 | |
| Ile | Ser | Arg | Ala | Thr | Asp | Gln | Val | Val | Ala | Leu | Ala | Cys | Ala | Phe | Asn |
| | | | 340 | | | | | 345 | | | | | 350 | | |
| Lys | Leu | Gly | Gly | Asp | Leu | Phe | Thr | Asp | Gln | Asp | Glu | His | Val | Ile | Gln |
| | | | 355 | | | | | 360 | | | | | 365 | | |
| His | Cys | Phe | His | Tyr | Thr | Ser | Thr | Val | Leu | Thr | Ser | Thr | Leu | Ala | Phe |
| | 370 | | | | | 375 | | | | | 380 | | | | |
| Gln | Lys | Glu | Gln | Lys | Leu | Lys | Cys | Glu | Cys | Gln | Ala | Leu | Leu | Gln | Val |
| 385 | | | | | 390 | | | | | 395 | | | | | 400 |
| Ala | Lys | Asn | Leu | Phe | Thr | His | Leu | Asp | Asp | Val | Ser | Val | Leu | Leu | Gln |
| | | | | 405 | | | | | 410 | | | | | 415 | |
| Glu | Ile | Ile | Thr | Glu | Ala | Arg | Asn | Leu | Ser | Asn | Ala | Glu | Ile | Cys | Ser |
| | | | 420 | | | | | 425 | | | | | 430 | | |
| Val | Phe | Leu | Leu | Asp | Gln | Asn | Glu | Leu | Val | Ala | Lys | Val | Phe | Asp | Gly |
| | | | 435 | | | | | 440 | | | | | 445 | | |
| Gly | Val | Val | Glu | Asp | Glu | Ser | Tyr | Glu | Ile | Arg | Ile | Pro | Ala | Asp | Gln |
| | 450 | | | | | 455 | | | | | 460 | | | | |
| Gly | Ile | Ala | Gly | His | Val | Ala | Thr | Thr | Gly | Gln | Ile | Leu | Asn | Ile | Pro |
| 465 | | | | | 470 | | | | | 475 | | | | | 480 |
| Asp | Ala | Tyr | Ala | His | Pro | Leu | Phe | Tyr | Arg | Gly | Val | Asp | Asp | Ser | Thr |
| | | | | 485 | | | | | 490 | | | | | 495 | |
| Gly | Phe | Arg | Thr | Arg | Asn | Ile | Leu | Cys | Phe | Pro | Ile | Lys | Asn | Glu | Asn |
| | | | 500 | | | | | 505 | | | | | 510 | | |
| Gln | Glu | Val | Ile | Gly | Val | Ala | Glu | Leu | Val | Asn | Lys | Ile | Asn | Gly | Pro |
| | | | 515 | | | | | 520 | | | | | 525 | | |
| Trp | Phe | Ser | Lys | Phe | Asp | Glu | Asp | Leu | Ala | Thr | Ala | Phe | Ser | Ile | Tyr |
| | | 530 | | | | | 535 | | | | | 540 | | | |
| Cys | Gly | Ile | Ser | Ile | Ala | His | Ser | Leu | Leu | Tyr | Lys | Lys | Val | Asn | Glu |
| 545 | | | | | 550 | | | | | 555 | | | | | 560 |
| Ala | Gln | Tyr | Arg | Ser | His | Leu | Ala | Asn | Glu | Met | Met | Met | Tyr | His | Met |

|     |     |     |     |     |     |     |     |     |     |     |     |     |     |     |
|-----|-----|-----|-----|-----|-----|-----|-----|-----|-----|-----|-----|-----|-----|-----|
|     |     |     |     | 565 |     |     |     | 570 |     |     |     | 575 |     |     |
| Lys | Val | Ser | Asp | Asp | Glu | Tyr | Thr | Lys | Leu | Leu | His | Asp | Gly | Ile | Gln |
|     |     |     | 580 |     |     |     | 585 |     |     |     |     | 590 |     |     |
| Pro | Val | Ala | Ala | Ile | Asp | Ser | Asn | Phe | Ala | Ser | Phe | Thr | Tyr | Thr | Pro |
|     |     | 595 |     |     |     | 600 |     |     |     |     | 605 |     |     |     |
| Arg | Ser | Leu | Pro | Glu | Asp | Asp | Thr | Ser | Met | Ala | Ile | Leu | Ser | Met | Leu |
|     | 610 |     |     |     |     | 615 |     |     |     | 620 |     |     |     |     |
| Gln | Asp | Met | Asn | Phe | Ile | Asn | Asn | Tyr | Lys | Ile | Asp | Cys | Pro | Thr | Leu |
| 625 |     |     |     |     | 630 |     |     |     | 635 |     |     |     |     | 640 |
| Ala | Arg | Phe | Cys | Leu | Met | Val | Lys | Lys | Gly | Tyr | Arg | Asp | Pro | Pro | Tyr |
|     |     |     |     | 645 |     |     |     | 650 |     |     |     | 655 |     |
| His | Asn | Trp | Met | His | Ala | Phe | Ser | Val | Ser | His | Phe | Cys | Tyr | Leu | Leu |
|     |     |     | 660 |     |     |     | 665 |     |     |     |     | 670 |     |
| Tyr | Lys | Asn | Leu | Glu | Leu | Thr | Asn | Tyr | Leu | Glu | Asp | Met | Glu | Ile | Phe |
|     |     | 675 |     |     |     | 680 |     |     |     |     | 685 |     |     |
| Ala | Leu | Phe | Ile | Ser | Cys | Met | Cys | His | Asp | Leu | Asp | His | Arg | Gly | Thr |
|     | 690 |     |     |     |     | 695 |     |     |     | 700 |     |     |     |     |
| Asn | Asn | Ser | Phe | Gln | Val | Ala | Ser | Lys | Ser | Val | Leu | Ala | Ala | Leu | Tyr |
| 705 |     |     |     | 710 |     |     |     | 715 |     |     |     |     | 720 |
| Ser | Ser | Glu | Gly | Ser | Val | Met | Glu | Arg | His | His | Phe | Ala | Gln | Ala | Ile |
|     |     |     |     | 725 |     |     |     | 730 |     |     |     |     | 735 |
| Ala | Ile | Leu | Asn | Thr | His | Gly | Cys | Asn | Ile | Phe | Asp | His | Phe | Ser | Arg |
|     |     |     | 740 |     |     |     | 745 |     |     |     | 750 |     |     |
| Lys | Asp | Tyr | Gln | Arg | Met | Leu | Asp | Leu | Met | Arg | Asp | Ile | Ile | Leu | Ala |
|     | 755 |     |     |     |     | 760 |     |     |     | 765 |     |     |     |
| Thr | Asp | Leu | Ala | His | His | Leu | Arg | Ile | Phe | Lys | Asp | Leu | Gln | Lys | Met |
| 770 |     |     |     |     | 775 |     |     |     | 780 |     |     |     |     |
| Ala | Glu | Val | Gly | Tyr | Asp | Arg | Thr | Asn | Lys | Gln | His | His | Ser | Leu | Leu |
| 785 |     |     |     |     | 790 |     |     |     | 795 |     |     |     |     | 800 |
| Leu | Cys | Leu | Leu | Met | Thr | Ser | Cys | Asp | Leu | Ser | Asp | Gln | Thr | Lys | Gly |
|     |     |     |     | 805 |     |     |     | 810 |     |     |     | 815 |     |
| Trp | Lys | Thr | Thr | Arg | Lys | Ile | Ala | Glu | Leu | Ile | Tyr | Lys | Glu | Phe | Phe |
|     |     |     | 820 |     |     |     | 825 |     |     |     | 830 |     |     |
| Ser | Gln | Gly | Asp | Leu | Glu | Lys | Ala | Met | Gly | Asn | Arg | Pro | Met | Glu | Met |
|     |     | 835 |     |     |     | 840 |     |     |     | 845 |     |     |     |
| Met | Asp | Arg | Glu | Lys | Ala | Tyr | Ile | Pro | Glu | Leu | Gln | Ile | Ser | Phe | Met |
|     | 850 |     |     |     | 855 |     |     |     | 860 |     |     |     |     |
| Glu | His | Ile | Ala | Met | Pro | Ile | Tyr | Lys | Leu | Leu | Gln | Asp | Leu | Phe | Pro |
| 865 |     |     |     | 870 |     |     |     | 875 |     |     |     |     | 880 |
| Lys | Ala | Ala | Glu | Leu | Tyr | Glu | Arg | Val | Ala | Ser | Asn | Arg | Glu | His | Trp |
|     |     |     | 885 |     |     |     | 890 |     |     |     | 895 |     |
| Thr | Lys | Val | Ser | His | Lys | Phe | Thr | Ile | Arg | Gly | Leu | Pro | Ser | Asn | Asn |
|     |     | 900 |     |     |     | 905 |     |     |     | 910 |     |     |
| Ser | Leu | Asp | Phe | Leu | Asp | Glu | Glu | Tyr | Glu | Val | Pro | Asp | Leu | Asp | Gly |
|     |     | 915 |     |     |     | 920 |     |     |     | 925 |     |     |
| Ala | Arg | Ala | Pro | Ile | Asn | Gly | Cys | Cys | Ser | Leu | Asp | Ala | Glu |
|     | 930 |     |     |     | 935 |     |     |     | 940 |     |     |

( 2 ) INFORMATION FOR SEQ ID NO:44:

( i ) SEQUENCE CHARACTERISTICS:
        ( A ) LENGTH: 3044 base pairs
        ( B ) TYPE: nucleic acid
        ( C ) STRANDEDNESS: single
        ( D ) TOPOLOGY: linear 5,800,987

-continued ( i i ) MOLECULE TYPE: cDNA ( i x ) FEATURE:
  ( A ) NAME/KEY: CDS
  ( B ) LOCATION: 12..2834

( x i ) SEQUENCE DESCRIPTION: SEQ ID NO:44:

```
GAATTCTGAT A ATG GGG CAG GCA TGC GGC CAC TCC ATC CTC TGC AGG AGC        50
            Met Gly Gln Ala Cys Gly His Ser Ile Leu Cys Arg Ser
            1             5                   10

CAG CAG TAC CCG GCA GCG CGA CCG GCT GAG CCG CGG GGC CAG CAG GTC         98
Gln Gln Tyr Pro Ala Ala Arg Pro Ala Glu Pro Arg Gly Gln Gln Val
        15              20                  25

TTC CTC AAG CCG GAC GAG CCG CCG CCG CCG CAG CCA TGC GCC GAC            146
Phe Leu Lys Pro Asp Glu Pro Pro Pro Pro Gln Pro Cys Ala Asp
30              35                  40                  45

AGC CTG CAG GAC GCC TTG CTG AGT CTG GGC TCT GTC ATC GAC ATT TCA        194
Ser Leu Gln Asp Ala Leu Leu Ser Leu Gly Ser Val Ile Asp Ile Ser
                50                  55                  60

GGC CTG CAA CGT GCT GTC AAG GAG GCC CTG TCA GCT GTG CTC CCC CGA        242
Gly Leu Gln Arg Ala Val Lys Glu Ala Leu Ser Ala Val Leu Pro Arg
            65                  70                  75

GTG GAA ACT GTC TAC ACC TAC CTA CTG GAT GGT GAG TCC CAG CTG GTG        290
Val Glu Thr Val Tyr Thr Tyr Leu Leu Asp Gly Glu Ser Gln Leu Val
        80                  85                  90

TGT GAG GAC CCC CCA CAT GAG CTG CCC CAG GAG GGG AAA GTC CGG GAG        338
Cys Glu Asp Pro Pro His Glu Leu Pro Gln Glu Gly Lys Val Arg Glu
    95                  100                 105

GCT ATC ATC TCC CAG AAG CGG CTG GGC TGC AAT GGG CTG GGC TTC TCA        386
Ala Ile Ile Ser Gln Lys Arg Leu Gly Cys Asn Gly Leu Gly Phe Ser
110             115                 120                 125

GAC CTG CCA GGG AAG CCC TTG GCC AGG CTG GTG GCT CCA CTG GCT CCT        434
Asp Leu Pro Gly Lys Pro Leu Ala Arg Leu Val Ala Pro Leu Ala Pro
                130                 135                 140

GAT ACC CAA GTG CTG GTC ATG CCG CTA GCG GAC AAG GAG GCT GGG GCC        482
Asp Thr Gln Val Leu Val Met Pro Leu Ala Asp Lys Glu Ala Gly Ala
            145                 150                 155

GTG GCA GCT GTC ATC TTG GTG CAC TGT GGC CAG CTG AGT GAT AAT GAG        530
Val Ala Ala Val Ile Leu Val His Cys Gly Gln Leu Ser Asp Asn Glu
        160                 165                 170

GAA TGG AGC CTG CAG GCG GTG GAG AAG CAT ACC CTG GTC GCC CTG CGG        578
Glu Trp Ser Leu Gln Ala Val Glu Lys His Thr Leu Val Ala Leu Arg
    175                 180                 185

AGG GTG CAG GTC CTG CAG CAG CGC GGG CCC AGG GAG GCT CCC CGA GCC        626
Arg Val Gln Val Leu Gln Gln Arg Gly Pro Arg Glu Ala Pro Arg Ala
190                 195                 200                 205

GTC CAG AAC CCC CCG GAG GGG ACG GCG GAA GAC CAG AAG GGC GGG GCG        674
Val Gln Asn Pro Pro Glu Gly Thr Ala Glu Asp Gln Lys Gly Gly Ala
                210                 215                 220

GCG TAC ACC GAC CGC GAC CGC AAG ATC CTC CAA CTG TGC GGG GAA CTC        722
Ala Tyr Thr Asp Arg Asp Arg Lys Ile Leu Gln Leu Cys Gly Glu Leu
            225                 230                 235

TAC GAC CTG GAT GCC TCT TCC CTG CAG CTC AAA GTG CTC CAA TAC CTG        770
Tyr Asp Leu Asp Ala Ser Ser Leu Gln Leu Lys Val Leu Gln Tyr Leu
        240                 245                 250

CAG CAG GAG ACC CGG GCA TCC CGC TGC TGC CTC CTG CTG GTG TCG GAG        818
Gln Gln Glu Thr Arg Ala Ser Arg Cys Cys Leu Leu Leu Val Ser Glu
    255                 260                 265

GAC AAT CTC CAG CTT TCT TGC AAG GTC ATC GGA GAC AAA GTG CTC GGG        866
Asp Asn Leu Gln Leu Ser Cys Lys Val Ile Gly Asp Lys Val Leu Gly
270                 275                 280                 285
```

-continued

| | | | | | | | | | | | | | | | | |
|---|---|---|---|---|---|---|---|---|---|---|---|---|---|---|---|---|
| GAA | GAG | GTC | AGC | TTT | CCC | TTG | ACA | GGA | TGC | CTG | GGC | CAG | GTG | GTG | GAA | 914 |
| Glu | Glu | Val | Ser | Phe 290 | Pro | Leu | Thr | Gly | Cys 295 | Leu | Gly | Gln | Val | Val 300 | Glu | |
| GAC | AAG | AAG | TCC | ATC | CAG | CTG | AAG | GAC | CTC | ACC | TCC | GAG | GAT | GTA | CAA | 962 |
| Asp | Lys | Lys | Ser 305 | Ile | Gln | Leu | Lys | Asp 310 | Leu | Thr | Ser | Glu | Asp 315 | Val | Gln | |
| CAG | CTG | CAG | AGC | ATG | TTG | GGC | TGT | GAG | CTG | CAG | GCC | ATG | CTC | TGT | GTC | 1010 |
| Gln | Leu | Gln | Ser 320 | Met | Leu | Gly | Cys | Glu 325 | Leu | Gln | Ala | Met 330 | Leu | Cys | Val | |
| CCT | GTC | ATC | AGC | CGG | GCC | ACT | GAC | CAG | GTG | GTG | GCC | TTG | GCC | TGC | GCC | 1058 |
| Pro | Val | Ile 335 | Ser | Arg | Ala | Thr | Asp 340 | Gln | Val | Val | Ala 345 | Leu | Ala | Cys | Ala | |
| TTC | AAC | AAG | CTA | GAA | GGA | GAC | TTG | TTC | ACC | GAC | GAG | GAC | GAG | CAT | GTG | 1106 |
| Phe | Asn | Lys | Leu | Glu 355 | Gly | Asp | Leu | Phe | Thr 360 | Asp | Glu | Asp | Glu | His 365 | Val | |
| Phe 350 | | | | | | | | | | | | | | | | |
| ATC | CAG | CAC | TGC | TTC | CAC | TAC | ACC | AGC | ACC | GTG | CTC | ACC | AGC | ACC | CTG | 1154 |
| Ile | Gln | His | Cys 370 | Phe | His | Tyr | Thr | Ser 375 | Thr | Val | Leu | Thr | Ser 380 | Thr | Leu | |
| GCC | TTC | CAG | AAG | GAA | CAG | AAA | CTC | AAG | TGT | GAG | TGC | CAG | GCT | CTT | CTC | 1202 |
| Ala | Phe | Gln | Lys 385 | Glu | Gln | Lys | Leu | Lys 390 | Cys | Glu | Cys | Gln | Ala 395 | Leu | Leu | |
| CAA | GTG | GCA | AAG | AAC | CTC | TTC | ACC | CAC | CTG | GAT | GAC | GTC | TCT | GTC | CTG | 1250 |
| Gln | Val | Ala 400 | Lys | Asn | Leu | Phe | Thr 405 | His | Leu | Asp | Asp | Val 410 | Ser | Val | Leu | |
| CTC | CAG | GAG | ATC | ATC | ACG | GAG | GCC | AGA | AAC | CTC | AGC | AAC | GCA | GAG | ATC | 1298 |
| Leu | Gln 415 | Glu | Ile | Ile | Thr | Glu 420 | Ala | Arg | Asn | Leu | Ser 425 | Asn | Ala | Glu | Ile | |
| TGC | TCT | GTG | TTC | CTG | CTG | GAT | CAG | AAT | GAG | CTG | GTG | GCC | AAG | GTG | TTC | 1346 |
| Cys 430 | Ser | Val | Phe | Leu | Leu 435 | Asp | Gln | Asn | Glu | Leu 440 | Val | Ala | Lys | Val | Phe 445 | |
| GAC | GGG | GGC | GTG | GTG | GAT | GAT | GAG | AGC | TAT | GAG | ATC | CGC | ATC | CCG | GCC | 1394 |
| Asp | Gly | Gly | Val | Val 450 | Asp | Asp | Glu | Ser | Tyr 455 | Glu | Ile | Arg | Ile | Pro 460 | Ala | |
| GAT | CAG | GGC | ATC | GCG | GGA | CAC | GTG | GCG | ACC | ACG | GGC | CAG | ATC | CTG | AAC | 1442 |
| Asp | Gln | Gly | Ile 465 | Ala | Gly | His | Val | Ala 470 | Thr | Thr | Gly | Gln | Ile 475 | Leu | Asn | |
| ATC | CCT | GAC | GCA | TAT | GCC | CAT | CCG | CTT | TTC | TAC | CGC | GGC | GTG | GAC | GAC | 1490 |
| Ile | Pro | Asp 480 | Ala | Tyr | Ala | His | Pro 485 | Leu | Phe | Tyr | Arg | Gly 490 | Val | Asp | Asp | |
| AGC | ACC | GGC | TTC | CGC | ACG | CGC | AAC | ATC | CTC | TGC | TTC | CCC | ATC | AAG | AAC | 1538 |
| Ser | Thr | Gly 495 | Phe | Arg | Thr | Arg 500 | Asn | Ile | Leu | Cys | Phe 505 | Pro | Ile | Lys | Asn | |
| GAG | AAC | CAG | GAG | GTC | ATC | GGT | GTG | GCC | GAG | CTG | GTG | AAC | AAG | ATC | AAT | 1586 |
| Glu 510 | Asn | Gln | Glu | Val | Ile 515 | Gly | Val | Ala | Glu | Leu 520 | Val | Asn | Lys | Ile | Asn 525 | |
| GGG | CCA | TGG | TTC | AGC | AAG | TTC | GAC | GAG | GAC | CTG | GCG | ACG | GCC | TTC | TCC | 1634 |
| Gly | Pro | Trp | Phe | Ser 530 | Lys | Phe | Asp | Glu | Asp 535 | Leu | Ala | Thr | Ala | Phe 540 | Ser | |
| ATC | TAC | TGC | GGC | ATC | AGC | ATC | GCC | CAT | TCT | CTC | CTA | TAC | AAA | AAA | GTG | 1682 |
| Ile | Tyr | Cys | Gly 545 | Ile | Ser | Ile | Ala | His 550 | Ser | Leu | Leu | Tyr | Lys 555 | Lys | Val | |
| AAT | GAG | GCT | CAG | TAT | CGC | AGC | CAC | CTG | GCC | AAT | GAG | ATG | ATG | ATG | TAC | 1730 |
| Asn | Glu | Ala | Gln 560 | Tyr | Arg | Ser | His | Leu 565 | Ala | Asn | Glu | Met | Met 570 | Met | Tyr | |
| CAC | ATG | AAG | GTC | TCC | GAC | GAT | GAG | TAT | ACC | AAA | CTT | CTC | CAT | GAT | GGG | 1778 |
| His | Met | Lys 575 | Val | Ser | Asp | Asp | Glu 580 | Tyr | Thr | Lys | Leu | Leu 585 | His | Asp | Gly | |
| ATC | CAG | CCT | GTG | GCT | GCC | ATT | GAC | TCC | AAT | TTT | GCA | AGT | TTC | ACC | TAT | 1826 |
| Ile | Gln | Pro | Val 590 | Ala | Ala | Ile | Asp | Ser 595 | Asn | Phe | Ala | Ser | Phe 600 | Thr | Tyr 605 | |

| | | | | | | | | | | | | | | | | |
|---|---|---|---|---|---|---|---|---|---|---|---|---|---|---|---|---|
| ACC | CCT | CGT | TCC | CTG | CCC | GAG | GAT | GAC | ACG | TCC | ATG | GCC | ATC | CTG | AGC | 1874 |
| Thr | Pro | Arg | Ser | Leu 610 | Pro | Glu | Asp | Asp 615 | Thr | Ser | Met | Ala | Ile | Leu 620 | Ser | |
| ATG | CTG | CAG | GAC | ATG | AAT | TTC | ATC | AAC | AAC | TAC | AAA | ATT | GAC | TGC | CCG | 1922 |
| Met | Leu | Gln | Asp 625 | Met | Asn | Phe | Ile | Asn 630 | Asn | Tyr | Lys | Ile | Asp 635 | Cys | Pro | |
| ACC | CTG | GCC | CGG | TTC | TGT | TTG | ATG | GTG | AAG | AAG | GGC | TAC | CGG | GAT | CCC | 1970 |
| Thr | Leu | Ala | Arg 640 | Phe | Cys | Leu | Met | Val 645 | Lys | Lys | Gly | Tyr | Arg 650 | Asp | Pro | |
| CCC | TAC | CAC | AAC | TGG | ATG | CAC | GCC | TTT | TCT | GTC | TCC | CAC | TTC | TGC | TAC | 2018 |
| Pro | Tyr 655 | His | Asn | Trp | Met | His 660 | Ala | Phe | Ser | Val | Ser 665 | His | Phe | Cys | Tyr | |
| CTG | CTC | TAC | AAG | AAC | CTG | GAG | CTC | ACC | AAC | TAC | CTC | GAG | GAC | ATC | GAG | 2066 |
| Leu 670 | Leu | Tyr | Lys | Asn | Leu 675 | Glu | Leu | Thr | Asn | Tyr 680 | Leu | Glu | Asp | Ile | Glu 685 | |
| ATC | TTT | GCC | TTG | TTT | ATT | TCC | TGC | ATG | TGT | CAT | GAC | CTG | GAC | CAC | AGA | 2114 |
| Ile | Phe | Ala | Leu | Phe 690 | Ile | Ser | Cys | Met | Cys 695 | His | Asp | Leu | Asp | His 700 | Arg | |
| GGC | ACA | AAC | AAC | TCT | TTC | CAG | GTG | GCC | TCG | AAA | TCT | GTG | CTG | GCT | GCG | 2162 |
| Gly | Thr | Asn | Asn 705 | Ser | Phe | Gln | Val | Ala 710 | Ser | Lys | Ser | Val | Leu 715 | Ala | Ala | |
| CTC | TAC | AGC | TCT | GAG | GGC | TCC | GTC | ATG | GAG | AGG | CAC | CAC | TTT | GCT | CAG | 2210 |
| Leu | Tyr | Ser 720 | Ser | Glu | Gly | Ser | Val 725 | Met | Glu | Arg | His | His 730 | Phe | Ala | Gln | |
| GCC | ATC | GCC | ATC | CTC | AAC | ACC | CAC | GGC | TGC | AAC | ATC | TTT | GAT | CAT | TTC | 2258 |
| Ala | Ile 735 | Ala | Ile | Leu | Asn | Thr 740 | His | Gly | Cys | Asn | Ile 745 | Phe | Asp | His | Phe | |
| TCC | CGG | AAG | GAC | TAT | CAG | CGC | ATG | CTG | GAT | CTG | ATG | CGG | GAC | ATC | ATC | 2306 |
| Ser | Arg | Lys 750 | Asp | Tyr | Gln | Arg 755 | Met | Leu | Asp | Leu | Met 760 | Arg | Asp | Ile | Ile 765 | |
| TTG | GCC | ACA | GAC | CTG | GCC | CAC | CAT | CTC | CGC | ATC | TTC | AAG | GAC | CTC | CAG | 2354 |
| Leu | Ala | Thr | Asp 770 | Leu | Ala | His | His | Leu 775 | Arg | Ile | Phe | Lys | Asp 780 | Leu | Gln | |
| AAG | ATG | GCT | GAG | GTG | GGC | TAC | GAC | CGA | AAC | AAC | AAG | CAG | CAC | CAC | AGA | 2402 |
| Lys | Met | Ala | Glu 785 | Val | Gly | Tyr | Asp | Arg 790 | Asn | Asn | Lys | Gln | His 795 | His | Arg | |
| CTT | CTC | CTC | TGC | CTC | CTC | ATG | ACC | TCC | TGT | GAC | CTC | TCT | GAC | CAG | ACC | 2450 |
| Leu | Leu | Leu 800 | Cys | Leu | Leu | Met | Thr 805 | Ser | Cys | Asp | Leu | Ser 810 | Asp | Gln | Thr | |
| AAG | GGC | TGG | AAG | ACT | ACG | AGA | AAG | ATC | GCG | GAG | CTG | ATC | TAC | AAA | GAA | 2498 |
| Lys | Gly 815 | Trp | Lys | Thr | Thr | Arg 820 | Lys | Ile | Ala | Glu | Leu 825 | Ile | Tyr | Lys | Glu | |
| TTC | TTC | TCC | CAG | GGA | GAC | CTG | GAG | AAG | GCC | ATG | GGC | AAC | AGG | CCG | ATG | 2546 |
| Phe 830 | Phe | Ser | Gln | Gly | Asp 835 | Leu | Glu | Lys | Ala | Met 840 | Gly | Asn | Arg | Pro | Met 845 | |
| GAG | ATG | ATG | GAC | CGG | GAG | AAG | GCC | TAT | ATC | CCT | GAG | CTG | CAA | ATC | AGC | 2594 |
| Glu | Met | Met | Asp 850 | Arg | Glu | Lys | Ala | Tyr 855 | Ile | Pro | Glu | Leu | Gln 860 | Ile | Ser | |
| TTC | ATG | GAG | CAC | ATT | GCA | ATG | CCC | ATC | TAC | AAG | CTG | TTG | CAG | GAC | CTG | 2642 |
| Phe | Met | Glu | His 865 | Ile | Ala | Met | Pro | Ile 870 | Tyr | Lys | Leu | Leu | Gln 875 | Asp | Leu | |
| TTC | CCC | AAA | GCG | GCA | GAG | CTG | TAC | GAG | CGC | GTG | GCC | TCC | AAC | CGT | GAG | 2690 |
| Phe | Pro | Lys 880 | Ala | Ala | Glu | Leu | Tyr 885 | Glu | Arg | Val | Ala | Ser 890 | Asn | Arg | Glu | |
| CAC | TGG | ACC | AAG | GTG | TCC | CAC | AAG | TTC | ACC | ATC | CGC | GGC | CTC | CCA | AGT | 2738 |
| His | Trp 895 | Thr | Lys | Val | Ser | His 900 | Lys | Phe | Thr | Ile | Arg 905 | Gly | Leu | Pro | Ser | |
| AAC | AAC | TCG | CTG | GAC | TTC | CTG | GAT | GAG | GAG | TAC | GAG | GTG | CCT | GAT | CTG | 2786 |
| Asn | Asn | Ser | Leu 910 | Asp | Phe | Leu | Asp | Glu 915 | Glu | Tyr | Glu | Val | Pro 920 | Asp | Leu 925 | |

```
GAT GGC ACT AGG GCC CCC ATC AAT GGC TGC TGC AGC CTT GAT GCT GAG        2834
Asp Gly Thr Arg Ala Pro Ile Asn Gly Cys Cys Ser Leu Asp Ala Glu
            930                 935                 940

TGACTCGAGC GTCATATTAA TGGACGCAAA GCAAGGAAAT TGCGAGCGGG AAATAAGAAA       2894

CGATAGAAGT AGGAATCGAT ACCCGGTGCG TGCACATAAC AGTCTTTTAC CAATTAACAG       2954

GAGAGATTGA AGTGTCGAGA TACGAAATGA AATTTACTAC GACTACCGTA AAGAAATGCA       3014

TAAGCTCTGT TAGAGAAAAA TTGGTAGCCA                                        3044
```

( 2 ) INFORMATION FOR SEQ ID NO:45:

( i ) SEQUENCE CHARACTERISTICS:
        ( A ) LENGTH: 941 amino acids
        ( B ) TYPE: amino acid
        ( D ) TOPOLOGY: linear ( i i ) MOLECULE TYPE: protein ( x i ) SEQUENCE DESCRIPTION: SEQ ID NO:45:

```
Met Gly Gln Ala Cys Gly His Ser Ile Leu Cys Arg Ser Gln Gln Tyr
 1               5                  10                  15

Pro Ala Ala Arg Pro Ala Glu Pro Arg Gly Gln Gln Val Phe Leu Lys
                20                  25                  30

Pro Asp Glu Pro Pro Pro Pro Gln Pro Cys Ala Asp Ser Leu Gln
                35              40                  45

Asp Ala Leu Leu Ser Leu Gly Ser Val Ile Asp Ile Ser Gly Leu Gln
        50                  55                  60

Arg Ala Val Lys Glu Ala Leu Ser Ala Val Leu Pro Arg Val Glu Thr
 65                  70                  75                  80

Val Tyr Thr Tyr Leu Leu Asp Gly Glu Ser Gln Leu Val Cys Glu Asp
                    85                  90                  95

Pro Pro His Glu Leu Pro Gln Glu Gly Lys Val Arg Glu Ala Ile Ile
                100                 105                 110

Ser Gln Lys Arg Leu Gly Cys Asn Gly Leu Gly Phe Ser Asp Leu Pro
            115                 120                 125

Gly Lys Pro Leu Ala Arg Leu Val Ala Pro Leu Ala Pro Asp Thr Gln
        130                 135                 140

Val Leu Val Met Pro Leu Ala Asp Lys Glu Ala Gly Ala Val Ala Ala
145                 150                 155                 160

Val Ile Leu Val His Cys Gly Gln Leu Ser Asp Asn Glu Glu Trp Ser
                    165                 170                 175

Leu Gln Ala Val Glu Lys His Thr Leu Val Ala Leu Arg Arg Val Gln
                180                 185                 190

Val Leu Gln Gln Arg Gly Pro Arg Glu Ala Pro Arg Ala Val Gln Asn
            195                 200                 205

Pro Pro Glu Gly Thr Ala Glu Asp Gln Lys Gly Gly Ala Ala Tyr Thr
        210                 215                 220

Asp Arg Asp Arg Lys Ile Leu Gln Leu Cys Gly Glu Leu Tyr Asp Leu
225                 230                 235                 240

Asp Ala Ser Ser Leu Gln Leu Lys Val Leu Gln Tyr Leu Gln Gln Glu
                    245                 250                 255

Thr Arg Ala Ser Arg Cys Cys Leu Leu Leu Val Ser Glu Asp Asn Leu
                260                 265                 270

Gln Leu Ser Cys Lys Val Ile Gly Asp Lys Val Leu Gly Glu Glu Val
            275                 280                 285

Ser Phe Pro Leu Thr Gly Cys Leu Gly Gln Val Val Glu Asp Lys Lys
        290                 295                 300
```

```
Ser  Ile  Gln  Leu  Lys  Asp  Leu  Thr  Ser  Glu  Asp  Val  Gln  Gln  Leu  Gln
305                 310                 315                 320

Ser  Met  Leu  Gly  Cys  Glu  Leu  Gln  Ala  Met  Leu  Cys  Val  Pro  Val  Ile
                    325                 330                      335

Ser  Arg  Ala  Thr  Asp  Gln  Val  Val  Ala  Leu  Ala  Cys  Ala  Phe  Asn  Lys
               340                 345                      350

Leu  Glu  Gly  Asp  Leu  Phe  Thr  Asp  Glu  Asp  Glu  His  Val  Ile  Gln  His
          355                 360                      365

Cys  Phe  His  Tyr  Thr  Ser  Thr  Val  Leu  Thr  Ser  Thr  Leu  Ala  Phe  Gln
370                      375                 380

Lys  Glu  Gln  Lys  Leu  Lys  Cys  Glu  Cys  Gln  Ala  Leu  Leu  Gln  Val  Ala
385                 390                 395                           400

Lys  Asn  Leu  Phe  Thr  His  Leu  Asp  Asp  Val  Ser  Val  Leu  Leu  Gln  Glu
               405                 410                           415

Ile  Ile  Thr  Glu  Ala  Arg  Asn  Leu  Ser  Asn  Ala  Glu  Ile  Cys  Ser  Val
          420                      425                      430

Phe  Leu  Leu  Asp  Gln  Asn  Glu  Leu  Val  Ala  Lys  Val  Phe  Asp  Gly  Gly
          435                 440                 445

Val  Val  Asp  Asp  Glu  Ser  Tyr  Gln  Ile  Arg  Ile  Pro  Ala  Asp  Gln  Gly
     450                 455                 460

Ile  Ala  Gly  His  Val  Ala  Thr  Thr  Gly  Gln  Ile  Leu  Asn  Ile  Pro  Asp
465                 470                 475                      480

Ala  Tyr  Ala  His  Pro  Leu  Phe  Tyr  Arg  Gly  Val  Asp  Asp  Ser  Thr  Gly
               485                 490                 495

Phe  Arg  Thr  Arg  Asn  Ile  Leu  Cys  Phe  Pro  Ile  Lys  Asn  Glu  Asn  Gln
               500                 505                 510

Glu  Val  Ile  Gly  Val  Ala  Glu  Leu  Val  Asn  Lys  Ile  Asn  Gly  Pro  Trp
          515                 520                 525

Phe  Ser  Lys  Phe  Asp  Glu  Asp  Leu  Ala  Thr  Ala  Phe  Ser  Ile  Tyr  Cys
     530                 535                 540

Gly  Ile  Ser  Ile  Ala  His  Ser  Leu  Leu  Tyr  Lys  Lys  Val  Asn  Glu  Ala
545                 550                 555                      560

Gln  Tyr  Arg  Ser  His  Leu  Ala  Asn  Glu  Met  Met  Met  Tyr  His  Met  Lys
               565                 570                      575

Val  Ser  Asp  Asp  Glu  Tyr  Thr  Lys  Leu  Leu  His  Asp  Gly  Ile  Gln  Pro
          580                 585                 590

Val  Ala  Ala  Ile  Asp  Ser  Asn  Phe  Ala  Ser  Phe  Thr  Tyr  Thr  Pro  Arg
          595                 600                 605

Ser  Leu  Pro  Glu  Asp  Asp  Thr  Ser  Met  Ala  Ile  Leu  Ser  Met  Leu  Gln
     610                 615                 620

Asp  Met  Asn  Phe  Ile  Asn  Asn  Tyr  Lys  Ile  Asp  Cys  Pro  Thr  Leu  Ala
625                 630                 635                           640

Arg  Phe  Cys  Leu  Met  Val  Lys  Lys  Gly  Tyr  Arg  Asp  Pro  Pro  Tyr  His
               645                 650                 655

Asn  Trp  Met  His  Ala  Phe  Ser  Val  Ser  His  Phe  Cys  Tyr  Leu  Leu  Tyr
               660                 665                 670

Lys  Asn  Leu  Glu  Leu  Thr  Asn  Tyr  Leu  Glu  Asp  Ile  Glu  Ile  Phe  Ala
     675                 680                 685

Leu  Phe  Ile  Ser  Cys  Met  Cys  His  Asp  Leu  Asp  His  Arg  Gly  Thr  Asn
     690                 695                 700

Asn  Ser  Phe  Gln  Val  Ala  Ser  Lys  Ser  Val  Leu  Ala  Ala  Leu  Tyr  Ser
705                 710                 715                           720

Ser  Glu  Gly  Ser  Val  Met  Glu  Arg  His  His  Phe  Ala  Gln  Ala  Ile  Ala
```

-continued

```
                    725                         730                         735
Ile Leu Asn Thr His Gly Cys Asn Ile Phe Asp His Phe Ser Arg Lys
            740                 745                 750

Asp Tyr Gln Arg Met Leu Asp Leu Met Arg Asp Ile Ile Leu Ala Thr
        755                 760                 765

Asp Leu Ala His His Leu Arg Ile Phe Lys Asp Leu Gln Lys Met Ala
    770                 775                 780

Glu Val Gly Tyr Asp Arg Asn Asn Lys Gln His His Arg Leu Leu Leu
785                 790                 795                     800

Cys Leu Leu Met Thr Ser Cys Asp Leu Ser Asp Gln Thr Lys Gly Trp
                805                 810                 815

Lys Thr Thr Arg Lys Ile Ala Glu Leu Ile Tyr Lys Glu Phe Phe Ser
            820                 825                 830

Gln Gly Asp Leu Glu Lys Ala Met Gly Asn Arg Pro Met Glu Met Met
            835                 840                 845

Asp Arg Glu Lys Ala Tyr Ile Pro Glu Leu Gln Ile Ser Phe Met Glu
        850                 855                 860

His Ile Ala Met Pro Ile Tyr Lys Leu Leu Gln Asp Leu Phe Pro Lys
865                 870                 875                     880

Ala Ala Glu Leu Tyr Glu Arg Val Ala Ser Asn Arg Glu His Trp Thr
                885                 890                 895

Lys Val Ser His Lys Phe Thr Ile Arg Gly Leu Pro Ser Asn Asn Ser
            900                 905                 910

Leu Asp Phe Leu Asp Glu Gln Tyr Glu Val Pro Asp Leu Asp Gly Thr
            915                 920                 925

Arg Ala Pro Ile Asn Gly Cys Cys Ser Leu Asp Ala Glu
            930                 935                 940
```

( 2 ) INFORMATION FOR SEQ ID NO:46:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA ( i v ) ANTI-SENSE: YES ( x i ) SEQUENCE DESCRIPTION: SEQ ID NO:46:

TCRTTNGTNG TNCCYTTCAT RTT          23

( 2 ) INFORMATION FOR SEQ ID NO:47:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:47:

Asn Met Lys Gly Thr Thr Asn Asp
    1            5

( 2 ) INFORMATION FOR SEQ ID NO:48:

( i ) SEQUENCE CHARACTERISTICS:
        ( A ) LENGTH: 1625 base pairs
        ( B ) TYPE: nucleic acid
        ( C ) STRANDEDNESS: single 5,800,987

103

104

-continued ( D ) TOPOLOGY: linear ( i i ) MOLECULE TYPE: cDNA ( i x ) FEATURE:
    ( A ) NAME/KEY: CDS
    ( B ) LOCATION: 12..1616

( x i ) SEQUENCE DESCRIPTION: SEQ ID NO:48:

```
GAATTCTGAT C ATG GGG TCT AGT GCC ACA GAG ATT GAA GAA TTG GAA AAC          50
           Met Gly Ser Ser Ala Thr Glu Ile Glu Glu Leu Glu Asn
            1               5                  10

ACC ACT TTT AAG TAT CTT ACA GGA GAA CAG ACT GAA AAA ATG TGG CAG          98
Thr Thr Phe Lys Tyr Leu Thr Gly Glu Gln Thr Glu Lys Met Trp Gln
        15              20                  25

CGC CTG AAA GGA ATA CTA AGA TGC TTG GTG AAG CAG CTG GAA AGA GGT         146
Arg Leu Lys Gly Ile Leu Arg Cys Leu Val Lys Gln Leu Glu Arg Gly
 30              35                  40                  45

GAT GTT AAC GTC GTC GAC TTA AAG AAG AAT ATT GAA TAT GCG GCA TCT         194
Asp Val Asn Val Val Asp Leu Lys Lys Asn Ile Glu Tyr Ala Ala Ser
                50                  55                  60

GTG CTG GAA GCA GTT TAT ATC GAT GAA ACA AGA AGA CTT CTG GAT ACT         242
Val Leu Glu Ala Val Tyr Ile Asp Glu Thr Arg Arg Leu Leu Asp Thr
             65                  70                  75

GAA GAT GAG CTC AGT GAC ATT CAG ACT GAC TCA GTC CCA TCT GAA GTC         290
Glu Asp Glu Leu Ser Asp Ile Gln Thr Asp Ser Val Pro Ser Glu Val
         80                  85                  90

CGG GAC TGG TTG GCT TCT ACC TTT ACA CGG AAA ATG GGG ATG ACA AAA         338
Arg Asp Trp Leu Ala Ser Thr Phe Thr Arg Lys Met Gly Met Thr Lys
     95                 100                 105

AAG AAA CCT GAG GAA AAA CCA AAA TTT CGG AGC ATT GTG CAT GCT GTT         386
Lys Lys Pro Glu Glu Lys Pro Lys Phe Arg Ser Ile Val His Ala Val
110                 115                 120                 125

CAA GCT GGA ATT TTT GTG GAA AGA ATG TAC CGA AAA ACA TAT CAT ATG         434
Gln Ala Gly Ile Phe Val Glu Arg Met Tyr Arg Lys Thr Tyr His Met
                130                 135                 140

GTT GGT TTG GCA TAT CCA GCA GCT GTC ATC GTA ACA TTA AAG GAT GTT         482
Val Gly Leu Ala Tyr Pro Ala Ala Val Ile Val Thr Leu Lys Asp Val
            145                 150                 155

GAT AAA TGG TCT TTC GAT GTA TTT GCC CTA AAT GAA GCA AGT GGA GAG         530
Asp Lys Trp Ser Phe Asp Val Phe Ala Leu Asn Glu Ala Ser Gly Glu
        160                 165                 170

CAT AGT CTG AAG TTT ATG ATT TAT GAA CTG TTT ACC AGA TAT GAT CTT         578
His Ser Leu Lys Phe Met Ile Tyr Glu Leu Phe Thr Arg Tyr Asp Leu
    175                 180                 185

ATC AAC CGT TTC AAG ATT CCT GTT TCT TGC CTA ATC ACC TTT GCA GAA         626
Ile Asn Arg Phe Lys Ile Pro Val Ser Cys Leu Ile Thr Phe Ala Glu
190                 195                 200                 205

GCT TTA GAA GTT GGT TAC AGC AAG TAC AAA AAT CCA TAT CAC AAT TTG         674
Ala Leu Glu Val Gly Tyr Ser Lys Tyr Lys Asn Pro Tyr His Asn Leu
                210                 215                 220

ATT CAT GCA GCT GAT GTC ACT CAA ACT GTG CAT TAC ATA ATG CTT CAT         722
Ile His Ala Ala Asp Val Thr Gln Thr Val His Tyr Ile Met Leu His
            225                 230                 235

ACA GGT ATC ATG CAC TGG CTC ACT GAA CTG GAA ATT TTA GCA ATG GTC         770
Thr Gly Ile Met His Trp Leu Thr Glu Leu Glu Ile Leu Ala Met Val
        240                 245                 250

TTT GCT GCT GCC ATT CAT GAT TAT GAG CAT ACA GGG ACA ACA AAC AAC         818
Phe Ala Ala Ala Ile His Asp Tyr Glu His Thr Gly Thr Thr Asn Asn
    255                 260                 265

TTT CAC ATT CAG ACA AGG TCA GAT GTT GCC ATT TTG TAT AAT GAT CGC         866
Phe His Ile Gln Thr Arg Ser Asp Val Ala Ile Leu Tyr Asn Asp Arg
```

-continued

| | | | | | | | | | | | | | | | | |
|---|---|---|---|---|---|---|---|---|---|---|---|---|---|---|---|---|
| | 270 | | | | | 275 | | | | | 280 | | | | | 285 |

```
TCT  GTC  CTT  GAG  AAT  CAC  CAC  GTG  AGT  GCA  GCT  TAT  CGA  CTT  ATG  CAA        914
Ser  Val  Leu  Glu  Asn  His  His  Val  Ser  Ala  Ala  Tyr  Arg  Leu  Met  Gln
                         290                 295                      300

GAA  GAA  GAA  ATG  AAT  ATC  TTG  ATA  AAT  TTA  TCC  AAA  GAT  GAC  TGG  AGG        962
Glu  Glu  Glu  Met  Asn  Ile  Leu  Ile  Asn  Leu  Ser  Lys  Asp  Asp  Trp  Arg
                    305                           310                 315

GAT  CTT  CGG  AAC  CTA  GTG  ATT  GAA  ATG  GTT  TTA  TCT  ACA  GAC  ATG  TCA       1010
Asp  Leu  Arg  Asn  Leu  Val  Ile  Glu  Met  Val  Leu  Ser  Thr  Asp  Met  Ser
               320                      325                      330

GGT  CAC  TTC  CAG  CAA  ATT  AAA  AAT  ATA  AGA  AAC  AGT  TTG  CAG  CAG  CCT       1058
Gly  His  Phe  Gln  Gln  Ile  Lys  Asn  Ile  Arg  Asn  Ser  Leu  Gln  Gln  Pro
          335                      340                 345

GAA  GGG  ATT  GAC  AGA  GCC  AAA  ACC  ATG  TCC  CTG  ATT  CTC  CAC  GCA  GCA       1106
Glu  Gly  Ile  Asp  Arg  Ala  Lys  Thr  Met  Ser  Leu  Ile  Leu  His  Ala  Ala
350                      355                      360                      365

GAC  ATC  AGC  CAC  CCA  GCC  AAA  TCC  TGG  AAG  CTG  CAT  TAT  CGG  TGG  ACC       1154
Asp  Ile  Ser  His  Pro  Ala  Lys  Ser  Trp  Lys  Leu  His  Tyr  Arg  Trp  Thr
                    370                      375                 380

ATG  GCC  CTA  ATG  GAG  GAG  TTT  TTC  CTG  CAG  GGA  GAT  AAA  GAA  GCT  GAA       1202
Met  Ala  Leu  Met  Glu  Glu  Phe  Phe  Leu  Gln  Gly  Asp  Lys  Glu  Ala  Glu
               385                      390                      395

TTA  GGG  CTT  CCA  TTT  TCC  CCA  CTT  TGT  GAT  CGG  AAG  TCA  ACC  ATG  GTG       1250
Leu  Gly  Leu  Pro  Phe  Ser  Pro  Leu  Cys  Asp  Arg  Lys  Ser  Thr  Met  Val
          400                      405                      410

GCC  CAG  TCA  CAA  ATA  GGT  TTC  ATC  GAT  TTC  ATA  GTA  GAG  CCA  ACA  TTT       1298
Ala  Gln  Ser  Gln  Ile  Gly  Phe  Ile  Asp  Phe  Ile  Val  Glu  Pro  Thr  Phe
     415                      420                 425

TCT  CTT  CTG  ACA  GAC  TCA  ACA  GAG  AAA  ATT  GTT  ATT  CCT  CTT  ATA  GAG       1346
Ser  Leu  Leu  Thr  Asp  Ser  Thr  Glu  Lys  Ile  Val  Ile  Pro  Leu  Ile  Glu
430                      435                      440                      445

GAA  GCC  TCA  AAA  GCC  GAA  ACT  TCT  TCC  TAT  GTG  GCA  AGC  AGC  TCA  ACC       1394
Glu  Ala  Ser  Lys  Ala  Glu  Thr  Ser  Ser  Tyr  Val  Ala  Ser  Ser  Ser  Thr
                    450                      455                 460

ACC  ATT  GTG  GGG  TTA  CAC  ATT  GCT  GAT  GCA  CTA  AGA  CGA  TCA  AAT  ACA       1442
Thr  Ile  Val  Gly  Leu  His  Ile  Ala  Asp  Ala  Leu  Arg  Arg  Ser  Asn  Thr
               465                      470                 475

AAA  GGC  TCC  ATG  AGT  GAT  GGG  TCC  TAT  TCC  CCA  GAC  TAC  TCC  CTT  GCA       1490
Lys  Gly  Ser  Met  Ser  Asp  Gly  Ser  Tyr  Ser  Pro  Asp  Tyr  Ser  Leu  Ala
          480                      485                      490

GCA  GTG  GAC  CTG  AAG  AGT  TTC  AAG  AAC  AAC  CTG  GTG  GAC  ATC  ATT  CAG       1538
Ala  Val  Asp  Leu  Lys  Ser  Phe  Lys  Asn  Asn  Leu  Val  Asp  Ile  Ile  Gln
     495                      500                      505

CAG  AAC  AAA  GAG  AGG  TGG  AAA  GAG  TTA  GCT  GCA  CAA  GAA  GCA  AGA  ACC       1586
Gln  Asn  Lys  Glu  Arg  Trp  Lys  Glu  Leu  Ala  Ala  Gln  Glu  Ala  Arg  Thr
510                      515                      520                      525

AGT  TCA  CAG  AAG  TGT  GAG  TTT  ATT  CAT  CAG  TAACTCGAG                          1625
Ser  Ser  Gln  Lys  Cys  Glu  Phe  Ile  His  Gln
                    530                      535
```

( 2 ) INFORMATION FOR SEQ ID NO:49:

( i ) SEQUENCE CHARACTERISTICS:
        ( A ) LENGTH: 535 amino acids
        ( B ) TYPE: amino acid
        ( D ) TOPOLOGY: linear ( i i ) MOLECULE TYPE: protein ( x i ) SEQUENCE DESCRIPTION: SEQ ID NO:49:

```
Met  Gly  Ser  Ser  Ala  Thr  Glu  Ile  Glu  Glu  Leu  Glu  Asn  Thr  Thr  Phe
 1              5                        10                       15
```

```
Lys Tyr Leu Thr Gly Glu Gln Thr Glu Lys Met Trp Gln Arg Leu Lys
         20                  25                  30

Gly Ile Leu Arg Cys Leu Val Lys Gln Leu Glu Arg Gly Asp Val Asn
             35                  40                  45

Val Val Asp Leu Lys Lys Asn Ile Glu Tyr Ala Ala Ser Val Leu Glu
     50                  55                  60

Ala Val Tyr Ile Asp Glu Thr Arg Arg Leu Leu Asp Thr Glu Asp Glu
 65                  70                  75                  80

Leu Ser Asp Ile Gln Thr Asp Ser Val Pro Ser Glu Val Arg Asp Trp
                 85                  90                  95

Leu Ala Ser Thr Phe Thr Arg Lys Met Gly Met Thr Lys Lys Lys Pro
             100                 105                 110

Glu Glu Lys Pro Lys Phe Arg Ser Ile Val His Ala Val Gln Ala Gly
         115                 120                 125

Ile Phe Val Glu Arg Met Tyr Arg Lys Thr Tyr His Met Val Gly Leu
     130                 135                 140

Ala Tyr Pro Ala Ala Val Ile Val Thr Leu Lys Asp Val Asp Lys Trp
145                 150                 155                 160

Ser Phe Asp Val Phe Ala Leu Asn Glu Ala Ser Gly Glu His Ser Leu
                 165                 170                 175

Lys Phe Met Ile Tyr Glu Leu Phe Thr Arg Tyr Asp Leu Ile Asn Arg
             180                 185                 190

Phe Lys Ile Pro Val Ser Cys Leu Ile Thr Phe Ala Glu Ala Leu Glu
         195                 200                 205

Val Gly Tyr Ser Lys Tyr Lys Asn Pro Tyr His Asn Leu Ile His Ala
     210                 215                 220

Ala Asp Val Thr Gln Thr Val His Tyr Ile Met Leu His Thr Gly Ile
225                 230                 235                 240

Met His Trp Leu Thr Glu Leu Glu Ile Leu Ala Met Val Phe Ala Ala
                 245                 250                 255

Ala Ile His Asp Tyr Glu His Thr Gly Thr Thr Asn Asn Phe His Ile
             260                 265                 270

Gln Thr Arg Ser Asp Val Ala Ile Leu Tyr Asn Asp Arg Ser Val Leu
         275                 280                 285

Glu Asn His His Val Ser Ala Ala Tyr Arg Leu Met Gln Glu Glu Glu
     290                 295                 300

Met Asn Ile Leu Ile Asn Leu Ser Lys Asp Asp Trp Arg Asp Leu Arg
305                 310                 315                 320

Asn Leu Val Ile Glu Met Val Leu Ser Thr Asp Met Ser Gly His Phe
                 325                 330                 335

Gln Gln Ile Lys Asn Ile Arg Asn Ser Leu Gln Gln Pro Glu Gly Ile
             340                 345                 350

Asp Arg Ala Lys Thr Met Ser Leu Ile Leu His Ala Ala Asp Ile Ser
         355                 360                 365

His Pro Ala Lys Ser Trp Lys Leu His Tyr Arg Trp Thr Met Ala Leu
     370                 375                 380

Met Glu Glu Phe Phe Leu Gln Gly Asp Lys Glu Ala Glu Leu Gly Leu
385                 390                 395                 400

Pro Phe Ser Pro Leu Cys Asp Arg Lys Ser Thr Met Val Ala Gln Ser
                 405                 410                 415

Gln Ile Gly Phe Ile Asp Phe Ile Val Glu Pro Thr Phe Ser Leu Leu
             420                 425                 430

Thr Asp Ser Thr Glu Lys Ile Val Ile Pro Leu Ile Glu Glu Ala Ser
```

|     |     |     |     |     |     |     |     |     |     |     |     |     |     |     |     |
| --- | --- | --- | --- | --- | --- | --- | --- | --- | --- | --- | --- | --- | --- | --- | --- |
|     |     |     |     | 435 |     |     |     | 440 |     |     |     | 445 |     |     |     |
| Lys | Ala | Glu | Thr | Ser | Ser | Tyr | Val | Ala | Ser | Ser | Ser | Thr | Thr | Ile | Val |
|     | 450 |     |     |     |     | 455 |     |     |     |     | 460 |     |     |     |     |
| Gly | Leu | His | Ile | Ala | Asp | Ala | Leu | Arg | Arg | Ser | Asn | Thr | Lys | Gly | Ser |
| 465 |     |     |     |     | 470 |     |     |     |     | 475 |     |     |     |     | 480 |
| Met | Ser | Asp | Gly | Ser | Tyr | Ser | Pro | Asp | Tyr | Ser | Leu | Ala | Ala | Val | Asp |
|     |     |     |     | 485 |     |     |     |     | 490 |     |     |     |     | 495 |     |
| Leu | Lys | Ser | Phe | Lys | Asn | Asn | Leu | Val | Asp | Ile | Ile | Gln | Gln | Asn | Lys |
|     |     |     | 500 |     |     |     |     | 505 |     |     |     |     | 510 |     |     |
| Glu | Arg | Trp | Lys | Glu | Leu | Ala | Ala | Gln | Glu | Ala | Arg | Thr | Ser | Ser | Gln |
|     |     | 515 |     |     |     |     | 520 |     |     |     |     | 525 |     |     |     |
| Lys | Cys | Glu | Phe | Ile | His | Gln |     |     |     |     |     |     |     |     |     |
|     | 530 |     |     |     |     | 535 |     |     |     |     |     |     |     |     |     |

( 2 ) INFORMATION FOR SEQ ID NO:50:

( i ) SEQUENCE CHARACTERISTICS:
        ( A ) LENGTH: 2693 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 176..2077

( x i ) SEQUENCE DESCRIPTION: SEQ ID NO:50:

```
GTCGCTTCAA   TATTTCAAAA   TGGATCCGGT   TCTGTGGCGG   GTGCGAGAGT   GAGGCTGTGG         60

GGGACCTCCA   GGCCGAACCT   CCGCGAAGCC   TCGGCCTTCT   GCGTGCCCTG   GCCCCGGGAG        120

GATAAGGATT   TCCCTTCCCT   CCTACTTGCG   CGCGGAGCCG   AGCTCTTGTT   GAGCT ATG        178
                                                                     Met
                                                                      1
```

|     |     |     |     |     |     |     |     |     |     |     |     |     |     |     |     |
| --- | --- | --- | --- | --- | --- | --- | --- | --- | --- | --- | --- | --- | --- | --- | --- |
| GAG | TCG | CCA | ACC | AAG | GAG | ATT | GAA | GAA | TTT | GAG | AGC | AAC | TCT | CTG | AAA | 226 |
| Glu | Ser | Pro | Thr | Lys | Glu | Ile | Glu | Glu | Phe | Glu | Ser | Asn | Ser | Leu | Lys |
|     |     |     | 5   |     |     |     |     | 10  |     |     |     |     | 15  |     |     |
| TAC | CTG | CAA | CCG | GAA | CAG | ATC | GAG | AAA | ATC | TGG | CTT | CGG | CTC | CGC | GGG | 274 |
| Tyr | Leu | Gln | Pro | Glu | Gln | Ile | Glu | Lys | Ile | Trp | Leu | Arg | Leu | Arg | Gly |
|     |     |     |     | 20  |     |     |     |     | 25  |     |     |     |     | 30  |     |
| CTG | AGG | AAA | TAT | AAG | AAA | ACG | TCC | CAG | AGA | TTA | CGG | TCT | TTG | GTC | AAA | 322 |
| Leu | Arg | Lys | Tyr | Lys | Lys | Thr | Ser | Gln | Arg | Leu | Arg | Ser | Leu | Val | Lys |
|     | 35  |     |     |     |     | 40  |     |     |     |     | 45  |     |     |     |     |
| CAA | TTA | GAG | AGA | GGG | GAA | GCT | TCA | GTG | GTA | GAT | CTT | AAG | AAG | AAT | TTG | 370 |
| Gln | Leu | Glu | Arg | Gly | Glu | Ala | Ser | Val | Val | Asp | Leu | Lys | Lys | Asn | Leu |
| 50  |     |     |     |     | 55  |     |     |     |     | 60  |     |     |     |     | 65  |
| GAA | TAT | GCA | GCC | ACA | GTG | CTT | GAA | TCT | GTG | TAT | ATT | GAT | GAA | ACA | AGG | 418 |
| Glu | Tyr | Ala | Ala | Thr | Val | Leu | Glu | Ser | Val | Tyr | Ile | Asp | Glu | Thr | Arg |
|     |     |     |     | 70  |     |     |     |     | 75  |     |     |     |     | 80  |     |
| AGA | CTC | CTG | GAT | ACA | GAG | GAT | GAG | CTC | AGT | GAC | ATT | CAG | TCA | GAT | GCT | 466 |
| Arg | Leu | Leu | Asp | Thr | Glu | Asp | Glu | Leu | Ser | Asp | Ile | Gln | Ser | Asp | Ala |
|     |     |     | 85  |     |     |     |     | 90  |     |     |     |     | 95  |     |     |
| GTG | CCT | TCT | GAG | GTC | CGA | GAC | TGG | CTG | GCC | TCC | ACC | TTC | ACG | CGG | CAG | 514 |
| Val | Pro | Ser | Glu | Val | Arg | Asp | Trp | Leu | Ala | Ser | Thr | Phe | Thr | Arg | Gln |
|     |     || 100 |     |     |     |     | 105 |     |     |     |     | 110 |     |     |     |
| ATG | GGG | ATG | ATG | CTC | AGG | AGG | AGC | GAC | GAG | AAG | CCC | CGG | TTC | AAG | AGC | 562 |
| Met | Gly | Met | Met | Leu | Arg | Arg | Ser | Asp | Glu | Lys | Pro | Arg | Phe | Lys | Ser |
|     | 115 |     |     |     |     | 120 |     |     |     |     | 125 |     |     |     |     |
| ATC | GTT | CAC | GCA | GTG | CAG | GCT | GGG | ATA | TTT | GTG | GAG | AGA | ATG | TAT | AGA | 610 |
| Ile | Val | His | Ala | Val | Gln | Ala | Gly | Ile | Phe | Val | Glu | Arg | Met | Tyr | Arg |
| 130 |     |     |     |     | 135 |     |     |     |     | 140 |     |     |     |     | 145 |

| | | | | | | | | | | | | | | | | |
|---|---|---|---|---|---|---|---|---|---|---|---|---|---|---|---|---|
| CGG | ACA | TCA | AAC | ATG | GTT | GGA | CTG | AGC | TAT | CCA | CCA | GCT | GTT | ATT | GAG | 658 |
| Arg | Thr | Ser | Asn | Met 150 | Val | Gly | Leu | Ser 155 | Tyr | Pro | Pro | Ala | Val | Ile 160 | Glu | |
| GCA | TTA | AAG | GAT | GTG | GAC | AAG | TGG | TCC | TTT | GAC | GTC | TTT | TCC | CTC | AAT | 706 |
| Ala | Leu | Lys 165 | Asp | Val | Asp | Lys | Trp 170 | Ser | Phe | Asp | Val | Phe 175 | Ser | Leu | Asn | |
| GAG | GCC | AGT | GGG | GAT | CAT | GCA | CTG | AAA | TTT | ATT | TTC | TAT | GAA | CTA | CTC | 754 |
| Glu | Ala | Ser 180 | Gly | Asp | His | Ala | Leu 185 | Lys | Phe | Ile | Phe | Tyr 190 | Glu | Leu | Leu | |
| ACA | CGT | TAT | GAT | CTG | ATC | AGC | CGT | TTC | AAG | ATC | CCC | ATT | TCT | GCA | CTT | 802 |
| Thr | Arg 195 | Tyr | Asp | Leu | Ile | Ser 200 | Arg | Phe | Lys | Ile | Pro 205 | Ile | Ser | Ala | Leu | |
| GTC | TCA | TTT | GTG | GAG | GCC | CTG | GAA | GTG | GGA | TAC | AGC | AAG | CAC | AAA | AAT | 850 |
| Val 210 | Ser | Phe | Val | Glu 215 | Ala | Leu | Glu | Val | Gly 220 | Tyr | Ser | Lys | His | Lys 225 | Asn | |
| CCT | TAC | CAT | AAC | TTA | ATG | CAC | GCT | GCC | GAT | GTT | ACA | CAG | ACA | GTG | CAT | 898 |
| Pro | Tyr | His | Asn | Leu 230 | Met | His | Ala | Ala | Asp 235 | Val | Thr | Gln | Thr | Val 240 | His | |
| TAC | CTC | CTC | TAT | AAG | ACA | GGA | GTG | GCG | AAC | TGG | CTG | ACG | GAG | CTG | GAG | 946 |
| Tyr | Leu | Leu | Tyr 245 | Lys | Thr | Gly | Val | Ala 250 | Asn | Trp | Leu | Thr | Glu 255 | Leu | Glu | |
| ATC | TTT | GCT | ATA | ATC | TTC | TCA | GCT | GCC | ATC | CAT | GAC | TAC | GAG | CAT | ACC | 994 |
| Ile | Phe | Ala 260 | Ile | Ile | Phe | Ser | Ala 265 | Ala | Ile | His | Asp | Tyr 270 | Glu | His | Thr | |
| GGA | ACC | ACC | AAC | AAT | TTC | CAC | ATT | CAG | ACT | CGG | TCT | GAT | CCA | GCT | ATT | 1042 |
| Gly | Thr 275 | Thr | Asn | Asn | Phe | His 280 | Ile | Gln | Thr | Arg | Ser 285 | Asp | Pro | Ala | Ile | |
| CTG | TAT | AAT | GAC | AGA | TCT | GTA | CTG | GAG | AAT | CAC | CAT | TTA | AGT | GCA | GCT | 1090 |
| Leu 290 | Tyr | Asn | Asp | Arg | Ser 295 | Val | Leu | Glu | Asn | His 300 | His | Leu | Ser | Ala | Ala 305 | |
| TAT | CGC | CTT | CTG | CAA | GAT | GAC | GAG | GAA | ATG | AAT | ATT | TTG | ATT | AAC | CTC | 1138 |
| Tyr | Arg | Leu | Leu | Gln 310 | Asp | Asp | Glu | Glu | Met 315 | Asn | Ile | Leu | Ile | Asn 320 | Leu | |
| TCA | AAG | GAT | GAC | TGG | AGG | GAG | TTT | CGA | ACC | TTG | GTA | ATT | GAA | ATG | GTG | 1186 |
| Ser | Lys | Asp | Asp 325 | Trp | Arg | Glu | Phe | Arg 330 | Thr | Leu | Val | Ile | Glu 335 | Met | Val | |
| ATG | GCC | ACA | GAT | ATG | TCT | TGT | CAC | TTC | CAA | CAA | ATC | AAA | GCA | ATG | AAG | 1234 |
| Met | Ala | Thr 340 | Asp | Met | Ser | Cys | His 345 | Phe | Gln | Gln | Ile | Lys 350 | Ala | Met | Lys | |
| ACT | GCT | CTG | CAG | CAG | CCA | GAA | GCC | ATT | GAA | AAG | CCA | AAA | GCC | TTA | TCC | 1282 |
| Thr | Ala | Leu 355 | Gln | Gln | Pro | Glu | Ala 360 | Ile | Glu | Lys | Pro | Lys 365 | Ala | Leu | Ser | |
| CTT | ATG | CTG | CAT | ACA | GCA | GAT | ATT | AGC | CAT | CCA | GCA | AAA | GCA | TGG | GAC | 1330 |
| Leu 370 | Met | Leu | His | Thr | Ala 375 | Asp | Ile | Ser | His | Pro 380 | Ala | Lys | Ala | Trp | Asp 385 | |
| CTC | CAT | CAT | CGC | TGG | ACA | ATG | TCA | CTC | CTG | GAG | GAG | TTC | TTC | AGA | CAG | 1378 |
| Leu | His | His | Arg | Trp 390 | Thr | Met | Ser | Leu | Leu 395 | Glu | Glu | Phe | Phe | Arg 400 | Gln | |
| GGT | GAC | AGA | GAA | GCA | GAG | CTG | GGG | CTG | CCT | TTT | TCT | CCT | CTG | TGT | GAC | 1426 |
| Gly | Asp | Arg | Glu 405 | Ala | Glu | Leu | Gly | Leu 410 | Pro | Phe | Ser | Pro | Leu 415 | Cys | Asp | |
| CGA | AAG | TCC | ACT | ATG | GTT | GCT | CAG | TCA | CAA | GTA | GGT | TTC | ATT | GAT | TTC | 1474 |
| Arg | Lys | Ser | Thr 420 | Met | Val | Ala | Gln | Ser 425 | Gln | Val | Gly | Phe | Ile 430 | Asp | Phe | |
| ATC | GTG | GAA | CCC | ACC | TTC | ACT | GTG | CTT | ACG | GAC | ATG | ACC | GAG | AAG | ATT | 1522 |
| Ile | Val | Glu 435 | Pro | Thr | Phe | Thr | Val 440 | Leu | Thr | Asp | Met | Thr 445 | Glu | Lys | Ile | |
| GTG | AGT | CCA | TTA | ATC | GAT | GAA | ACC | TCT | CAA | ACT | GGT | GGG | ACA | GGA | CAG | 1570 |
| Val 450 | Ser | Pro | Leu | Ile | Asp 455 | Glu | Thr | Ser | Gln | Thr 460 | Gly | Gly | Thr | Gly | Gln 465 | |

```
AGG CGT TCG AGT TTG AAT AGC ATC AGC TCG TCA GAT GCC AAG CGA TCA    1618
Arg Arg Ser Ser Leu Asn Ser Ile Ser Ser Ser Asp Ala Lys Arg Ser
            470                 475                 480

GGT GTC AAG ACC TCT GGT TCA GAG GGA AGT GCC CCG ATC AAC AAT TCT    1666
Gly Val Lys Thr Ser Gly Ser Glu Gly Ser Ala Pro Ile Asn Asn Ser
            485                 490                 495

GTC ATC TCC GTT GAC TAT AAG AGC TTT AAA GCT ACT TGG ACG GAA GTG    1714
Val Ile Ser Val Asp Tyr Lys Ser Phe Lys Ala Thr Trp Thr Glu Val
            500                 505                 510

GTG CAC ATC AAT CGG GAG AGA TGG AGG GCC AAG GTA CCC AAA GAG GAG    1762
Val His Ile Asn Arg Glu Arg Trp Arg Ala Lys Val Pro Lys Glu Glu
            515                 520                 525

AAG GCC AAG AAG GAA GCA GAG GAA AAG GCT CGC CTG GCC GCA GAG GAG    1810
Lys Ala Lys Lys Glu Ala Glu Glu Lys Ala Arg Leu Ala Ala Glu Glu
530                 535                 540                 545

CAG CAA AAG GAA ATG GAA GCC AAA AGC CAG GCT GAA GAA GGC GCA TCT    1858
Gln Gln Lys Glu Met Glu Ala Lys Ser Gln Ala Glu Glu Gly Ala Ser
                550                 555                 560

GGC AAA GCT GAG AAA AAG ACG TCT GGA GAA ACT AAG AAT CAA GTC AAT    1906
Gly Lys Ala Glu Lys Lys Thr Ser Gly Glu Thr Lys Asn Gln Val Asn
            565                 570                 575

GGA ACA CGG GCA AAC AAA AGT GAC AAC CCT CGT GGG AAA AAT TCC AAA    1954
Gly Thr Arg Ala Asn Lys Ser Asp Asn Pro Arg Gly Lys Asn Ser Lys
            580                 585                 590

GCC GAG AAG TCA TCA GGA GAA CAG CAA CAG AAT GGT GAC TTC AAA GAT    2002
Ala Glu Lys Ser Ser Gly Glu Gln Gln Gln Asn Gly Asp Phe Lys Asp
595                 600                 605

GGT AAA AAT AAG ACA GAC AAG AAG GAT CAC TCT AAC ATC GGA AAT GAT    2050
Gly Lys Asn Lys Thr Asp Lys Lys Asp His Ser Asn Ile Gly Asn Asp
610                 615                 620                 625

TCA AAG AAA ACA GAT GAT TCA CAA GAG TAAAAAAGAC CTCATAGACA          2097
Ser Lys Lys Thr Asp Asp Ser Gln Glu
                630

ATAAAAGAGG CTGCCAGTGT CTTGCATCAT TCTAGCTGAG CTTCTTCATT CTCCTTCTTC  2157

TCCTTCTTCC ACAAAGACCC ATATCTGGAG AAGGTGTACA ACTTTCAAAC ACAAGCCCCC  2217

CACCCCCTGA CCCTTGGCCT TCCCTCACAC CATCTCCTTC CAGGGGATGA ATCTTTGGGG  2277

GTTGGTTTGA GGTCTTAGAA CTCTGGGGGA TATTCCCCTG AGCAAAACAA CAACGTGAG   2337

ATTTTTACTC AAACAGAAAC AAAACATGAA GGGGCATCCT CAAAATCCTT TGCTAATGAC  2397

CTGGCTTTCA AGGCATCTGT CTGGCCTGAT GAGAATGGAC ATCCTGGATA TGCTGGGAGA  2457

GGCCTGAAAA AAGCCACACA CACAGTAATT GCCATTTTAT GACTGTCAAT GCCGTTACTT  2517

TAAATGTTGT CATTTTGCA CTGGCTACTG ATGATACAGC CATGCTGACA TTCATCACCG   2577

CAAAGATGAT GATTCCAGTC TCTGGTTCCT TTCCTGAGTC AGGAACATTT GTTTCTCCA   2637

ATTCCTTTC AGACTTAAAA TTGTTCTTAT GCTTTTTTC CCACTTCTGT AATACA        2693
```

( 2 ) INFORMATION FOR SEQ ID NO:51:

( i ) SEQUENCE CHARACTERISTICS:
        ( A ) LENGTH: 634 amino acids
        ( B ) TYPE: amino acid
        ( D ) TOPOLOGY: linear ( i i ) MOLECULE TYPE: protein ( x i ) SEQUENCE DESCRIPTION: SEQ ID NO:51:

```
Met Glu Ser Pro Thr Lys Glu Ile Glu Glu Phe Glu Ser Asn Ser Leu
 1               5                  10                  15
```

-continued

| | | | | | | | | | | | | | | |
|---|---|---|---|---|---|---|---|---|---|---|---|---|---|---|
| Lys | Tyr | Leu | Gln | Pro | Glu | Gln | Ile | Glu | Lys | Ile | Trp | Leu | Arg | Leu | Arg |
| | | | 20 | | | | 25 | | | | | 30 | | | |
| Gly | Leu | Arg | Lys | Tyr | Lys | Lys | Thr | Ser | Gln | Arg | Leu | Arg | Ser | Leu | Val |
| | | 35 | | | | | 40 | | | | | 45 | | | |
| Lys | Gln | Leu | Glu | Arg | Gly | Glu | Ala | Ser | Val | Val | Asp | Leu | Lys | Lys | Asn |
| | 50 | | | | | 55 | | | | | 60 | | | | |
| Leu | Glu | Tyr | Ala | Ala | Thr | Val | Leu | Glu | Ser | Val | Tyr | Ile | Asp | Glu | Thr |
| 65 | | | | | 70 | | | | 75 | | | | | | 80 |
| Arg | Arg | Leu | Leu | Asp | Thr | Glu | Asp | Glu | Leu | Ser | Asp | Ile | Gln | Ser | Asp |
| | | | | 85 | | | | | 90 | | | | | 95 | |
| Ala | Val | Pro | Ser | Glu | Val | Arg | Asp | Trp | Leu | Ala | Ser | Thr | Phe | Thr | Arg |
| | | | 100 | | | | | 105 | | | | | 110 | | |
| Gln | Met | Gly | Met | Met | Leu | Arg | Arg | Ser | Asp | Glu | Lys | Pro | Arg | Phe | Lys |
| | | 115 | | | | | 120 | | | | | 125 | | | |
| Ser | Ile | Val | His | Ala | Val | Gln | Ala | Gly | Ile | Phe | Val | Glu | Arg | Met | Tyr |
| | 130 | | | | | 135 | | | | | 140 | | | | |
| Arg | Arg | Thr | Ser | Asn | Met | Val | Gly | Leu | Ser | Tyr | Pro | Pro | Ala | Val | Ile |
| 145 | | | | | 150 | | | | | 155 | | | | | 160 |
| Glu | Ala | Leu | Lys | Asp | Val | Asp | Lys | Trp | Ser | Phe | Asp | Val | Phe | Ser | Leu |
| | | | | 165 | | | | | 170 | | | | | 175 | |
| Asn | Glu | Ala | Ser | Gly | Asp | His | Ala | Leu | Lys | Phe | Ile | Phe | Tyr | Glu | Leu |
| | | | 180 | | | | | 185 | | | | | 190 | | |
| Leu | Thr | Arg | Tyr | Asp | Leu | Ile | Ser | Arg | Phe | Lys | Ile | Pro | Ile | Ser | Ala |
| | | 195 | | | | | 200 | | | | | 205 | | | |
| Leu | Val | Ser | Phe | Val | Glu | Ala | Leu | Glu | Val | Gly | Tyr | Ser | Lys | His | Lys |
| | 210 | | | | | 215 | | | | | 220 | | | | |
| Asn | Pro | Tyr | His | Asn | Leu | Met | His | Ala | Ala | Asp | Val | Thr | Gln | Thr | Val |
| 225 | | | | | 230 | | | | | 235 | | | | | 240 |
| His | Tyr | Leu | Leu | Tyr | Lys | Thr | Gly | Val | Ala | Asn | Trp | Leu | Thr | Glu | Leu |
| | | | | 245 | | | | | 250 | | | | | 255 | |
| Glu | Ile | Phe | Ala | Ile | Ile | Phe | Ser | Ala | Ala | Ile | His | Asp | Tyr | Glu | His |
| | | | 260 | | | | | 265 | | | | | 270 | | |
| Thr | Gly | Thr | Thr | Asn | Asn | Phe | His | Ile | Gln | Thr | Arg | Ser | Asp | Pro | Ala |
| | | 275 | | | | | 280 | | | | | 285 | | | |
| Ile | Leu | Tyr | Asn | Asp | Arg | Ser | Val | Leu | Glu | Asn | His | His | Leu | Ser | Ala |
| | 290 | | | | | 295 | | | | | 300 | | | | |
| Ala | Tyr | Arg | Leu | Leu | Gln | Asp | Asp | Glu | Glu | Met | Asn | Ile | Leu | Ile | Asn |
| 305 | | | | | 310 | | | | | 315 | | | | | 320 |
| Leu | Ser | Lys | Asp | Asp | Trp | Arg | Glu | Phe | Arg | Thr | Leu | Val | Ile | Glu | Met |
| | | | | 325 | | | | | 330 | | | | | 335 | |
| Val | Met | Ala | Thr | Asp | Met | Ser | Cys | His | Phe | Gln | Gln | Ile | Lys | Ala | Met |
| | | | 340 | | | | | 345 | | | | | 350 | | |
| Lys | Thr | Ala | Leu | Gln | Gln | Pro | Glu | Ala | Ile | Glu | Lys | Pro | Lys | Ala | Leu |
| | | 355 | | | | | 360 | | | | | 365 | | | |
| Ser | Leu | Met | Leu | His | Thr | Ala | Asp | Ile | Ser | His | Pro | Ala | Lys | Ala | Trp |
| | 370 | | | | | 375 | | | | | 380 | | | | |
| Asp | Leu | His | His | Arg | Trp | Thr | Met | Ser | Leu | Leu | Glu | Glu | Phe | Phe | Arg |
| 385 | | | | | 390 | | | | | 395 | | | | | 400 |
| Gln | Gly | Asp | Arg | Glu | Ala | Glu | Leu | Gly | Leu | Pro | Phe | Ser | Pro | Leu | Cys |
| | | | | 405 | | | | | 410 | | | | | 415 | |
| Asp | Arg | Lys | Ser | Thr | Met | Val | Ala | Gln | Ser | Gln | Val | Gly | Phe | Ile | Asp |
| | | | 420 | | | | | 425 | | | | | 430 | | |
| Phe | Ile | Val | Glu | Pro | Thr | Phe | Thr | Val | Leu | Thr | Asp | Met | Thr | Glu | Lys |
| | | 435 | | | | | 440 | | | | | 445 | | | |

```
Ile  Val  Ser  Pro  Leu  Ile  Asp  Glu  Thr  Ser  Gln  Thr  Gly  Gly  Thr  Gly
     450                 455                      460

Gln  Arg  Arg  Ser  Ser  Leu  Asn  Ser  Ile  Ser  Ser  Ser  Asp  Ala  Lys  Arg
465                      470                      475                      480

Ser  Gly  Val  Lys  Thr  Ser  Gly  Ser  Glu  Gly  Ser  Ala  Pro  Ile  Asn  Asn
                    485                      490                           495

Ser  Val  Ile  Ser  Val  Asp  Tyr  Lys  Ser  Phe  Lys  Ala  Thr  Trp  Thr  Glu
               500                 505                           510

Val  Val  His  Ile  Asn  Arg  Glu  Arg  Trp  Arg  Ala  Lys  Val  Pro  Lys  Glu
          515                 520                      525

Glu  Lys  Ala  Lys  Lys  Glu  Ala  Glu  Glu  Lys  Ala  Arg  Leu  Ala  Ala  Glu
     530                      535                      540

Glu  Gln  Gln  Lys  Glu  Met  Glu  Ala  Lys  Ser  Gln  Ala  Glu  Glu  Gly  Ala
545                      550                 555                           560

Ser  Gly  Lys  Ala  Glu  Lys  Lys  Thr  Ser  Gly  Glu  Thr  Lys  Asn  Gln  Val
                    565                 570                      575

Asn  Gly  Thr  Arg  Ala  Asn  Lys  Ser  Asp  Asn  Pro  Arg  Gly  Lys  Asn  Ser
               580                 585                      590

Lys  Ala  Glu  Lys  Ser  Ser  Gly  Glu  Gln  Gln  Gln  Asn  Gly  Asp  Phe  Lys
          595                      600                 605

Asp  Gly  Lys  Asn  Lys  Thr  Asp  Lys  Lys  Asp  His  Ser  Asn  Ile  Gly  Asn
     610                 615                      620

Asp  Ser  Lys  Lys  Thr  Asp  Asp  Ser  Gln  Glu
625                 630
```

( 2 ) INFORMATION FOR SEQ ID NO:52:

( i ) SEQUENCE CHARACTERISTICS:
        ( A ) LENGTH: 2077 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 2..1693

( x i ) SEQUENCE DESCRIPTION: SEQ ID NO:52:

```
A  CGG  ACA  TCA  AAC  ATG  GTT  GGA  CTG  AGC  TAT  CCA  CCA  GCT  GTT  ATT        46
   Arg  Thr  Ser  Asn  Met  Val  Gly  Leu  Ser  Tyr  Pro  Pro  Ala  Val  Ile
    1                 5                          10                       15

GAG  GCA  TTA  AAG  GAT  GTG  GAC  AAG  TGG  TCC  TTT  GAC  GTC  TTT  TCC  CTC       94
Glu  Ala  Leu  Lys  Asp  Val  Asp  Lys  Trp  Ser  Phe  Asp  Val  Phe  Ser  Leu
               20                      25                           30

AAT  GAG  GCC  AGT  GGG  GAT  CAT  GCA  CTG  AAA  TTT  ATT  TTC  TAT  GAA  CTA      142
Asn  Glu  Ala  Ser  Gly  Asp  His  Ala  Leu  Lys  Phe  Ile  Phe  Tyr  Glu  Leu
                35                      40                      45

CTC  ACA  CGT  TAT  GAT  CTG  ATC  AGC  CGT  TTC  AAG  ATC  CCC  ATT  TCT  GCA      190
Leu  Thr  Arg  Tyr  Asp  Leu  Ile  Ser  Arg  Phe  Lys  Ile  Pro  Ile  Ser  Ala
          50                      55                      60

CTT  GTC  TCA  TTT  GTG  GAG  GCC  CTG  GAA  GTG  GGA  TAC  AGC  AAG  CAC  AAA      238
Leu  Val  Ser  Phe  Val  Glu  Ala  Leu  Glu  Val  Gly  Tyr  Ser  Lys  His  Lys
65                      70                      75

AAT  CCT  TAC  CAT  AAC  TTA  ATG  CAC  GCT  GCC  GAT  GTT  ACA  CAG  ACA  GTG      286
Asn  Pro  Tyr  His  Asn  Leu  Met  His  Ala  Ala  Asp  Val  Thr  Gln  Thr  Val
80                      85                      90                      95

CAT  TAC  CTC  CTC  TAT  AAG  ACA  GGA  GTG  GCG  AAC  TGG  CTG  ACG  GAG  CTG      334
His  Tyr  Leu  Leu  Tyr  Lys  Thr  Gly  Val  Ala  Asn  Trp  Leu  Thr  Glu  Leu
```

-continued

| | | | | | | | | | | | | | | | |
|---|---|---|---|---|---|---|---|---|---|---|---|---|---|---|---|
| GAG | ATC | TTT | GCT | ATA | ATC | TTC | TCA | GCT | GCC | ATC | CAT | GAC | TAC | GAG | CAT | 382 |
| Glu | Ile | Phe | Ala | Ile | Ile | Phe | Ser | Ala | Ala | Ile | His | Asp | Tyr | Glu | His | |
| | | | 115 | | | | | 120 | | | | | 125 | | | |
| ACC | GGA | ACC | ACC | AAC | AAT | TTC | CAC | ATT | CAG | ACT | CGG | TCT | GAT | CCA | GCT | 430 |
| Thr | Gly | Thr | Thr | Asn | Asn | Phe | His | Ile | Gln | Thr | Arg | Ser | Asp | Pro | Ala | |
| | | 130 | | | | | 135 | | | | | 140 | | | | |
| ATT | CTG | TAT | AAT | GAC | AGA | TCT | GTA | CTG | GAG | AAT | CAC | CAT | TTA | AGT | GCA | 478 |
| Ile | Leu | Tyr | Asn | Asp | Arg | Ser | Val | Leu | Glu | Asn | His | His | Leu | Ser | Ala | |
| | 145 | | | | | 150 | | | | | 155 | | | | | |
| GCT | TAT | CGC | CTT | CTG | CAA | GAT | GAC | GAG | GAA | ATG | AAT | ATT | TTG | ATT | AAC | 526 |
| Ala | Tyr | Arg | Leu | Leu | Gln | Asp | Asp | Glu | Glu | Met | Asn | Ile | Leu | Ile | Asn | |
| 160 | | | | | 165 | | | | | 170 | | | | | 175 | |
| CTC | TCA | AAG | GAT | GAC | TGG | AGG | GAG | TTT | CGA | ACC | TTG | GTA | ATT | GAA | ATG | 574 |
| Leu | Ser | Lys | Asp | Asp | Trp | Arg | Glu | Phe | Arg | Thr | Leu | Val | Ile | Glu | Met | |
| | | | | 180 | | | | | 185 | | | | | 190 | | |
| GTG | ATG | GCC | ACA | GAT | ATG | TCT | TGT | CAC | TTC | CAA | CAA | ATC | AAA | GCA | ATG | 622 |
| Val | Met | Ala | Thr | Asp | Met | Ser | Cys | His | Phe | Gln | Gln | Ile | Lys | Ala | Met | |
| | | | 195 | | | | | 200 | | | | | 205 | | | |
| AAG | ACT | GCT | CTG | CAG | CAG | CCA | GAA | GCC | ATT | GAA | AAG | CCA | AAA | GCC | TTA | 670 |
| Lys | Thr | Ala | Leu | Gln | Gln | Pro | Glu | Ala | Ile | Glu | Lys | Pro | Lys | Ala | Leu | |
| | | 210 | | | | | 215 | | | | | 220 | | | | |
| TCC | CTT | ATG | CTG | CAT | ACA | GCA | GAT | ATT | AGC | CAT | CCA | GCA | AAA | GCA | TGG | 718 |
| Ser | Leu | Met | Leu | His | Thr | Ala | Asp | Ile | Ser | His | Pro | Ala | Lys | Ala | Trp | |
| | 225 | | | | | 230 | | | | | 235 | | | | | |
| GAC | CTC | CAT | CAT | CGC | TGG | ACA | ATG | TCA | CTC | CTG | GAG | GAG | TTC | TTC | AGA | 766 |
| Asp | Leu | His | His | Arg | Trp | Thr | Met | Ser | Leu | Leu | Glu | Glu | Phe | Phe | Arg | |
| 240 | | | | | 245 | | | | | 250 | | | | | 255 | |
| CAG | GGT | GAC | AGA | GAA | GCA | GAG | CTG | GGG | CTG | CCT | TTT | TCT | CCT | CTG | TGT | 814 |
| Gln | Gly | Asp | Arg | Glu | Ala | Glu | Leu | Gly | Leu | Pro | Phe | Ser | Pro | Leu | Cys | |
| | | | | 260 | | | | | 265 | | | | | 270 | | |
| GAC | CGA | AAG | TCC | ACT | ATG | GTT | GCT | CAG | TCA | CAA | GTA | GGT | TTC | ATT | GAT | 862 |
| Asp | Arg | Lys | Ser | Thr | Met | Val | Ala | Gln | Ser | Gln | Val | Gly | Phe | Ile | Asp | |
| | | | 275 | | | | | 280 | | | | | 285 | | | |
| TTC | ATC | GTG | GAA | CCC | ACC | TTC | ACT | GTG | CTT | ACG | GAC | ATG | ACC | GAG | AAG | 910 |
| Phe | Ile | Val | Glu | Pro | Thr | Phe | Thr | Val | Leu | Thr | Asp | Met | Thr | Glu | Lys | |
| | | 290 | | | | | 295 | | | | | 300 | | | | |
| ATT | GTG | AGT | CCA | TTA | ATC | GAT | GAA | ACC | TCT | CAA | ACT | GGT | GGG | ACA | GGA | 958 |
| Ile | Val | Ser | Pro | Leu | Ile | Asp | Glu | Thr | Ser | Gln | Thr | Gly | Gly | Thr | Gly | |
| | 305 | | | | | 310 | | | | | 315 | | | | | |
| CAG | AGG | CGT | TCG | AGT | TTG | AAT | AGC | ATC | AGC | TCG | TCA | GAT | GCC | AAG | CGA | 1006 |
| Gln | Arg | Arg | Ser | Ser | Leu | Asn | Ser | Ile | Ser | Ser | Ser | Asp | Ala | Lys | Arg | |
| 320 | | | | | 325 | | | | | 330 | | | | | 335 | |
| TCA | GGT | GTC | AAG | ACC | TCT | GGT | TCA | GAG | GGA | AGT | GCC | CCG | ATC | AAC | AAT | 1054 |
| Ser | Gly | Val | Lys | Thr | Ser | Gly | Ser | Glu | Gly | Ser | Ala | Pro | Ile | Asn | Asn | |
| | | | | 340 | | | | | 345 | | | | | 350 | | |
| TCT | GTC | ATC | TCC | GTT | GAC | TAT | AAG | AGC | TTT | AAA | GCT | ACT | TGG | ACG | GAA | 1102 |
| Ser | Val | Ile | Ser | Val | Asp | Tyr | Lys | Ser | Phe | Lys | Ala | Thr | Trp | Thr | Glu | |
| | | | 355 | | | | | 360 | | | | | 365 | | | |
| GTG | GTG | CAC | ATC | AAT | CGG | GAG | AGA | TGG | AGG | GCC | AAG | GTA | CCC | AAA | GAG | 1150 |
| Val | Val | His | Ile | Asn | Arg | Glu | Arg | Trp | Arg | Ala | Lys | Val | Pro | Lys | Glu | |
| | | 370 | | | | | 375 | | | | | 380 | | | | |
| GAG | AAG | GCC | AAG | AAG | GAA | GCA | GAG | GAA | AAG | GCT | CGC | CTG | GCC | GCA | GAG | 1198 |
| Glu | Lys | Ala | Lys | Lys | Glu | Ala | Glu | Glu | Lys | Ala | Arg | Leu | Ala | Ala | Glu | |
| | 385 | | | | | 390 | | | | | 395 | | | | | |
| GAG | CAG | CAA | AAG | GAA | ATG | GAA | GCC | AAA | AGC | CAG | GCT | GAA | GAA | GGC | GCA | 1246 |
| Glu | Gln | Gln | Lys | Glu | Met | Glu | Ala | Lys | Ser | Gln | Ala | Glu | Glu | Gly | Ala | |
| 400 | | | | | 405 | | | | | 410 | | | | | 415 | |
| TCT | GGC | AAA | GCT | GAG | AAA | AAG | ACG | TCT | GGA | GAA | ACT | AAG | AAT | CAA | GTC | 1294 |
| Ser | Gly | Lys | Ala | Glu | Lys | Lys | Thr | Ser | Gly | Glu | Thr | Lys | Asn | Gln | Val | |

-continued

|     |     |     |     |     |     |     |     |     |     |     |     |     |     |     |      |
|-----|-----|-----|-----|-----|-----|-----|-----|-----|-----|-----|-----|-----|-----|-----|------|
| AAT | GGA | ACA | CGG | GCA | AAC | AAA | AGT | GAC | AAC | CCT | CGT | GGG | AAA | AAT | TCC  | 1342
| Asn | Gly | Thr | Arg | Ala | Asn | Lys | Ser | Asp | Asn | Pro | Arg | Gly | Lys | Asn | Ser  |
|     |     |     | 435 |     |     |     |     | 440 |     |     |     |     | 445 |     |      |
| AAA | GCT | GAG | AAG | TCA | TCA | GGA | GAA | CAG | CAA | CAG | AAT | GGT | GAC | TTC | AAA  | 1390
| Lys | Ala | Glu | Lys | Ser | Ser | Gly | Glu | Gln | Gln | Gln | Asn | Gly | Asp | Phe | Lys  |
|     |     | 450 |     |     |     |     | 455 |     |     |     |     | 460 |     |     |      |
| GAT | GGT | AAA | AAT | AAG | ACA | GAC | AAG | AAG | GAT | CAC | TCT | AAC | ATC | GGA | AAT  | 1438
| Asp | Gly | Lys | Asn | Lys | Thr | Asp | Lys | Lys | Asp | His | Ser | Asn | Ile | Gly | Asn  |
|     | 465 |     |     |     |     | 470 |     |     |     |     | 475 |     |     |     |      |
| GAT | TCA | AAG | AAA | ACA | GAT | GGC | ACA | AAA | CAG | CGT | TCT | CAC | GGC | TCA | CCA  | 1486
| Asp | Ser | Lys | Lys | Thr | Asp | Gly | Thr | Lys | Gln | Arg | Ser | His | Gly | Ser | Pro  |
| 480 |     |     |     |     | 485 |     |     |     |     | 490 |     |     |     |     | 495  |
| GCC | CCA | AGC | ACC | AGC | TCC | ACG | TGT | CGC | CTT | ACG | TTG | CCA | GTC | ATC | AAG  | 1534
| Ala | Pro | Ser | Thr | Ser | Ser | Thr | Cys | Arg | Leu | Thr | Leu | Pro | Val | Ile | Lys  |
|     |     |     |     | 500 |     |     |     |     | 505 |     |     |     |     | 510 |      |
| CCT | CCT | TTG | CGT | CAT | TTT | AAA | CGC | CCT | GCT | TAC | GCA | TCT | AGC | TCC | TAT  | 1582
| Pro | Pro | Leu | Arg | His | Phe | Lys | Arg | Pro | Ala | Tyr | Ala | Ser | Ser | Ser | Tyr  |
|     |     |     |     | 515 |     |     |     |     | 520 |     |     |     | 525 |     |      |
| GCA | CCT | TCA | GTC | TCA | AAG | AAA | ACT | GAT | GAG | CAT | CCT | GCA | AGG | TAC | AAG  | 1630
| Ala | Pro | Ser | Val | Ser | Lys | Lys | Thr | Asp | Glu | His | Pro | Ala | Arg | Tyr | Lys  |
|     |     | 530 |     |     |     |     | 535 |     |     |     |     | 540 |     |     |      |
| ATG | CTA | GAT | CAG | AGG | ATC | AAA | ATG | AAA | AAG | ATT | CAG | AAC | ATC | TCA | CAT  | 1678
| Met | Leu | Asp | Gln | Arg | Ile | Lys | Met | Lys | Lys | Ile | Gln | Asn | Ile | Ser | His  |
|     | 545 |     |     |     |     | 550 |     |     |     |     | 555 |     |     |     |      |
| AAC | TGG | AAC | AGA | AAA | TAGGCCGAGG | GGAAGAAGAG | AGGGAGTGAA | GGAGGGTCTA | | | | | | | 1733
| Asn | Trp | Asn | Arg | Lys |  |  |  |  | | | | | | | |
| 560 |     |     |     |     |  |  |  |  | | | | | | | |

CCTATCTGCT TCTCAGCACC CACTGGCCAC AGCAGGACAC ACCTCCAAGA CCCTTGGAGG     1793

CTGTTGGAGC AGGTACTATC CTGGTTGACT CCACCAAGGT GAAATGAAAG TTGTATGTGA     1853

TTTTCCTCTT TGTTGTTCTT GTATAGACTT TTCAATTGCT GTATGTGGGA TCAGCCCAGA     1913

CGCCAGCAAC AAACTAGCAA GAGGGGTGTT TTTATGGTAT AAGTCTCTAA AAGTCTAAAT     1973

TGGACCAAAA TTAAAATGAC ACAAACTTAA AAAAAAATAA AATTCCTCTC ATTGCCACTT     2033

TTTTCAATCT CTAAAAGTTA CTTGCCCCCA AAAGAATATT GGTC     2077

( 2 ) INFORMATION FOR SEQ ID NO:53:

( i ) SEQUENCE CHARACTERISTICS:
        ( A ) LENGTH: 564 amino acids
        ( B ) TYPE: amino acid
        ( D ) TOPOLOGY: linear ( i i ) MOLECULE TYPE: protein ( x i ) SEQUENCE DESCRIPTION: SEQ ID NO:53:

| Arg | Thr | Ser | Asn | Met | Val | Gly | Leu | Ser | Tyr | Pro | Pro | Ala | Val | Ile | Glu |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Ala | Leu | Lys | Asp | Val | Asp | Lys | Trp | Ser | Phe | Asp | Val | Phe | Ser | Leu | Asn |
|     |     |     | 20  |     |     |     |     | 25  |     |     |     |     | 30  |     |     |
| Glu | Ala | Ser | Gly | Asp | His | Ala | Leu | Lys | Phe | Ile | Phe | Tyr | Glu | Leu | Leu |
|     |     | 35  |     |     |     |     | 40  |     |     |     |     | 45  |     |     |     |
| Thr | Arg | Tyr | Asp | Leu | Ile | Ser | Arg | Phe | Lys | Ile | Pro | Ile | Ser | Ala | Leu |
|     | 50  |     |     |     |     | 55  |     |     |     |     | 60  |     |     |     |     |
| Val | Ser | Phe | Val | Glu | Ala | Leu | Glu | Val | Gly | Tyr | Ser | Lys | His | Lys | Asn |
| 65  |     |     |     |     | 70  |     |     |     |     | 75  |     |     |     |     | 80  |
| Pro | Tyr | His | Asn | Leu | Met | His | Ala | Ala | Asp | Val | Thr | Gln | Thr | Val | His |
|     |     |     |     | 85  |     |     |     |     | 90  |     |     |     |     | 95  |     |

| | | | | | | | | | | | | | | |
|---|---|---|---|---|---|---|---|---|---|---|---|---|---|---|
| Tyr | Leu | Leu | Tyr 100 | Lys | Thr | Gly | Val | Ala 105 | Asn | Trp | Leu | Thr 110 | Glu | Leu | Glu |
| Ile | Phe | Ala 115 | Ile | Ile | Phe | Ser | Ala 120 | Ala | Ile | His | Asp | Tyr 125 | Glu | His | Thr |
| Gly | Thr 130 | Thr | Asn | Asn | Phe | His 135 | Ile | Gln | Thr | Arg | Ser 140 | Asp | Pro | Ala | Ile |
| Leu 145 | Tyr | Asn | Asp | Arg | Ser 150 | Val | Leu | Glu | Asn | His 155 | His | Leu | Ser | Ala | Ala 160 |
| Tyr | Arg | Leu | Leu | Gln 165 | Asp | Asp | Glu | Glu | Met 170 | Asn | Ile | Leu | Ile | Asn 175 | Leu |
| Ser | Lys | Asp | Asp 180 | Trp | Arg | Glu | Phe | Arg 185 | Thr | Leu | Val | Ile 190 | Glu | Met | Val |
| Met | Ala | Thr 195 | Asp | Met | Ser | Cys | His 200 | Phe | Gln | Gln | Ile | Lys 205 | Ala | Met | Lys |
| Thr | Ala 210 | Leu | Gln | Gln | Pro | Glu 215 | Ala | Ile | Glu | Lys | Pro 220 | Lys | Ala | Leu | Ser |
| Leu 225 | Met | Leu | His | Thr | Ala 230 | Asp | Ile | Ser | His | Pro 235 | Ala | Lys | Ala | Trp | Asp 240 |
| Leu | His | His | Arg | Trp 245 | Thr | Met | Ser | Leu | Leu 250 | Glu | Glu | Phe | Phe | Arg 255 | Gln |
| Gly | Asp | Arg | Glu 260 | Ala | Glu | Leu | Gly | Leu 265 | Pro | Phe | Ser | Pro 270 | Leu | Cys | Asp |
| Arg | Lys | Ser 275 | Thr | Met | Val | Ala | Gln 280 | Ser | Gln | Val | Gly | Phe 285 | Ile | Asp | Phe |
| Ile | Val 290 | Glu | Pro | Thr | Phe | Thr 295 | Val | Leu | Thr | Asp | Met 300 | Thr | Glu | Lys | Ile |
| Val 305 | Ser | Pro | Leu | Ile | Asp 310 | Glu | Thr | Ser | Gln | Thr 315 | Gly | Gly | Thr | Gly | Gln 320 |
| Arg | Arg | Ser | Ser | Leu 325 | Asn | Ser | Ile | Ser | Ser 330 | Ser | Asp | Ala | Lys | Arg 335 | Ser |
| Gly | Val | Lys | Thr 340 | Ser | Gly | Ser | Glu | Gly 345 | Ser | Ala | Pro | Ile 350 | Asn | Asn | Ser |
| Val | Ile | Ser 355 | Val | Asp | Tyr | Lys | Ser 360 | Phe | Lys | Ala | Thr | Trp 365 | Thr | Glu | Val |
| Val | His 370 | Ile | Asn | Arg | Glu | Arg 375 | Trp | Arg | Ala | Lys | Val 380 | Pro | Lys | Glu | Glu |
| Lys 385 | Ala | Lys | Lys | Glu | Ala 390 | Glu | Gln | Lys | Ala | Arg 395 | Leu | Ala | Ala | Glu | Glu 400 |
| Gln | Gln | Lys | Glu | Met 405 | Glu | Ala | Lys | Ser | Gln 410 | Ala | Glu | Glu | Gly | Ala 415 | Ser |
| Gly | Lys | Ala | Glu 420 | Lys | Lys | Thr | Ser | Gly 425 | Glu | Thr | Lys | Asn 430 | Gln | Val | Asn |
| Gly | Thr | Arg 435 | Ala | Asn | Lys | Ser | Asp 440 | Asn | Pro | Arg | Gly | Lys 445 | Asn | Ser | Lys |
| Ala | Glu 450 | Lys | Ser | Ser | Gly | Gln 455 | Gln | Gln | Asn | Gly | Asp 460 | Phe | Lys | Asp |
| Gly | Lys 465 | Asn | Lys | Thr | Asp 470 | Lys | Lys | Asp | His | Ser 475 | Asn | Ile | Gly | Asn | Asp 480 |
| Ser | Lys | Lys | Thr | Asp 485 | Gly | Thr | Lys | Gln | Arg 490 | Ser | His | Gly | Ser | Pro 495 | Ala |
| Pro | Ser | Thr | Ser 500 | Ser | Thr | Cys | Arg | Leu 505 | Thr | Leu | Pro | Val 510 | Ile | Lys | Pro |
| Pro | Leu | Arg 515 | His | Phe | Lys | Arg | Pro 520 | Ala | Tyr | Ala | Ser | Ser 525 | Ser | Tyr | Ala |

```
Pro  Ser  Val  Ser  Lys  Lys  Thr  Asp  Glu  His  Pro  Ala  Arg  Tyr  Lys  Met
     530                      535                     540

Leu  Asp  Gln  Arg  Ile  Lys  Met  Lys  Lys  Ile  Gln  Asn  Ile  Ser  His  Asn
545                      550                     555                     560

Trp  Asn  Arg  Lys
```

( 2 ) INFORMATION FOR SEQ ID NO:54:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:54:

TACGAAGCTT TGATGGGGTC TACTGCTAC        29

( 2 ) INFORMATION FOR SEQ ID NO:55:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:55:

TACGAAGCTT TGATGGTTGG CTTGGCATAT C        31

( 2 ) INFORMATION FOR SEQ ID NO:56:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:56:

ATTACCCCTC ATAAAG        16

( 2 ) INFORMATION FOR SEQ ID NO:57:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:57:

TACGAAGCTT TGATGCGCCG ACAGCCTGC        29

( 2 ) INFORMATION FOR SEQ ID NO:58:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:58:

GGTCTCCTGT TGCAGATATT G  21